(12) United States Patent
Asari et al.

(10) Patent No.: US 7,601,488 B2
(45) Date of Patent: Oct. 13, 2009

(54) HYALURONIC ACID OLIGOSACCHARIDE FRACTIONS AND DRUGS CONTAINING THE SAME

(75) Inventors: Akira Asari, Saitama (JP); Hitoshi Kurihara, Tokyo (JP); Tomomi Shibata, Osaka (JP); Yuka Miyazaki, Tokyo (JP); Hiroko Yamanokuchi, Saitama (JP); Akira Tawada, Saitama (JP); Takahiro Masa, Tokyo (JP); Yuji Matsuzaki, Saitama (JP)

(73) Assignee: Seikagaku Corporation, Tokyo (JP)

( * ) Notice: Subject to any disclaimer, the term of this patent is extended or adjusted under 35 U.S.C. 154(b) by 454 days.

(21) Appl. No.: 11/622,673

(22) Filed: Jan. 12, 2007

(65) Prior Publication Data

US 2007/0134646 A1 Jun. 14, 2007

Related U.S. Application Data

(62) Division of application No. 10/312,879, filed as application No. PCT/JP01/05918 on Jul. 6, 2001, now Pat. No. 7,507,723.

(30) Foreign Application Priority Data

Jul. 7, 2000 (JP) ............................ 2000-206404
Aug. 17, 2000 (JP) ............................ 2000-247840

(51) Int. Cl.
*A01N 1/02* (2006.01)
*A61K 31/702* (2006.01)

(52) U.S. Cl. ......................................... 435/1.1; 514/61
(58) Field of Classification Search ....................... None
See application file for complete search history.

(56) References Cited

U.S. PATENT DOCUMENTS

| 4,141,973 A | 2/1979 | Balazs ..................... 424/180 |
| 5,902,795 A | 5/1999 | Toole et al. .................... 514/54 |

FOREIGN PATENT DOCUMENTS

| JP | 9-227386 | 9/1997 |
| JP | 09-227386 | 9/1997 |
| JP | 11-246301 | 9/1999 |
| JP | 11-310588 | 11/1999 |
| JP | 2000-103738 | 4/2000 |
| WO | 97/37537 | 10/1997 |
| WO | WO 97/37537 | 10/1997 |

OTHER PUBLICATIONS

Clavien, P. "Sinusoidal endothelial cell injury during hepatic preservation and reperfusion" Hepatology (1998) vol. 28, No. 2, pp. 281-285.*
Roberto Gilli et al., "FTIR Studies of Sodium Hyaluronate And Its Oligomers in the Amorphous Solid Phase and Aqueous Solution," Carbohydrate Research, vol. 263, pp. 315-326 (1994).
Cowman, M. et al., "Preparation and Circular Dichroism Analysis of Sodium Hyaluronate Oligosaccharides and Chrondroitin," Biochemistry (1981) vol. 20, No. 5, pp. 1379-1385.
Renato Toffanin et al., NMR Studies of Oligosaccharides Derived from Hyaluronate: Complete Assignment of 1H and 13CNMR Spectra of Aqueous Di- and Tetra-saccharides, and Comparison of Chemical Shifts for Oligosaccharides of Increasing Degree of Polymerisation, Carbohydrate Research, vol. 245 (1993) 113-128.
R. Gilli, et al., "FTIR Studies of Sodium Hyaluronate and its Oligomers in the Amorphous Solid Phase and in Aqueous Solution", Carbohydrate Research, 1994, vol. 263, pp. 315-326.
P. Bertrand, et al., "Interaction of Hyaluronectin with Hyaluronic Acid Oligosaccharides", Journal of Neurochemistry, vol. 45, No. 2, 1985, pp. 434-439, XP-000874493.
E. Shimada, et al., "Degradation Process of Hyaluronic Acid", Journal of Biochemistry, vol. 88, No. 4, 1980, pp. 1015-1023, XP-001032517.

* cited by examiner

*Primary Examiner*—Leigh C Maier
(74) *Attorney, Agent, or Firm*—Oblon, Spivak, McClelland, Maier & Neustadt, L.L.P.

(57) ABSTRACT

A method for promoting expression of a heat shock protein, or for inhibiting cell injury or cell death, or for treating a disease for which cell or tissue protection is desired, or for promoting production of IL-10, or for inhibiting production of IL-8, by administering an effective amount of a fraction containing a hyaluronic acid tetrasaccharide comprising four saccharide residues and having certain physicochemical properties or by administering an effective amount of an isolated and substantially pure tetrasaccharide of formula (1) described in the application. Methods for preserving an organ.

3 Claims, 47 Drawing Sheets

Lane    1   2   3   4   5   6   7   8

Fig. 22
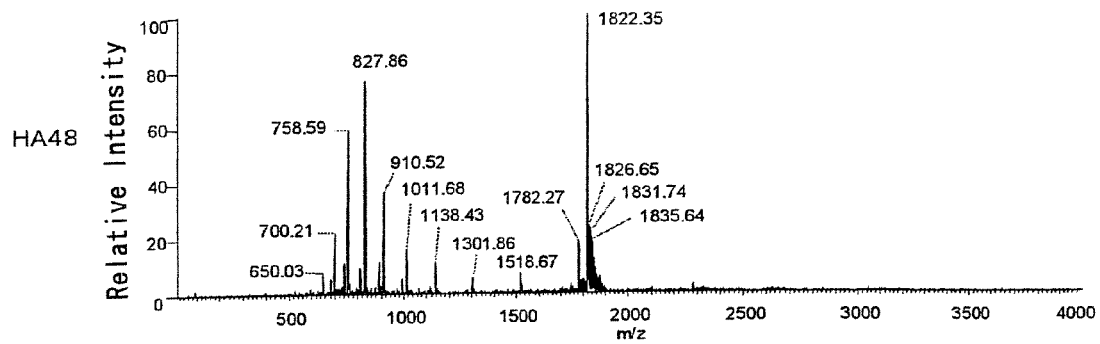
HA48
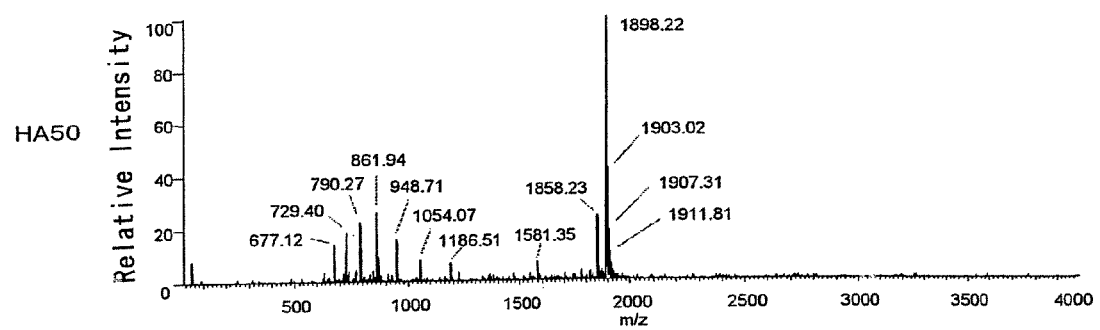
HA50
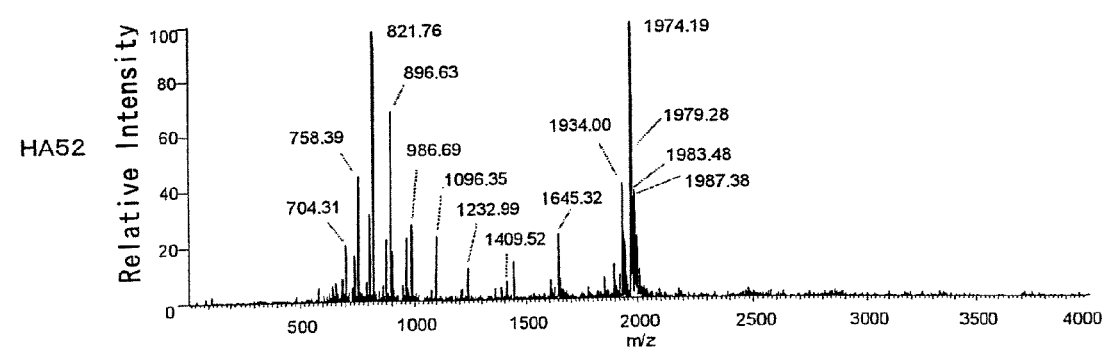
HA52

St : Standard HSF1 (Derived From Bacteria)

HYALURONIC ACID OLIGOSACCHARIDE FRACTIONS AND DRUGS CONTAINING THE SAME

This application is a divisional of U.S. application Ser. No. 10/312,879, filed Jun. 30, 2003, which is a National Stage application of PCT/JP01/05918, filed Jul. 26, 2001; and claims priority to Japanese Applications 2000-206404, filed Jul. 7, 2000; and 2000-247840, filed Aug. 17, 2000.

TECHNICAL FIELD

The present invention relates to hyaluronic acid oligosaccharides (henceforth also referred to as "HA oligosaccharides") and novel fractions thereof.

The present invention also relates to drugs containing the HA oligosaccharides (in particular, a heat shock protein expression promoter, cell death inhibitor, cell injury inhibitor or cell and tissue protecting agent (especially those used for applications as an organ preservation agent, antiulcer agent and antihepatopathic agent, IL-10 production promoter or IL-8 production inhibitor)) as active ingredients.

BACKGROUND ART

It is known that activities and functions of hyaluronic acid (henceforth also referred to as "HA") change depending on the molecular size. For example, it has been reported that HA having a molecular weight of 1,200,000 shows NF-κB inactivation activity, neovascularization inhibition activity and so forth (Neumann A., Schinzel R., Palm D., Riederer P. and Munch G., "High molecular weight hyaluronic acid inhibits advanced glycation endproduct-induced NF-κB activation and cytokine expression", FEBS Lett., 453 (3):283-7, Jun. 25, 1999; Feinberg R. N., Beebe D. C., Hyaluronate in vasculogenesis, Science 220:1177-1179, 1983), whereas HA having a molecular weight of 500,000 or less has inverse activities (Noble P. W., McKee C. M., Cowman M. and Shin H. S., "Hyaluronan fragments activate an NF-κB/I-κB alpha autoregulatory loop in murine macrophages", J. Exp. Med. 183: 2373-2378, 1996.; West D. C. and Shaw D. M., "Tumour hyaluronan in relation to angiogenesis and metastasis", In: Laurent T. C. ed., The chemistry, biology and medical applications of hyaluronan and its derivatives, London: Portland Press, 1998:227).

It can be said that this well suggests possibilities of finding of various activities also for HA oligosaccharides and finding of specific activities depending on sizes of HA oligosaccharides. Therefore, it can be considered that, if HA oligosaccharides having different sizes are combined, they may exert an additive or synergistic effect, or conversely, against an activity of an HA oligosaccharide of a certain size, another HA oligosaccharide having a different size may act as an antagonist.

Assuming as described above, if a fraction containing HA oligosaccharides of various sizes is used for search of activities thereof for development of drugs utilizing HA oligosaccharides, not only it cannot be found which size of HA oligosaccharide constitutes an entity of a certain activity, but also an activity of HA oligosaccharide of a certain size may be compensated by an HA oligosaccharide of another size. Thus, important physiological activities or functions hidden in HA oligosaccharides may be overlooked.

Further, when an HA oligosaccharide of a certain specific size is used as a drug, it is necessary to eliminate oligosaccharides of other sizes that inhibit the function exerted by the HA oligosaccharide of specific size as much as possible, and there has been desired a fraction of high purity that does not substantially contain substances undesirable for drugs.

As described above, for creation and provision of novel drugs, there has been desired a HA oligosaccharide fraction of high purity that consists of HA oligosaccharides of substantially uniform sizes and does not substantially contain HA oligosaccharides of other sizes and other impurities.

Meanwhile, heat shock proteins (henceforth also referred to as "Hsp") are also called stress proteins, which are proteins that inhibit affections caused by various stress reactions, and various families thereof have been known. The heat shock proteins of Hsp70 family, which is one of the families, are considered to prevent cell injury or cell death through actions of inhibiting structural changes of proteins, production of abnormal proteins and so forth caused by factors generating environmental stresses such as heat shock, hydrogen peroxide, heavy metals, amino acid analogues and glucose depletion and stress factors such as fervescence, inflammation, ischemia, viral infection, metabolic disorders, hypercardia, oxidative stresses, cellular tissue affections, oncogenes and carcinogenic substances or actions of regenerating functions of proteins.

In connection with the above, a stress protein expression promoter containing HA as an active ingredient is disclosed in Japanese Patent Unexamined Publication (Kokai) No. 9-227386. In this patent document, it is described that HA consisting of about 2 to 20 saccharides is preferred as the active ingredient (page 3), and it was suggested that HA consisting of ten or less saccharides was involved in enhancement or induction of expression of stress proteins (page 6). There is also described an experiment demonstrating that an unsaturated HA disaccharide enhanced expression of a stress protein and inhibited cell death (Example 2).

However, the above patent document does not specifically disclose various oligosaccharides as in the present invention, and it does not teach nor suggest at all the extremely notable activity for enhancement of expression of stress protein specifically observed for HA tetrasaccharide mentioned later.

Further, considering the functions of the aforementioned stress proteins, the stress proteins are considered to be involved also in protection of cells and tissues.

Concerning the above, Japanese Patent Unexamined Publication No. 11-246301 discloses an organ preservation solution for use in organ transplantation containing HA and/or a physiologically acceptable salt thereof. Although this patent document describes that the average molecular weight of HA is preferably 100,000 or more, it does not describe nor suggest HA oligosaccharides and superior effects exerted by them.

DISCLOSURE OF THE INVENTION

An object of the present invention is to provide a fraction that contains HA oligosaccharides having a size of about 4 to 60 saccharides, in particular, HA oligosaccharide of a substantially uniform size, and does not substantially contain HA oligosaccharides of other sizes and other impurities.

Another object of the present invention is to provide a useful drug containing such HA oligosaccharides as an active ingredient, especially a more effective Hsp expression promoter, cell death inhibitor or cell injury inhibitor. A further object of the present invention is to provide a cell and tissue protecting agent and provide an organ preservation agent, antiulcer agent and antihepatopathic agent, IL-10 production promoter and IL-8 production inhibitor utilizing it.

The inventors of the present invention assiduously studied in order to achieve the aforementioned objects. As a result, they obtained novel fractions of HA oligosaccharides that consisted substantially only of oligosaccharide of a desired size and did not substantially contain oligosaccharides of other size and other impurities by fractionating HA oligosaccharides having a size selected from sizes of 4 to 60 saccharides and a mixture of such oligosaccharides with a particular method.

Thus, the present invention provides an HA oligosaccharide having a size selected from sizes of 4 to 60 saccharides (henceforth also referred to as "oligosaccharide of the present invention").

The present invention also provides a fraction containing the oligosaccharide of the present invention and having the physicochemical properties defined in the following (1) to (6) (henceforth also referred to as "fraction of the present invention").

(1) If the fraction is analyzed by the detection methods mentioned in the following (a) and (b) using gel filtration chromatography, the fraction shows a substantially single peak in both of the methods, and the peaks have peak areas defined in the following (a) and (b).
(a) If the detection is performed based on absorbance at 210 nm, a relative ratio of peak area of the substantially single peak to the sum of peak areas of total HA oligosaccharides in the fraction is 85% or more.
(b) If the detection is performed by using a differential refractometer, a relative ratio of peak area of the substantially single peak to the sum of peak areas of total HA oligosaccharides in the fraction is 98% or more.
(2) If the fraction is analyzed based on absorbance at 210 nm by using anion exchange chromatography, the fraction shows a substantially single peak, and a relative ratio of peak area of the substantially single peak to the sum of peak areas of total HA oligosaccharides in the fraction is 90% or more.
(3) If oligosaccharides in the fraction are labeled with fluorescence and then analyzed by electrophoresis, a single band is detected, and bands of HA oligosaccharides of other sizes are not detected.
(4) If a theoretical value of monoisotopic molecular weight or average molecular weight of HA oligosaccharides constituting the fraction is taken as 1, an actual value of the same measured for the fraction by mass spectrometry is 0.997 to 1.003 (relative value).
(5) Respective differences between theoretical values (weight %) of carbon (C), hydrogen (H) and nitrogen (N) contents in HA oligosaccharides constituting the fraction and values actually measured for the elements by elemental analysis of the fraction (weight %) are all in the range of ±1 (weight %).
(6) The fraction does not substantially contain proteins, DNA and endotoxins.

The fraction of the present invention preferably further shows the physicochemical property defined in the following (7).
(7) Results of $^1$H-NMR and $^{13}$C-NMR of the fraction do not contradict to the structure of HA oligosaccharide represented by the following formula (1).

(In the formula, n is an integer of 1 to 29, M represents a proton or a monovalent cation, and AC represents acetyl group.)

The size of HA oligosaccharides contained in the fraction of the present invention is preferably selected from sizes of 4 to 20 saccharides, more preferably selected from sizes of 4 to 16 saccharides, still more preferably selected from sizes of 4 to 14 saccharides, and it is most preferably a size of 4 saccharides (tetrasaccharides).

Moreover, the inventors of the present invention investigated possibility of use of HA oligosaccharides of the present invention as a drug. As a result, they found that an HA oligosaccharide of a particular size had extremely notable Hsp expression promoting action, cell death inhibitory action and cell injury inhibitory action, and thereby provided an Hsp expression promoter, cell death inhibitor and cell injury inhibitor that can achieve the aforementioned object.

The inventors of the present invention further found that the oligosaccharide of the present invention had a superior cell and tissue protection action, and thus further provided a cell and tissue protecting agent as well as an organ preservation agent, antiulcer agent, antihepatopathic agent, IL-10 production promoter and IL-8 production inhibitor utilizing it.

That is, the present invention provides a drug (pharmaceutical composition, also referred to as "drug of the present invention" hereinafter) containing the oligosaccharide of the present invention as an active ingredient. This drug is preferably an Hsp expression promoter, cell death inhibitor, cell injury inhibitor or cell and tissue protecting agent.

Moreover, the cell and tissue protecting agent is preferably used for applications as an organ preservation agent, antiulcer agent, antihepatopathic agent, IL-10 production promoter and IL-8 production inhibitor.

The drug and agents of the present invention preferably contain, as an active ingredient, an HA oligosaccharide having a size selected from sizes of 4 to 20 saccharides, more preferably an HA oligosaccharide having a size selected from sizes of 4 to 16 saccharides, still more preferably an HA oligosaccharide having a size selected from sizes of 4 to 14 saccharides, most preferably an HA oligosaccharide having a size of 4 saccharides.

As described above, physiological activities and functions of HA oligosaccharides had also hitherto been reported. However, there have hitherto been no examples of use of HA oligosaccharides guaranteed on many aspects such as molecular size, molecular structure and purity (contents of oligosaccharides of other sizes and contents of other components such as proteins and DNA, contents of endotoxins). That is, as for the physiological activities and functions of HA oligosaccharides mentioned in the previous reports, influences of contaminants could not be denied. On the other hand, in the present invention, a fraction of HA oligosaccharide not substantially containing other components such as proteins

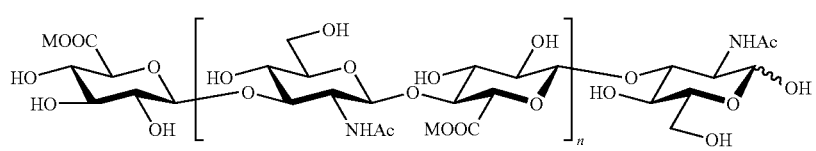

Formula (1)

and DNA or such an HA oligosaccharide not substantially containing HA oligosaccharides of other sizes was obtained, and physiological activities and functions thereof were elucidated.

Hereafter, the present invention will be explained in detail.

<1> Oligosaccharide of the Present Invention

The oligosaccharide of the present invention is an HA oligosaccharide having a size selected from sizes of 4 to 60 saccharides.

The "HA oligosaccharide" used herein is an oligosaccharide having a composition similar to the constitutive disaccharide composition of HA. Specifically, it refers to an oligosaccharide consisting of alternately linked residues of glucuronic acid (GlcA) and N-acetylglucosamine (GlcNAc), which are constitutive monosaccharides of HA.

That is, the HA oligosaccharide include an oligosaccharide having glucuronic acid residue at the non-reducing end, of which typical example is the structure represented by the aforementioned formula (1), as well as an oligosaccharide having N-acetylglucosamine residue at the non-reducing end.

The saccharide locating at the non-reducing end may be a saturated saccharide (monosaccharide not containing a double bond as a carbon-carbon bond) or an unsaturated saccharide (monosaccharide containing a double bond as a carbon-carbon bond). In the following explanations, GlcA represents saturated glucuronic acid residue and ΔGlcA represents unsaturated glucuronic acid residue.

An oligosaccharide whose saccharide locating at the non-reducing end is a saturated saccharide is especially preferred. Specifically, HA oligosaccharides represented by the following formula (2) are preferred.

GlcA(-GlcNAc-GlcA)n-GlcNAc    (2)

(In the formula, GlcA represents a glucuronic acid residue, GlcNAc represents an N-acetylglucosamine residue, - represents a glycosidic linkage, and n represents an integer of 1 to 29.)

The glycosidic linkage of GlcA-GlcNAc in the aforementioned formula (2) is preferably a β1−>3 linkage, and the glycosidic linkage in GlcNAc-GlcA is preferably a β1−>4 linkage.

Among those, HA oligosaccharides represented by the following formula (1) are particularly preferred.

(In the formula, n is an integer of 1 to 29, M represents a proton or a monovalent cation, and Ac represents acetyl group.)

However, those having an unsaturated saccharide as a saccharide locating at the non-reducing end also have significant physiological activity as demonstrated in the examples mentioned later, and they are also preferred embodiments of the present invention. Specific examples thereof include an HA oligosaccharide represented by the following formula.

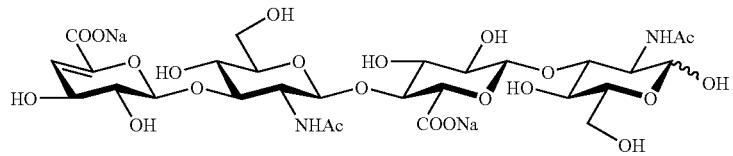

(In the formula, Ac represents an acetyl group.)

An HA oligosaccharide represented by the aforementioned formula and having an unsaturated saccharide at the non-reducing end corresponds to ΔHA4 used in the examples mentioned later.

Further, the oligosaccharide of the present invention may be in the form of a salt, and may be in an ionized state. Examples of the salt include, for example, salts with an inorganic base such as alkali metal salts (sodium salt, lithium salt, potassium salt etc.), alkaline earth metal salts and ammonium salts and salts with an organic base such as diethanolamine salts, cyclohexylamine salts, amino acid salts, galactosamine salts and glucosamine salts. Among these, alkali metal salts are preferred, and sodium salts are particularly preferred.

A source of the oligosaccharide of the present invention is not particularly limited. For example, the oligosaccharide of the present invention may be produced by a process comprising separation and purification of HA from chicken crest, umbilical cord, porcine skin, bovine skin, skins or aortas of fish and other animals, microorganisms producing HA and so forth and degradation of HA (e.g., enzymatic degradation, chemical degradation, heat treatment, ultrasonication etc.). The oligosaccharide of the present invention may also be produced by a synthetic process (e.g., chemical synthesis and enzymatic synthesis).

Examples of the enzymatic degradation method include methods of allowing an enzyme that degrades HA such as hyaluronidase (derived from testis), hyaluronidase (derived from Streptomyces), hyaluronidase SD, chondroitinase ACI, chondroitinase ACIII, chondroitinase ABC and endoglucuronidase (derived from leech) to act on HA (refer to Shin Seikagaku Jikken Koza [Lecture of Biochemical Experi- Formula (1)

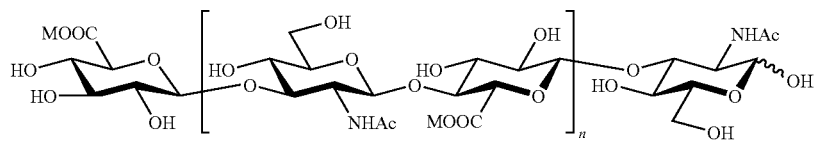

ments, New Edition], "Saccharide II, Proteoglycan and Glycosaminoglycan", published by Tokyo Kagaku Dojin, pp. 244-248, 1991). In order to obtain an HA oligosaccharide of the aforementioned formula (1), a hydrolase is preferably used as the enzyme that degrades HA.

Examples of the chemical degradation method include the alkaline decomposition method, dimethyl sulfoxide method (DMSO method) and so forth. The alkaline decomposition method can be specifically performed by, for example, adding a base such as about 1 N sodium hydroxide to a solution of HA, warming the mixture for several hours to degrade HA into those of lower molecular weights and then neutralizing the mixture with addition of an acid such as hydrochloric acid. Examples of the DMSO method include the method of Nagasawa et al. (Carbohyd. Res., 141, pp. 99-110, 1985). The hydrolysis can also be carried out by using an acid such as hydrochloric acid and sulfuric acid.

Examples of the ultrasonication method include the method described in Biochem., 33, pp. 6503-6507, 1994 and so forth.

Examples of the synthesis method include the methods described in Glycoconjugate J., pp. 453-439, 1993; International Patent Publication WO93/20827 and so forth.

The oligosaccharide of the present invention produced as described above can be purified to a desired purity. It can be purified to such a degree that the oligosaccharide of the present invention should substantially consist of oligosaccharide of a uniform size and not substantially contain HA oligosaccharides of other sizes and other impurities, for example, as described below.

<2> Fraction of the Present Invention

The fraction of the present invention is a fraction containing the oligosaccharide of the present invention and showing the specific physicochemical properties described later.

Although the oligosaccharide of the present invention (fraction containing oligosaccharide of the present invention, different from the fraction of the present invention) by the method described in the above section <1>, the obtained fraction contains HA oligosaccharides of multiple kinds of sizes as an admixture. On the other hand, the fraction of the present invention comprises HA oligosaccharide of a substantially uniform size, and does not substantially contain HA oligosaccharides of other sizes and other impurities. The fraction of the present invention can be produced by the method described below.

The fraction obtained by the method described in the above <1> (fraction containing oligosaccharides of various sizes as an admixture) is applied to a column of strongly basic anion exchanger. Examples of the strongly basic anion exchanger include anion exchangers having trimethylammonium groups, trimethylammoniomethyl groups, β-hydroxyethyldimethylammonium groups, 2-hydroxypropylamino groups, diethyl-(2-hydroxypropyl)aminoethyl groups, dimethylethanolammonium groups or the like, and an anion exchanger having trimethylammoniomethyl groups is preferred.

Although size of the column can be suitably selected depending on the amount to be applied and so forth, a column diameter of 1 to 5 cm and a column length of about 50 to 150 cm are preferred for the preparation in a small scale. Further, two or more of such columns are preferably combined.

If a fraction containing HA oligosaccharides of multiple kinds of sizes as an admixture is applied to such a column, HA oligosaccharides contained in the fraction bind to the strongly basic anion exchanger in the column via ionic bonds.

The bound HA oligosaccharides can be eluted with a salt concentration gradient. The salt used for the elution is not particularly limited, and NaCl, KCl, LiCl etc. can be used. However, NaCl is preferably used.

The salt concentration gradient is preferably started at a salt concentration of about 0 to 0.1 M and increased to about 0.5 M. Further, the salt concentration gradient is preferably linear, and the salt concentration is preferably increased with a rate of about 0.1 M/40 to 50 hours, more preferably about 0.1 M/45 to 50 hours.

Further, the flow rate is preferably 80 to 100 mL/hour, more preferably 85 to 95 mL/hour.

By selecting such chromatographic conditions, HA oligosaccharides bound to the strongly basic anion exchanger are eluted in the order of size starting with the oligosaccharide of the smallest size. Based on this, it is considered that the binding power of the HA oligosaccharides to the strongly basic anion exchanger is substantially proportional to the size of HA oligosaccharides, and as a result, it is considered that the oligosaccharides are eluted in the order of binding power starting with the oligosaccharide of the smallest power (the oligosaccharide of the smallest size). The fraction of the present invention is provided for the first time by utilizing such binding and elution characteristics of the strongly basic anion exchanger and HA oligosaccharides. According to this method, HA oligosaccharides of various sizes can be separated in a simple manner by one column operation with high resolution to efficiently produce a HA oligosaccharide fraction of high purity comprising HA oligosaccharide of a substantially uniform size and not substantially containing HA oligosaccharides of other sizes and others impurities (fraction of the present invention).

The HA oligosaccharides contained in the fraction of the present invention preferably has a size selected from sizes of 4 to 20 saccharides, more preferably selected from sizes of 4 to 16 saccharides, still more preferably selected from sizes of 4 to 14 saccharides, and it is most preferably a size of 4 saccharides.

The fraction of the present invention obtained as described above may be subjected again to the aforementioned chromatography step. Further, it may also be subjected to concentration, desalting and other treatments.

The form of the fraction of the present invention for storage, distribution etc. is not particularly limited, and it may be in the form of solution, frozen product, lyophilized product or the like.

Further, the HA oligosaccharides in the fraction of the present invention may be in the form of salt, and may be in an ionized state. Examples of the salt include, for example, salts with an inorganic base such as alkali metal salts (sodium salt, lithium salt, potassium salt etc.), alkaline earth metal salts and ammonium salts and salts with an organic base such as diethanolamine salts, cyclohexylamine salts, amino acid salts, galactosamine salts and glucosamine salts. Among these, alkali metal salts are preferred, and sodium salts are particularly preferred. When the fraction of the present invention is used for the drug of the present invention explained below, pharmaceutically acceptable salts among these salts can be used. Also in this case, sodium salts are particularly preferred.

The fraction of the present invention obtained as described above is characterized by satisfying all the physicochemical properties defined in the following (1) to (6). The numeric values and so forth mentioned in the physicochemical properties mentioned below may somewhat change with conditions of tests or experiments, environment, equipments used, degree of skill of laboratory worker, other factors and so forth. Therefore, the numeric values must not be construed to be strictly limited to the numeric values themselves, and should be construed in consideration of existence of small differences in measurement results due to experimental conditions etc. (differences of numeric values acceptable from a commonsense standpoint of those skilled in the art, differences of numeric values in such a degree that they can be recognized as those of the same fraction by those skilled in the art).

(1) If the fraction is analyzed by the detection methods mentioned in the following (a) and (b) using gel filtration chromatography, the fraction shows a substantially single peak in both of the methods, and the peaks have peak areas defined in the following (a) and (b).

(a) If the detection is performed based on absorbance at 210 nm, a relative ratio of peak area of the substantially single peak to the sum of peak areas of total HA oligosaccharides in the fraction is 85% or more. This relative ratio of peak area is preferably 90% or more, more preferably 95% or more.

(b) If the detection is performed by using a differential refractometer (also abbreviated as "RI" hereinafter), a relative ratio of peak area of the substantially single peak to the sum of peak areas of total HA oligosaccharides in the fraction is 98% or more.

This physicochemical property indicates that the fraction is constituted by HA oligosaccharide molecules of a substantially uniform size. It also suggests that the fraction does not substantially contain other impurities.

In this specification, the expression of "substantially single (substantially uniform)" does not mean "completely single (completely uniform)", but means that "recognized to be single (uniform) by those skilled in the art". For example, it is generally difficult to obtain a fraction of oligosaccharide of a large size not containing oligosaccharides of other sizes at all, and this is a common sense in this technical field. Therefore, in chromatography analysis, mass spectrometry analysis or the like of a fraction of oligosaccharide of a large size, even if, in addition to a major peak of the concerned oligosaccharide, a small peak of oligosaccharide of another size is observed, it is usually recognized as a substantially single peak by taking the sizes of oligosaccharides into consideration. Therefore, in such a case, it can be considered "substantially single peak".

(2) If the fraction is analyzed based on absorbance at 210 nm by using anion exchange chromatography, the fraction shows a substantially single peak, and a relative ratio of peak area of the substantially single peak to the sum of peak areas of total HA oligosaccharides in the fraction is 90% or more. This relative ratio of peak area is preferably 95% or more.

This physicochemical property indicates that the fraction is constituted by HA oligosaccharide molecules having substantially uniform valence of charge, i.e., homogenous HA oligosaccharides. It also suggests that the fraction does not substantially contain other impurities.

The HA oligosaccharide molecules regularly contain carboxyl groups, for example, as shown in the formula (1), and these groups are ionized and converted into —$COO^-$ ions in a solution. Therefore, it can be said that the number of the —$COO^-$ ions contained in HA oligosaccharide molecules of a constant size is constant. Therefore, a substantially uniform valence of charge of HA oligosaccharides constituting the fraction also indicate that the fraction is constituted by HA oligosaccharide of a substantially uniform size.

(3) If oligosaccharides in the fraction are labeled with fluorescence and then analyzed by electrophoresis, a single band is detected, and bands of HA oligosaccharides of other sizes are not detected.

This indicates that it is also clarified that the fraction is constituted by HA oligosaccharide molecules of a substantially uniform size by analysis using a technique other than chromatography (electrophoresis), and supports the result of the chromatographic analysis. It also suggests that the fraction does not substantially contain other impurities.

(4) If a theoretical value of monoisotopic molecular weight or average molecular weight of HA oligosaccharides constituting the fraction is taken as 1, an actual value of the same measured for the fraction by mass spectrometry is 0.997 to 1.003 (relative value). This relative value is preferably in the range of 0.998 to 1.002, more preferably in the range of 0.999 to 1.001.

This also suggests that HA oligosaccharides constituting the fraction substantially consist of a single kind of oligosaccharides as also for the molecular weight (mass) and do not substantially contain other impurities.

(5) Respective differences between theoretical values (weight %) of carbon (C), hydrogen (H) and nitrogen (N) contents in HA oligosaccharides constituting the fraction and values of the same actually measured for the elements by elemental analysis of the fraction (weight %) are all in the range of ±1 (weight %).

If the HA oligosaccharides are in the form of sodium salt, it is preferred that the difference for sodium (Na) should be similarly in the range of ±1 (weight %).

This suggests that the HA oligosaccharides constituting the fraction is substantially uniform as also for the elemental composition and does not substantially contain other impurities.

(6) The fraction does not substantially contain proteins, DNA and endotoxins.

Although content of proteins in the fraction of the present invention can be measured by using a conventional method well known to those skilled in the art, the Lowry method is preferred. When proteins cannot be detected by this method (when the content is below the detection limit), it is determined that proteins are not substantially contained.

Although content of DNA in the fraction of the present invention can be measured by using a conventional method well known to those skilled in the art, the threshold method is preferred. When DNA cannot be detected by this method (when the content is below the detection limit), it is determined that DNA is not substantially contained.

Although content of endotoxins in the fraction of the present invention can be measured by using a conventional method well known to those skilled in the art, the Limulus test method using horseshoe crab amebocyte lysate is preferred. When endotoxins cannot be detected by this method (when the content is below the detection limit), it is determined that endotoxins are not substantially contained.

In the present specification, the expression of "do not substantially contain" does not mean "do not contain even one molecule" of impurity or the like, but means such a degree of content that those skilled in the art should recognize that impurities etc. are not contained (such a degree of content that impurities etc. cannot be detected by the methods mentioned above). If detection at a molecular level becomes possible in future thanks to progress of analytical techniques, the expression of "do not substantially contain" must be interpreted based on the descriptions of the present application.

Further, in one of preferred embodiments of the fraction of the present invention, HA oligosaccharide of a substantially uniform size have saturated glucuronic acid residues at the non-reducing ends, and in such a case, the fraction of the present invention has the property defined in the following (7).

(7) Results of $^1$H-NMR and $^{13}$C-NMR of the fraction do not contradict to the structure of HA oligosaccharide represented by the following formula (1).

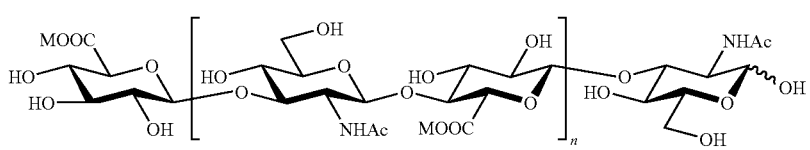

Formula (1)

(In the formula, n is an integer of 1 to 29, M represents a proton or a monovalent cation, and Ac represents acetyl group.)

This indicates that the HA oligosaccharides constituting the fraction are HA oligosaccharides represented by the aforementioned formula, and also suggests that the HA oligosaccharides are substantially uniform as also for the molecular structure and the fraction does not substantially contain other impurities.

<3> Drug of the Present Invention

The drug of the present invention is a drug containing the oligosaccharide of the present invention as an active ingredient.

The oligosaccharide of the present invention used as an active ingredient of the drug of the present invention, preferred embodiments thereof and so forth are as explained in the above <1>.

In particular, preferably used as the oligosaccharide of the present invention is an oligosaccharide having a size selected from sizes of 4 to 20 saccharides (HA tetrasaccharide to HA icosasaccharide), more preferably used is an oligosaccharide represented by the formula (2) wherein n is selected from integers of 1 to 9, and particularly preferably used is an oligosaccharide represented by the formula (1) wherein n is selected from integers of 1 to 9.

More preferably, an oligosaccharide of the present invention having a size selected from sizes of 4 to 16 saccharides (HA tetrasaccharide to HA hexadecasaccharide) is preferably used, an oligosaccharide represented by the formula (2) wherein n is selected from integers of 1 to 7 is more preferably used, and an oligosaccharide represented by the formula (1) wherein n is selected from integers of 1 to 7 is particularly preferably used.

Still more preferably, an oligosaccharide of the present invention having a size selected from sizes of 4 to 14 saccharides (HA tetrasaccharide to HA tetradecasaccharide) is preferably used, an oligosaccharide represented by the formula (2) wherein n is selected from integers of 1 to 6 is more preferably used, and an oligosaccharide represented by the formula (1) wherein n is selected from integers of 1 to 6 is particularly preferably used.

Among these, preferably used as the oligosaccharide of the present invention is an oligosaccharide of a size of 4 saccharides (HA tetrasaccharide), more preferably used is an oligosaccharide represented by the formula (2) wherein n is 1, and particularly preferably used is an oligosaccharide represented by the formula (1) wherein n is 1. By using HA tetrasaccharide, various superior pharmacological actions can be exerted.

Although the aforementioned formulas (1) and (2) represent an oligosaccharide of the present invention having a saturated glucuronic acid residue at the non-reducing end, an oligosaccharide of the present invention having an unsaturated glucuronic acid residue at the non-reducing end may be used for the drug of the present invention depending on the specific use of the drug of the present invention, and the preferred size thereof is as described above.

More preferably, the fraction of the present invention is used as an active ingredient of the drug of the present invention. The fraction of the present invention and preferred embodiments thereof used for the preparation of the drug are as described in the above section <2>. Further, the preferred sizes of HA oligosaccharides contained in the fraction of the present invention are the same as described above.

By using the fraction of the present invention, content of HA oligosaccharides in the drug of the present invention can be increased, and the drug of the present invention that does not substantially contain a substance of which contamination is not allowed as a drug can be produced.

The drug of the present invention can be prepared by a known method. Upon preparation of the drug, components usually used for drugs such as other pharmaceutically active ingredients, conventional stabilizers, emulsifiers, osmotic pressure regulators, pH regulators, buffers, isotonic agents, preservatives, soothing agents, colorants, excipients, binders, lubricants, disintegrating agents and so forth can be used, so long as such components do not adversely affect the HA oligosaccharides, which are the active ingredient of the drug of the present invention, and do not affect efficacy of the drug of the present invention.

In addition, although the drug of the present invention preferably contains the fraction of the present invention as an active ingredient, it is sufficient that the drug should contain at least an HA oligosaccharide having a size selected from sizes of 4 to 60 saccharides, since it contains such an HA oligosaccharide as an active ingredient, and the drug may contain an HA oligosaccharide of another molecular size or HA having a large size that cannot be referred to as oligosaccharide so long as it does not affect the efficacy of the drug of the present invention.

The drug of present invention is preferably a drug for use in promotion of Hsp expression, inhibition of cell death, inhibition of cell injury or protection of cell and tissue, and it can be any one of the following agents depending on the use.

[1] Hsp Expression Promoter

The term "promotion of expression" used in the present specification includes the meanings of both of "increasing of expression amount" and "enhancement of activity". Therefore, the term "heat shock protein expression promoter (Hsp expression promoter)" used in the present specification includes both of "an agent for increasing expression amount of heat shock protein (Hsp)" and "an agent for enhancing activity of Hsp".

(1) Administration Method, Dosage Form Etc. of Hsp Expression Promoter

When the drug of the present inventions is used as an Hsp expression promoter, an HA oligosaccharide consisting of 4 saccharides among HA oligosaccharides is particularly preferably used. Such an HA oligosaccharide exerts extremely superior Hsp expression promoting activity.

Although the administration method for the Hsp expression promoter is not particularly limited so long as the Hsp expression promoting action of HA oligosaccharide is exerted, examples thereof include, for example, injection (intravenous, intramuscular, subcutaneous, intracutaneous, intraperitoneal injections etc.), nasal administration, oral administration, transdermal administration, inhalation and so forth. An appropriate dosage form can be selected depending on the administration method, and there can be employed injections (solutions, suspensions, emulsions, solid agents for dissolution upon use etc.), tablets, capsules, solutions, granules, powders, liposomes, ointments, plasters, lotions, dermatologic pastes, patches, gels, suppositories, powders for external application, sprays, inhalation powders and so forth.

Although the content of HA oligosaccharide (especially HA tetrasaccharide) in the Hsp expression promoter is not also particularly limited, it is preferably 0.1 to 10% (w/v), for example, when the Hsp expression promoter is provided as an injection.

When the Hsp expression promoter is provided as an injection, for example, it may be in the form of any of solution, frozen preparation and lyophilized preparation. These may be filled and sealed in an appropriate container such as ampoule, vial and syringe for injection, distributed or stored as they are, and administered as an injection.

Although HA tetrasaccharide is particularly preferred as an active ingredient of the Hsp expression promoter as described above, HA oligosaccharides of other molecular sizes may be further contained. However, as is demonstrated by the examples described later, HA tetrasaccharide specifically exhibits particularly marked Hsp expression promoting action. Therefore, if the content of HA tetrasaccharide is increased, correspondingly higher effect can be obtained, and the dose may be decreased while the effect is maintained at the same level as HA saccharide of the other sizes. Thus, it is particularly preferred that the HA oligosaccharides contained in the Hsp expression promoter should substantially consist only of the tetrasaccharide, and it is desirable that HA oligosaccharides other than HA tetrasaccharide should not be added.

(2) Objectives of Administration of Hsp Expression Promoter Etc.

The Hsp expression promoter is expected to be effective against many diseases caused by cell injury or cell death for which preventive effect by Hsp is suggested, for example, ischemic diseases caused by angiostenoses or ischemia such as heart diseases (myocardial infarction etc.), renal tubular affections, circulatory affections, encephalopathies (apoplexy etc.) and nervous diseases), immunity-related diseases such as acquired immunodeficiency syndrome, affections of thymocyte caused by administration of immunosuppressive agent or anticancer agent, decrease of peripheral T cells and immune deficiency, inflammations such as hepatitis and ulcerative colitis, external injuries, bacterial infections, viral infections, Alzheimer's disease, diabetes mellitus, auxeses, Kawasaki disease, schizophrenia, fervescence, metabolic diseases, cancers and so forth.

Moreover, the Hsp expression promoter can be used not only for diseases caused by cell injury or cell death, but also for objectives for which cell or tissue protective action can be expected. In this respect, detailed explanation will be made in the section of the "cell and tissue protecting agent" described later.

A subjective animal to be administered with the Hsp expression promoter is preferably a vertebrate, especially a mammal, particularly preferably a human. Although the Hsp expression promoter can be administered for the purpose of prevention of those diseases or suppression of advance of those diseases (prevention of aggravation), amelioration or treatment of symptoms and so forth, it is preferably administered as a drug for prophylactic treatment.

The formulation amounts, doses for single administration, administration intervals and so forth of the HA oligosaccharides, especially HA tetrasaccharide, contained in the Hsp expression promoter are factors to be individually determined depending on the administration route, dosage form, purpose of use etc. of the promoter as well as specific symptoms, age, sex, body weight of patients, and they are not particularly limited. However, the clinical dose of HA tetrasaccharide may be, for example, 300 to 7500 mg per single administration for an adult. As for the administration interval of the Hsp expression promoter, it may be administered one time per day, or dividedly administered 2 to 3 times per day.

The Hsp expression promoter can be used also as a test reagent for an experiment concerning the stress protein expression promoting action.

[2] Cell Death Inhibitor

The cell death inhibitor constitutes one of the uses utilizing the Hsp expression promoting action. That is, since HA oligosaccharides (especially HA tetrasaccharide) not only exhibit the Hsp expression promoting action but also actually exhibit cell death inhibitory effect, it is used for the purpose of suppression of cell death.

Diseases for which the cell death inhibitor can be used are not particularly limited so long as they are diseases in which cell death can be inhibited by enhancement of Hsp expression. However, the diseases exemplified in the explanation of the Hsp expression promoter are preferably mentioned.

The animals to be administered with this cell death inhibitor, purpose of administration, formulation amounts, doses, administration intervals of the HA oligosaccharides (especially HA tetrasaccharide) are similar to those mentioned for the Hsp expression promoter.

[3] Cell Injury Inhibitor

Since the HA oligosaccharides (especially HA tetrasaccharide) also actually exhibit cell injury inhibitory action in addition to the Hsp expression promoting action, they are applied for the purpose of suppression of cell injury.

Diseases for which the cell injury inhibitor can be used are not particularly limited so long as they are diseases in which in which cell injury can be inhibited by enhancement of Hsp expression. However, the diseases exemplified in the explanation of the Hsp expression promoter are preferably mentioned.

The animals to be administered with this cell injury inhibitor, purpose of administration, formulation amounts, doses, administration intervals etc. of the HA oligosaccharides (especially HA tetrasaccharide) are similar to those mentioned for the Hsp expression promoter.

[4] Cell and Tissue Protecting Agent

Since the HA oligosaccharides (especially HA tetrasaccharide) also actually exhibit cell and tissue protecting action in addition to the Hsp expression promoting action, they are applied for the purpose of cell and tissue protection.

This cell and tissue protecting agent can be used for objectives for which cell and tissue protecting action by Hsp is expected. For example, it can be used for diseases for which cell or tissue protection is desired, protection of cells and tissues extracted out of organisms and so forth.

Examples of the diseases for which protection of cells or tissues is desired include peptic ulcers (gastric ulcer, duodenal ulcer etc.), gastritis, hepatopathies (hepatitis etc.), ulcerative colitis, ischemic heart diseases, myocardosis, apoplexy, cerebral infarction and so forth.

Specifically, this cell and tissue protecting agent is preferably used as the following agents.

(1) Antiulcer Agent and Antihepatopathic Agent

By using the aforementioned cell and tissue protecting agent as an agent for treatment of ulcer, it can be an antiulcer agent. By using the aforementioned cell and tissue protecting agent as an agent for treatment of hepatopathy, it can be an antihepatopathic agent. The "treatment" used in the present invention means administration of an agent to an animal with a disease of interest with a purpose of prevention, maintenance (prevention of aggravation), amelioration (improvement of symptoms) or cure of the disease, and the term "agent for treatment" means an agent used for such a treatment.

(2) IL-10 Production Promoter and IL-8 Production Inhibitor

The aforementioned cell and tissue protecting agent can also be used for treatment of diseases caused by decrease of IL-10, diseases for which promotion of IL-10 production is desired and so forth. By using the cell and tissue protecting agent as an agent for promoting IL-10 production, it can be an IL-10 production promoter.

The aforementioned cell and tissue protecting agent can also be used for treatment of diseases caused by increase of IL-8, diseases for which inhibition of IL-8 production is desired and so forth. By using the cell and tissue protecting agent as an agent for inhibiting IL-8 production, it can be an IL-8 production inhibitor.

Animals that can be objectives of these agents, purposes of administration thereof and so forth are similar to those mentioned in the explanation of the Hsp expression promoter.

(3) Organ Preservation Agent

The aforementioned cell and tissue protecting agent can also be used for the purpose of protecting cells and tissues extracted out of organisms and so forth. By using the cell and tissue protecting agent as an agent for preservation of cells and tissues extracted out of organisms, it can be, for example, an organ preservation agent. Specifically, by perfusing an organ removed for transplantation (liver, kidney, heart, lung etc.) with the organ preservation agent, or storing or maintaining such an organ in the organ preservation agent, cell or tissue affections of such an organ (edema, cell death etc.) can be inhibited.

The formulation amounts, doses for single administration (use), administration intervals of the HA oligosaccharides contained in the organ preservation agent can be individually determined depending on specific situations of administration such as administration route (method of use), dosage form, purpose of use and so forth.

For example, when the cell and tissue protecting agent is administered to a human as an antiulcer agent, antihepatopathic agent, IL-10 production promoter or IL-8 production inhibitor, the clinical dose may be 120 to 6000 mg for single dose for an adult as amount of HA oligosaccharides (especially HA tetrasaccharide).

When the cell and tissue protecting agent is used for the purpose of protecting cells or tissues extracted out of an organism, it may be formulated as a liquid preparation, perfusion, solid preparation for dissolution upon use or the like. When it is used as the organ preservation agent, the formulation amounts of the HA oligosaccharides (especially HA tetrasaccharide) and so forth may be individually determined depending on specific conditions such as size of organ to be stored or maintained, preservation time and temperature.

Although the concentration of the HA oligosaccharide (especially HA tetrasaccharide) in the cell and tissue protecting agent is not also particularly limited, when it is provided as an injection (solution) or a liquid preparation for organ preservation, it may be preferably 1 ng/mL to 1 mg/mL.

When the cell and tissue protecting agent is provided as an injection or a liquid preparation, it may be in the form of solution, frozen product, lyophilized product or the like. These may be filled and sealed in an appropriate container such as ampoule, vial, syringe for injection and bottle, distributed or stored as they are, and used as an injection or liquid preparation.

The present invention also provides, in addition to the agents mentioned above, a method for promoting Hsp expression, inhibiting cell death, inhibiting cell injury, or protecting cell and tissue (e.g., preserving an organ, treating an ulcer, treating a hepatopathy, promoting IL-10 production or inhibiting IL-8 production) in an objective of application such as cells and biological tissues, which comprises allowing the HA oligosaccharide (especially HA tetrasaccharide) to act on the object of the application in vitro or in vivo.

BRIEF EXPLANATION OF THE DRAWINGS

FIG. 13 shows an elution curve of HA48 in anion exchange chromatography. The ordinate and abscissa have the same meanings as in FIG. 7.

FIG. 14 shows an elution curve of HA50 in anion exchange chromatography. The ordinate and abscissa have the same meanings as in FIG. 7.

FIG. 15 shows an elution curve of HA52 in anion exchange chromatography. The ordinate and abscissa have the same meanings as in FIG. 7.

FIG. 16 shows results of electrophoresis of fluorescence-labeled oligosaccharides.

FIG. 22 shows mass spectra of HA48 (upper graph), HA50 (middle graph) and HA52 (lower graph).

FIG. 25 shows $^{13}$C-NMR spectrum of HA4.
FIG. 26 shows $^1$H-NMR spectrum of HA6.
FIG. 31 shows $^{13}$C-NMR spectrum of HA10.
FIG. 36 shows $^1$H-NMR spectrum of HA16.

FIG. 41 shows activation of HSF1 by HA tetrasaccharide after heat shock.

FIG. 46 shows decrease of TUNEL stained cell number obtained with HA tetrasaccharide.

FIG. 47 shows cell and tissue affection inhibitory effect of HA tetrasaccharide.

FIG. 49 shows hepatopathy inhibitory effect (GOT activity) of HA tetrasaccharide.

BEST MODE FOR CARRYING OUT THE INVENTION

Figure 1:
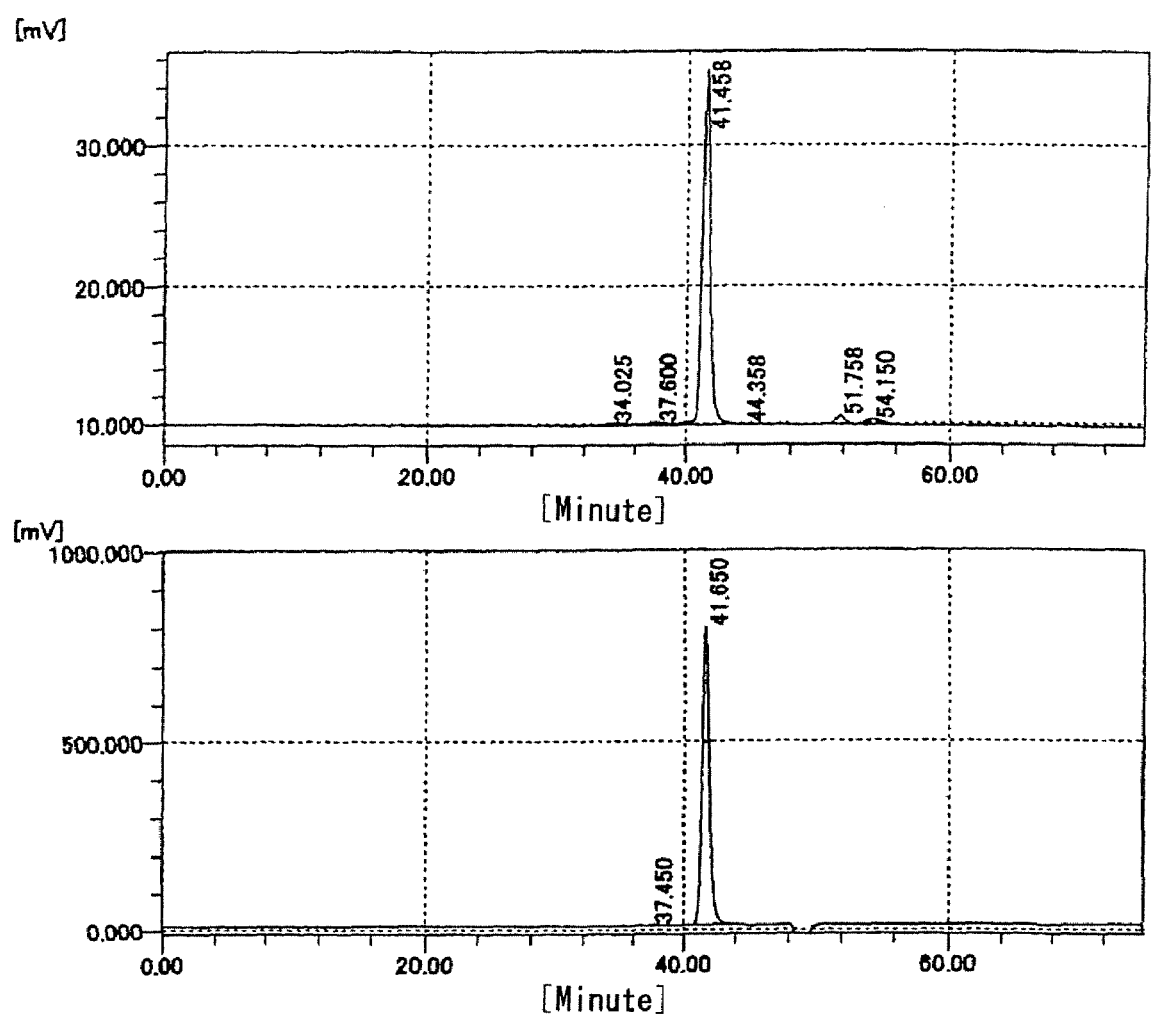
FIG. 1 shows an elution curve of HA4 in gel filtration chromatography. The ordinate of the upper graph represents absorbance at 210 nm, and the ordinate of the lower graph represents absorbance of RI. Further, each abscissa represents elution time.
Figure 2:
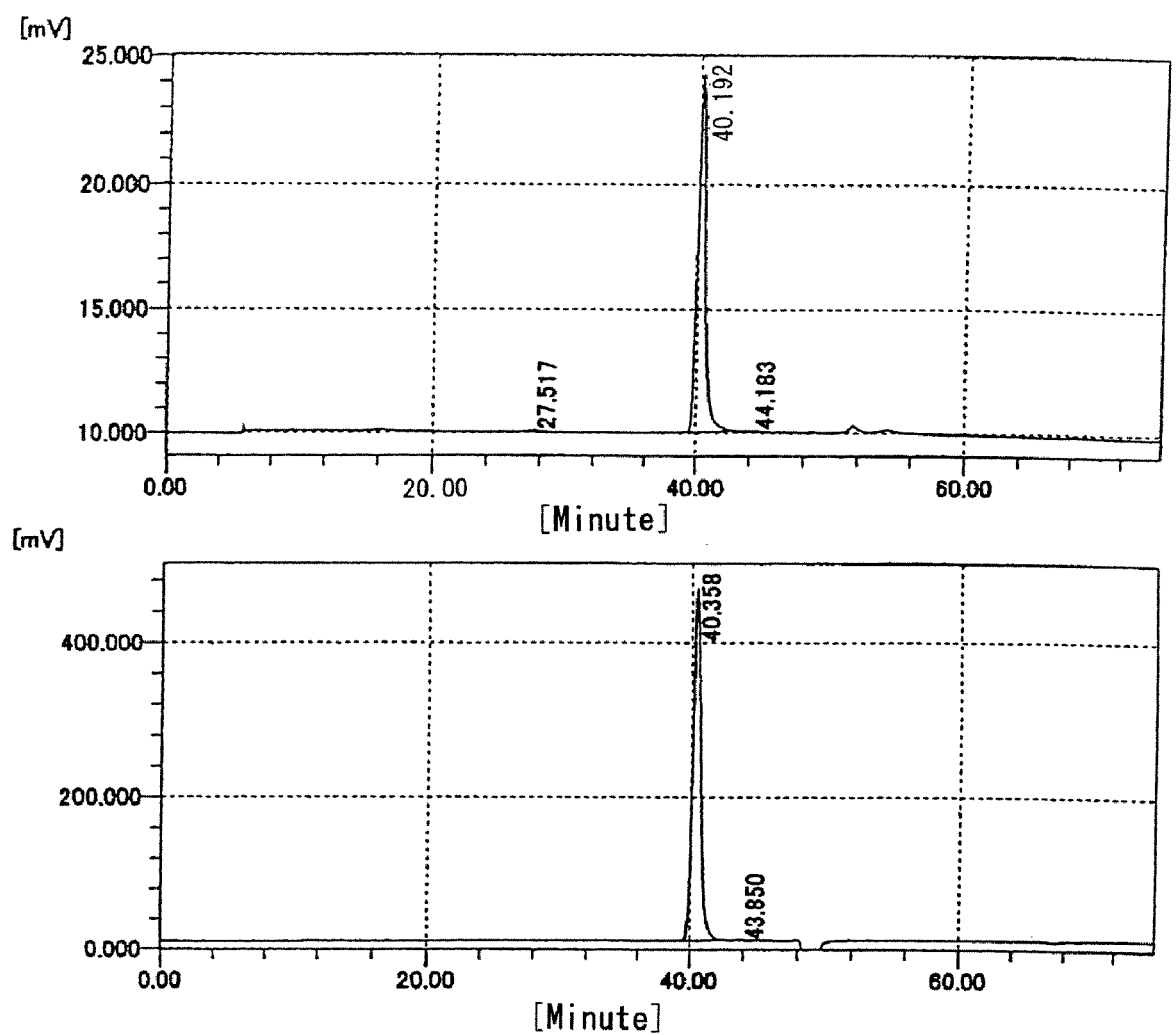
FIG. 2 shows an elution curve of HA6 in gel filtration chromatography. The ordinates and abscissas have the same meanings as in FIG. 1.
Figure 3:
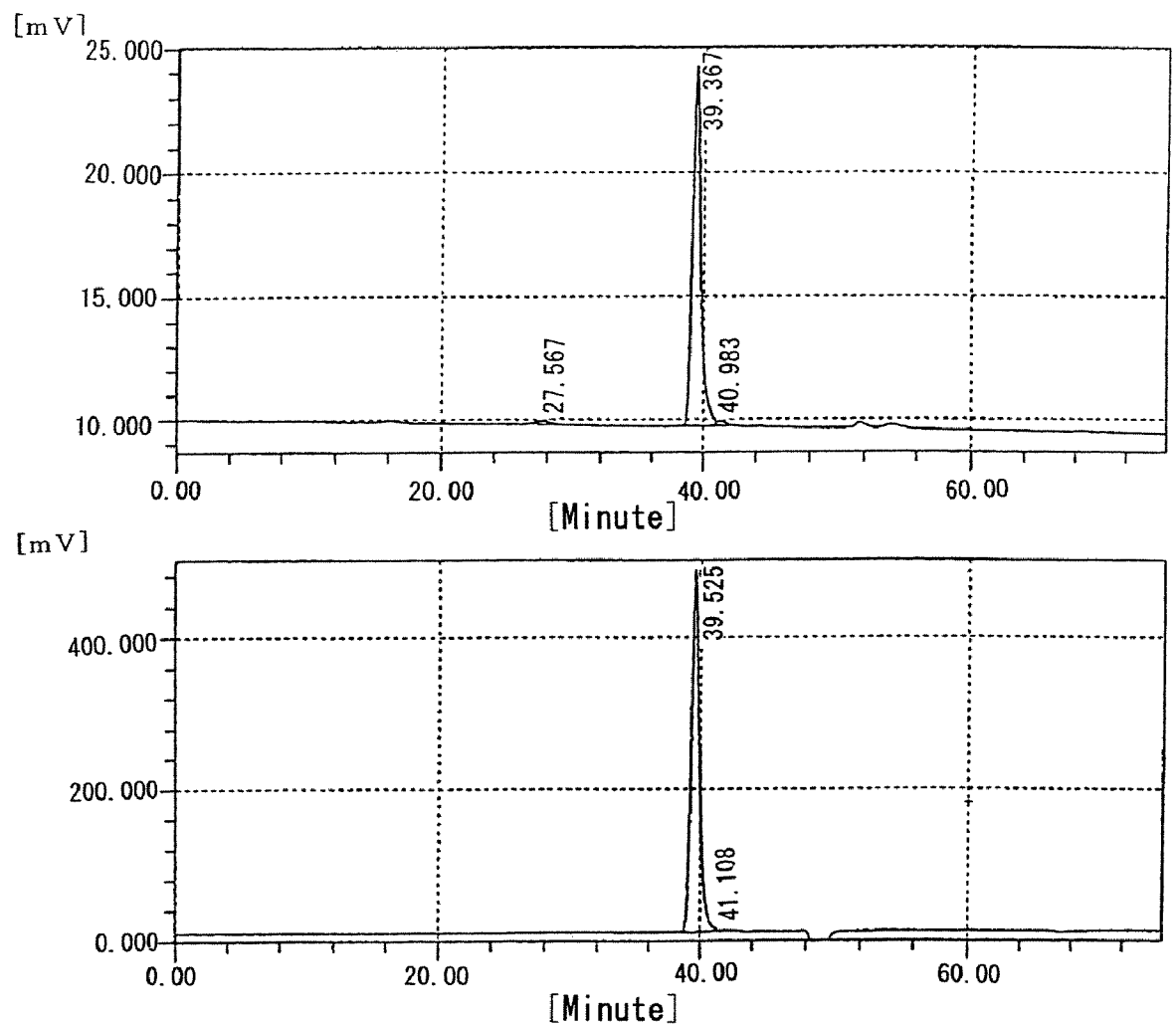
FIG. 3 shows an elution curve of HA8 in gel filtration chromatography. The ordinates and abscissas have the same meanings as in FIG. 1.
Figure 4:
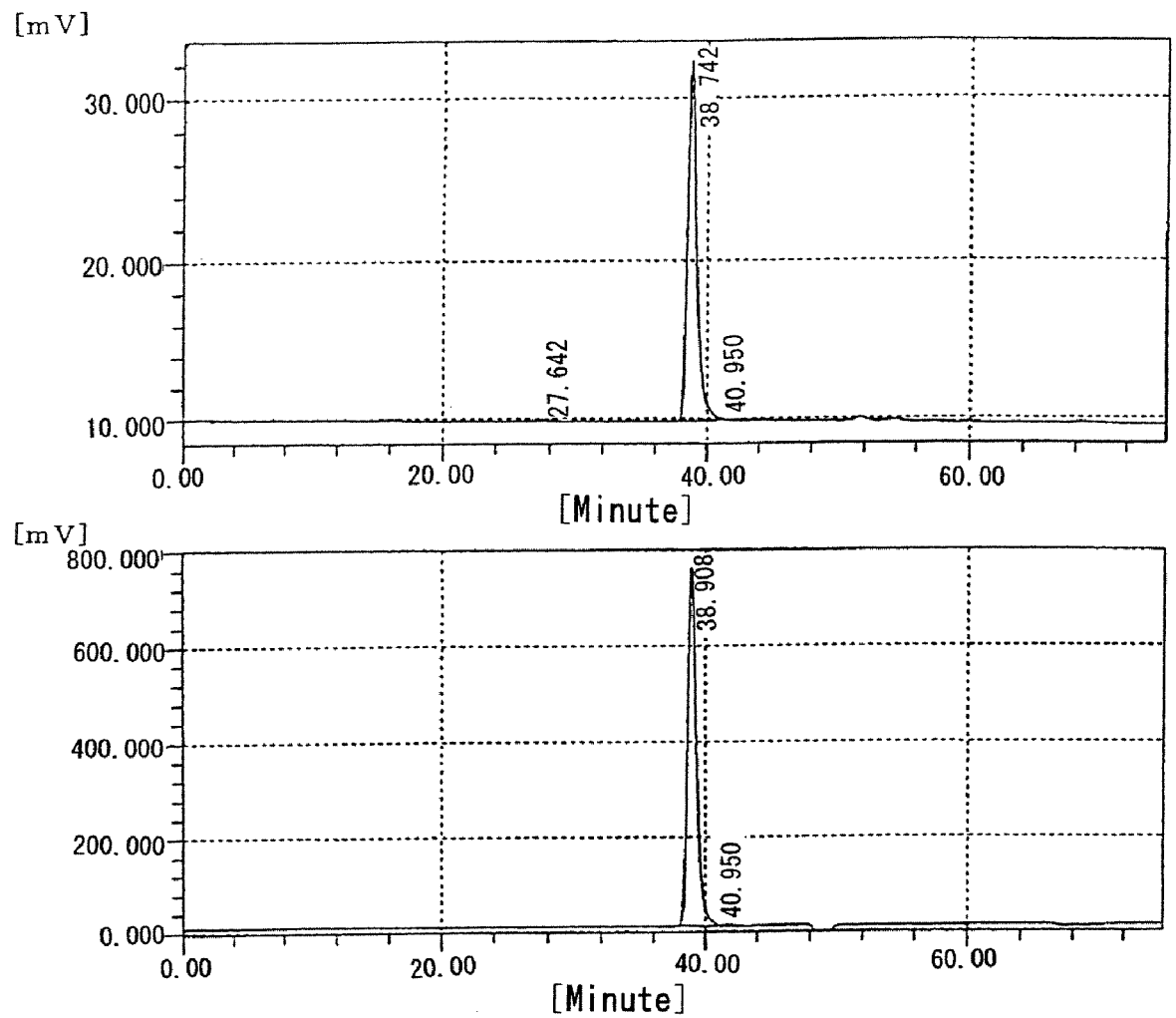
FIG. 4 shows an elution curve of HA10 in gel filtration chromatography. The ordinates and abscissas have the same meanings as in FIG. 1.
Figure 5:
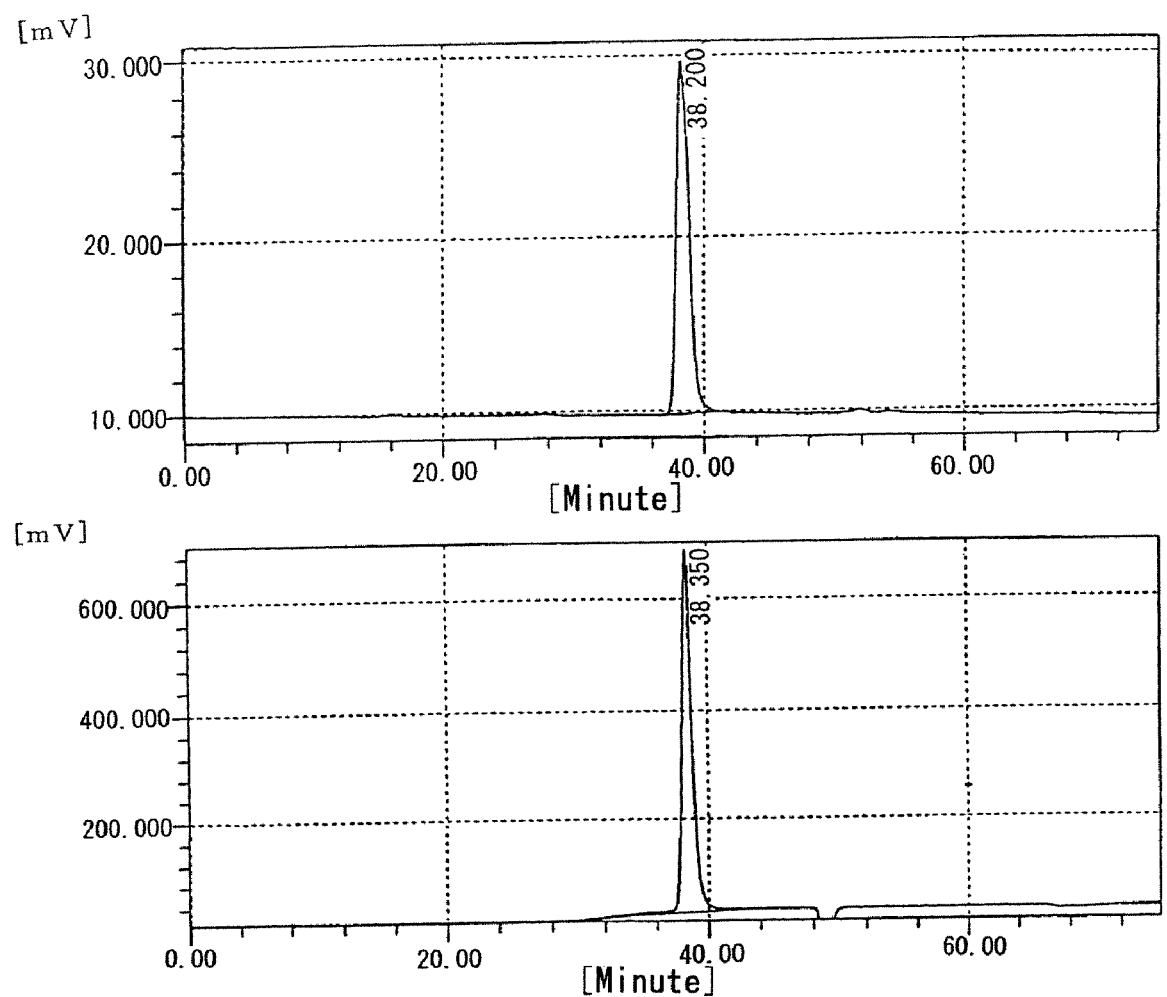
FIG. 5 shows an elution curve of HA12 in gel filtration chromatography. The ordinates and abscissas have the same meanings as in FIG. 1.
Figure 6:
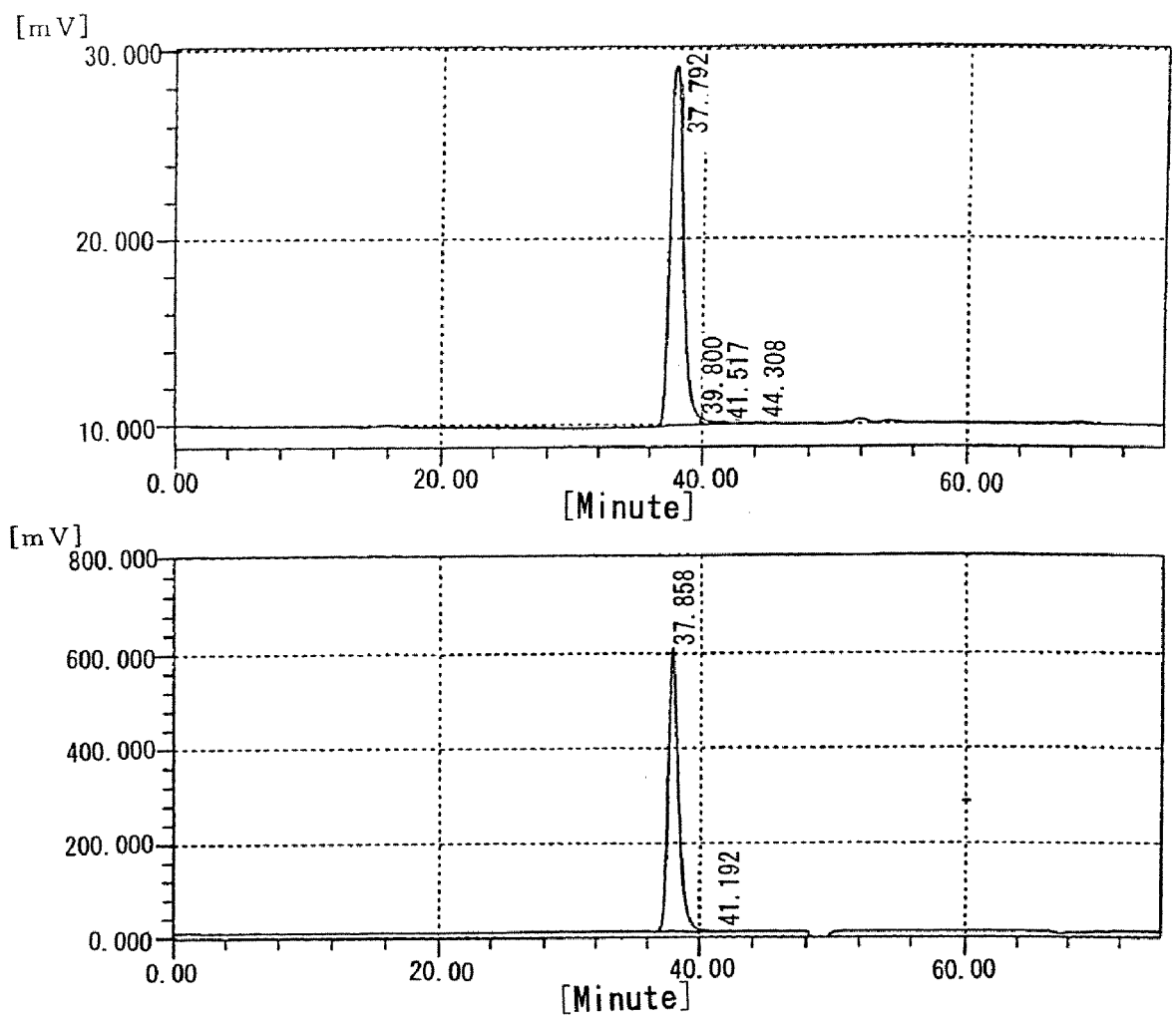
FIG. 6 shows an elution curve of HA14 in gel filtration chromatography. The ordinates and abscissas have the same meanings as in FIG. 1.
Figure 7:
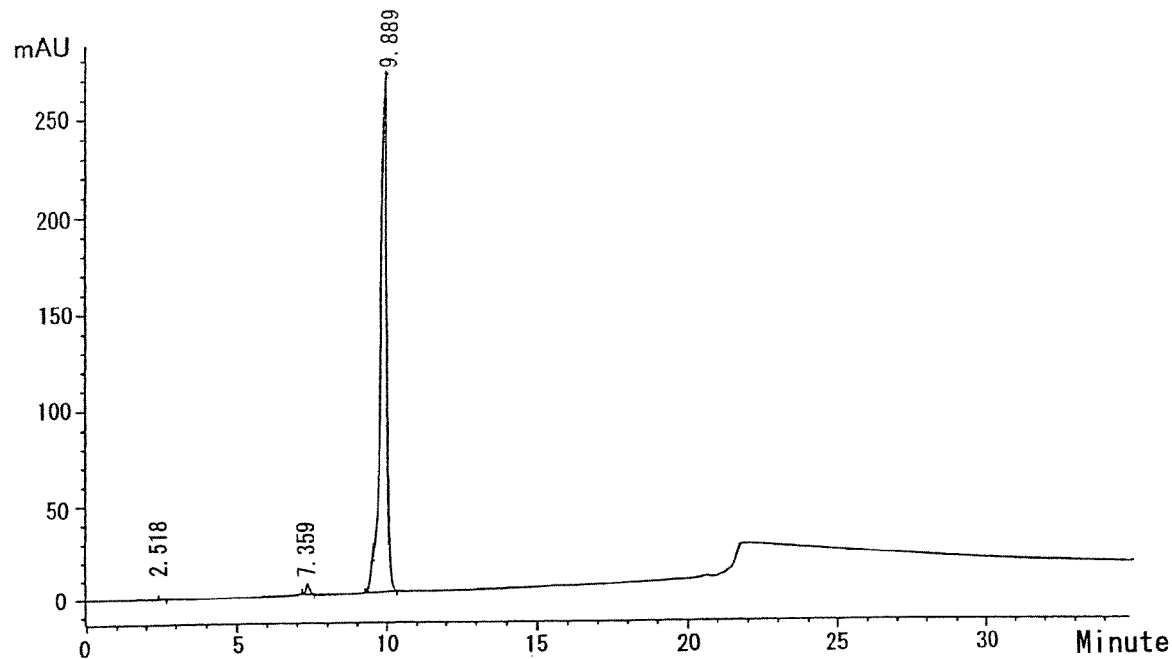
FIG. 7 shows an elution curve of HA4 in anion exchange chromatography. The ordinate represents absorbance at 210 nm, and the abscissa represents elution time.
Figure 8:
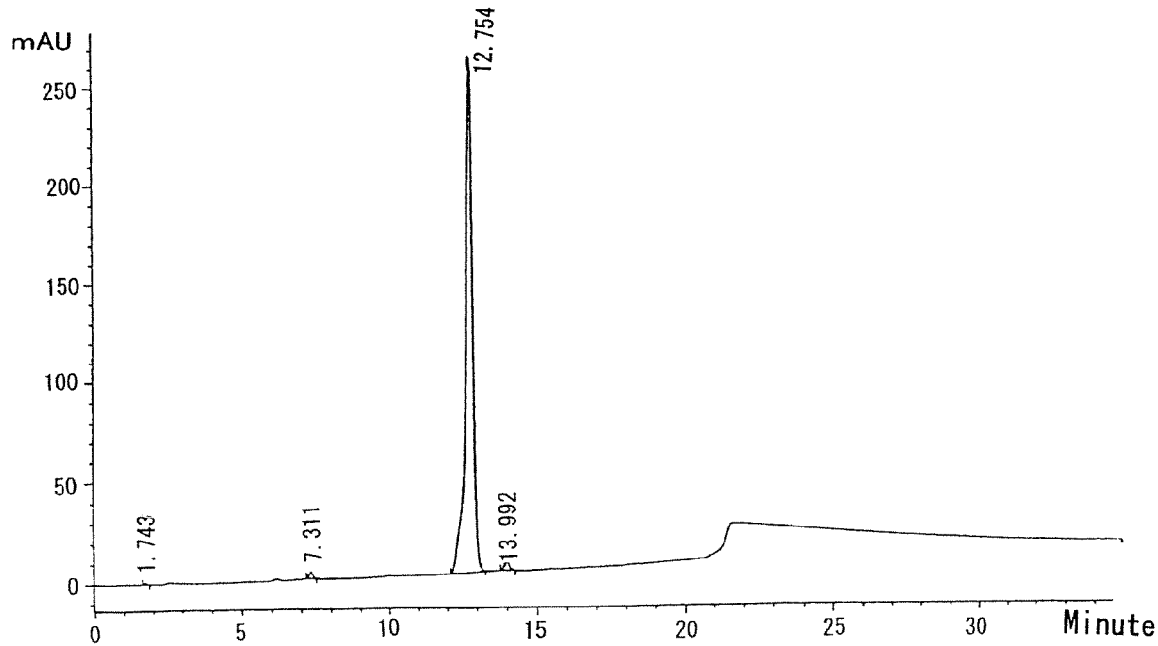
FIG. 8 shows an elution curve of HA6 in anion exchange chromatography. The ordinate and abscissa have the same meanings as in FIG. 7.
Figure 9:
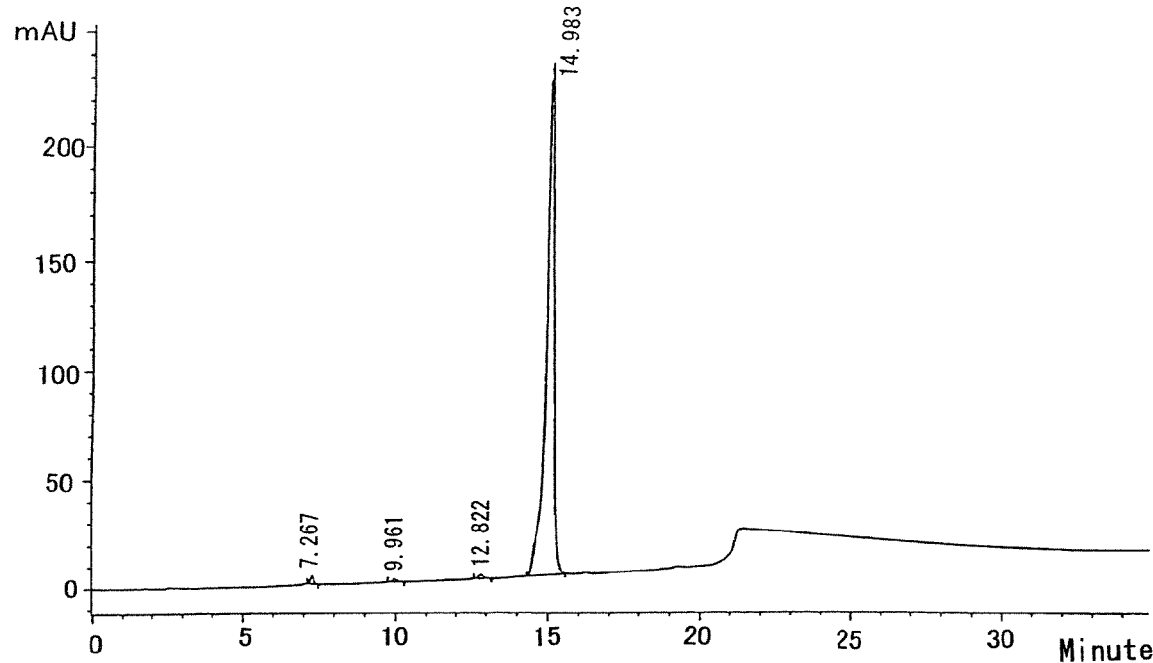
FIG. 9 shows an elution curve of HA8 in anion exchange chromatography. The ordinate and abscissa have the same meanings as in FIG. 7.
Figure 10:
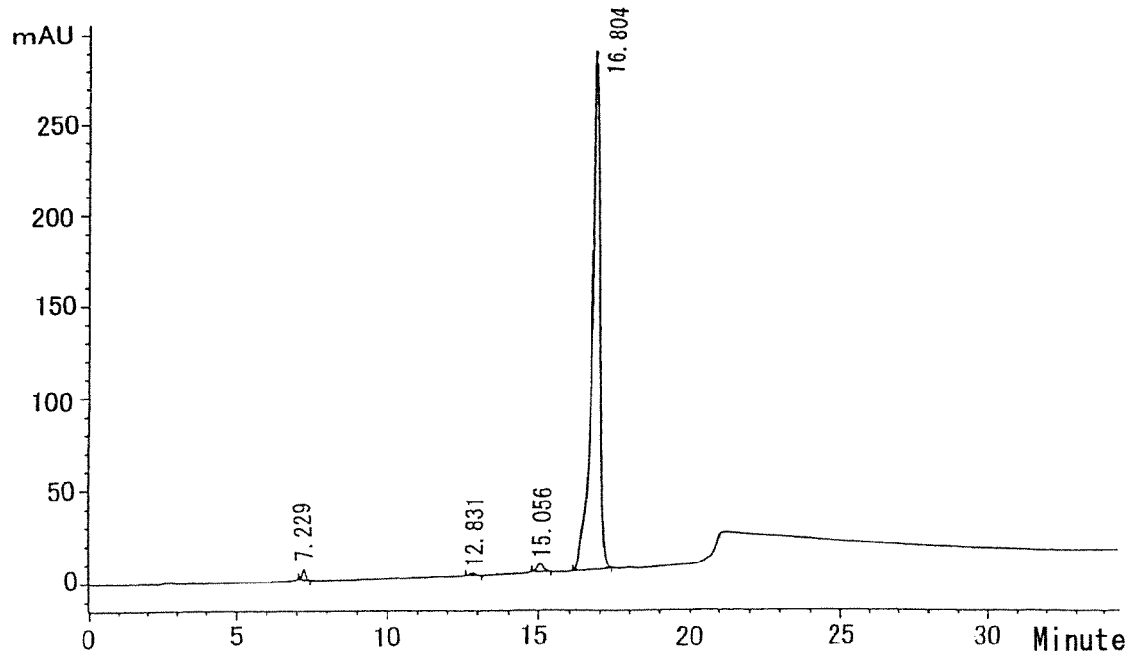
FIG. 10 shows an elution curve of HA10 in anion exchange chromatography. The ordinate and abscissa have the same meanings as in FIG. 7.
Figure 11:
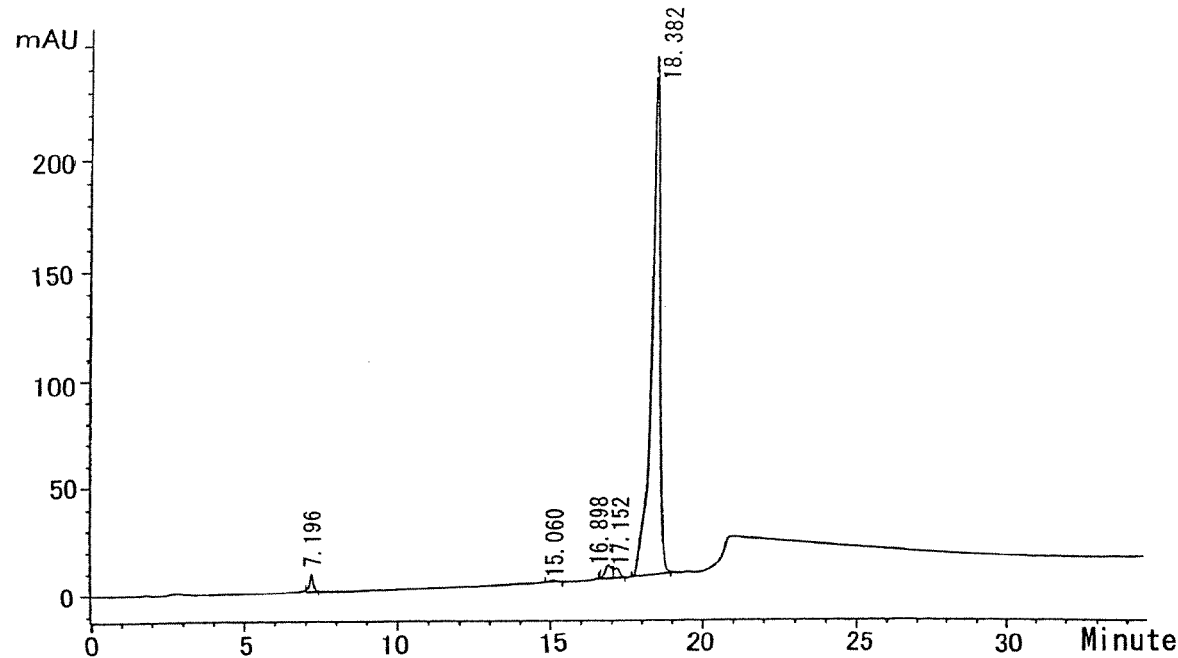
FIG. 11 shows an elution curve of HA12 in anion exchange chromatography. The ordinate and abscissa have the same meanings as in FIG. 7.
Figure 12:
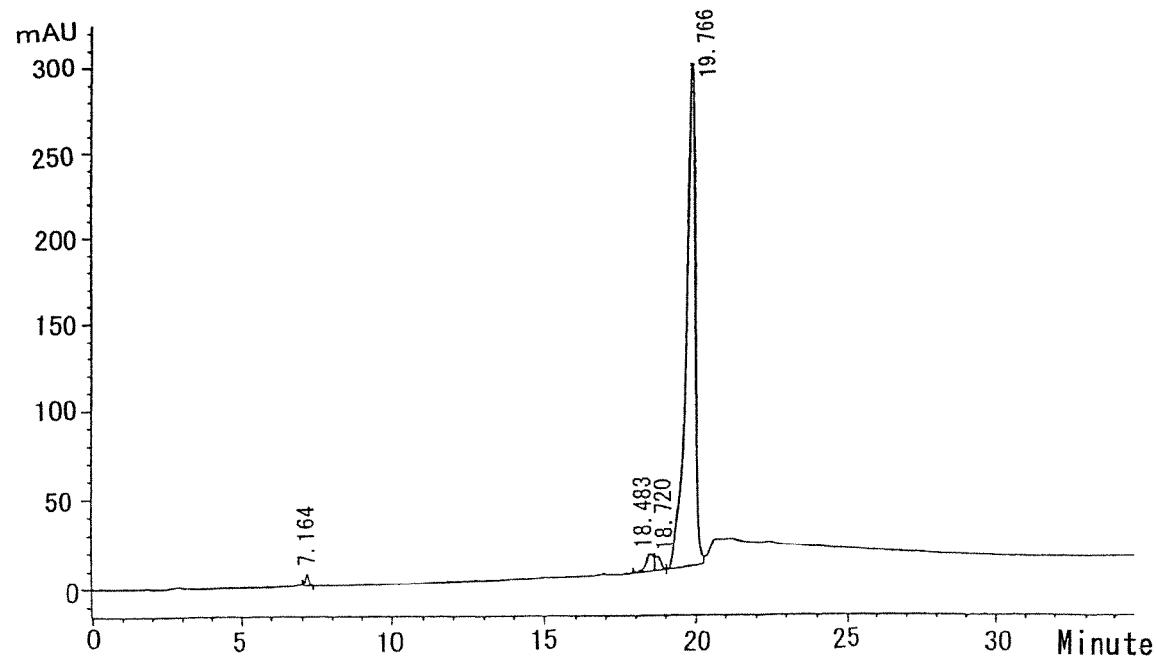
FIG. 12 shows an elution curve of HA14 in anion exchange chromatography. The ordinate and abscissa have the same meanings as in FIG. 7.
Figure 1:
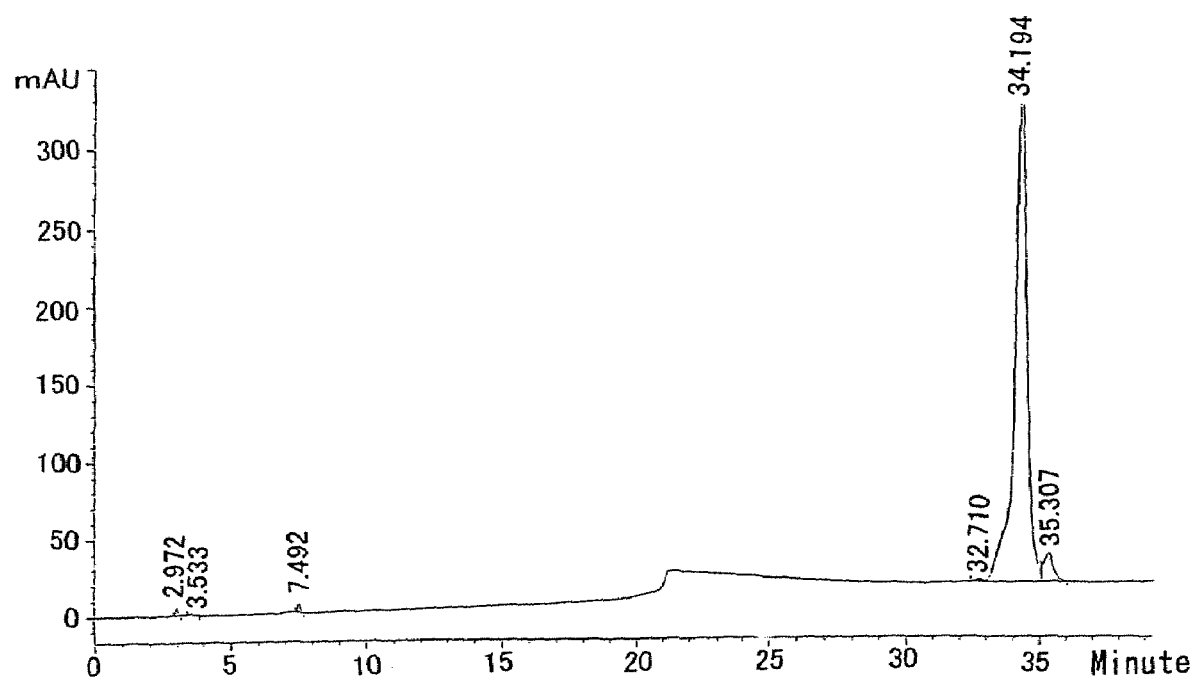
Figure 1:
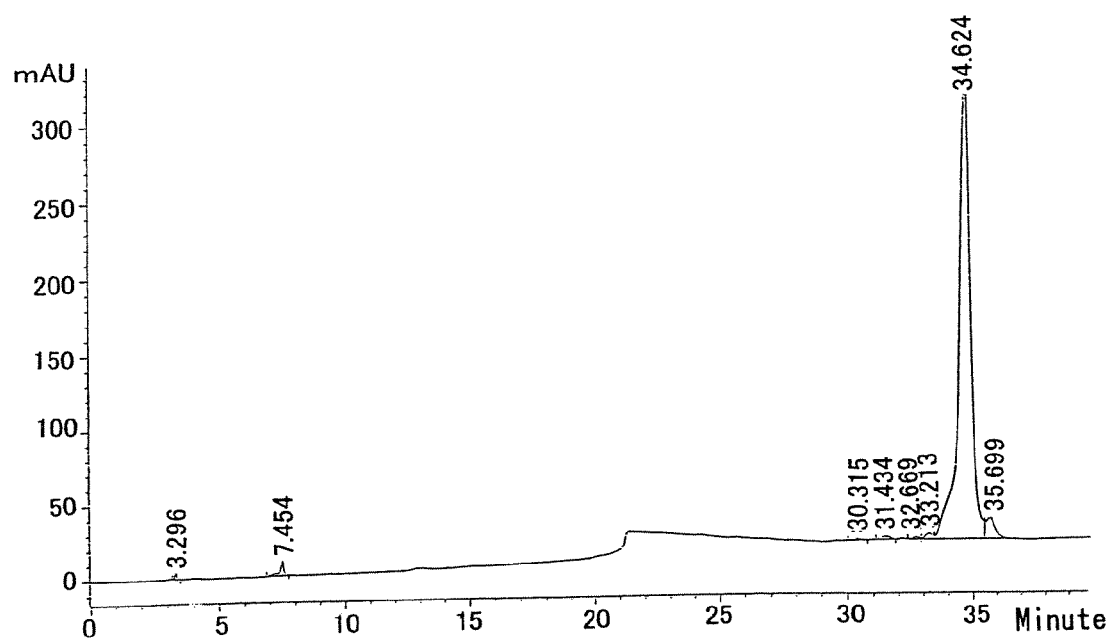
Figure 1:
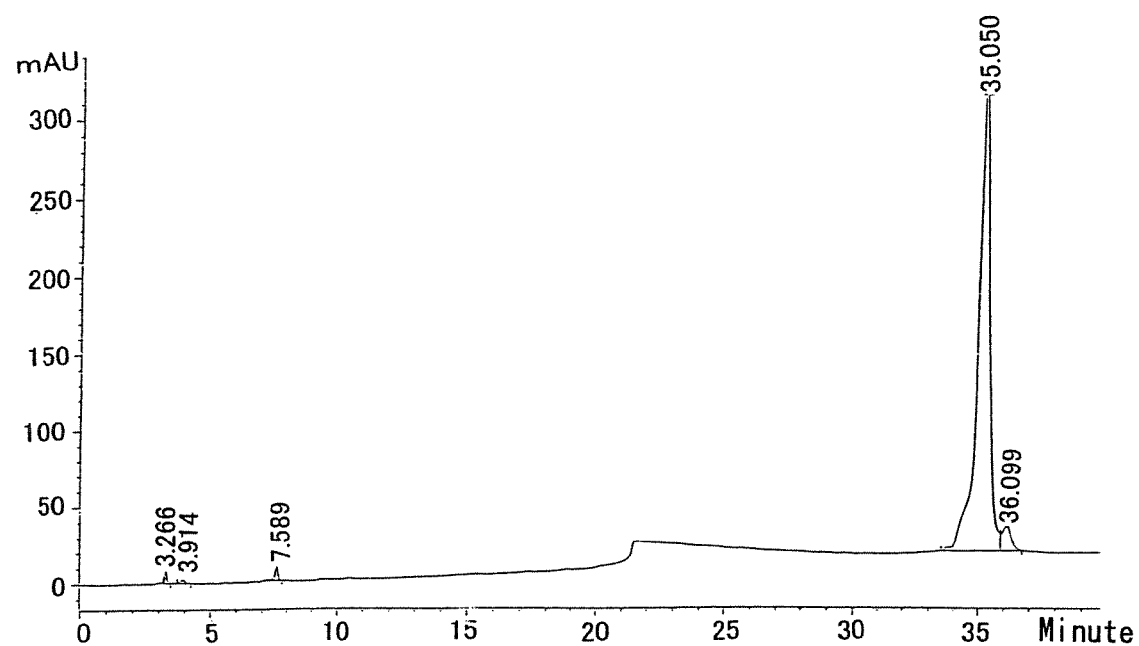
Figure 1:
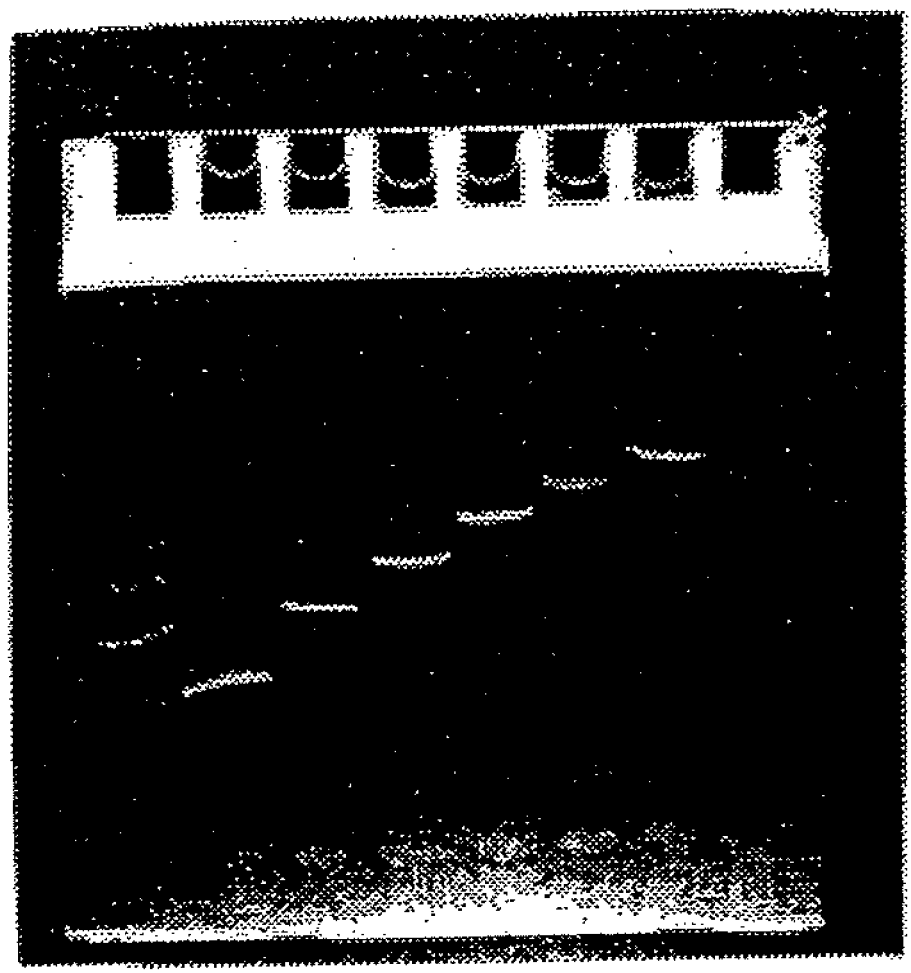
Figure 17:
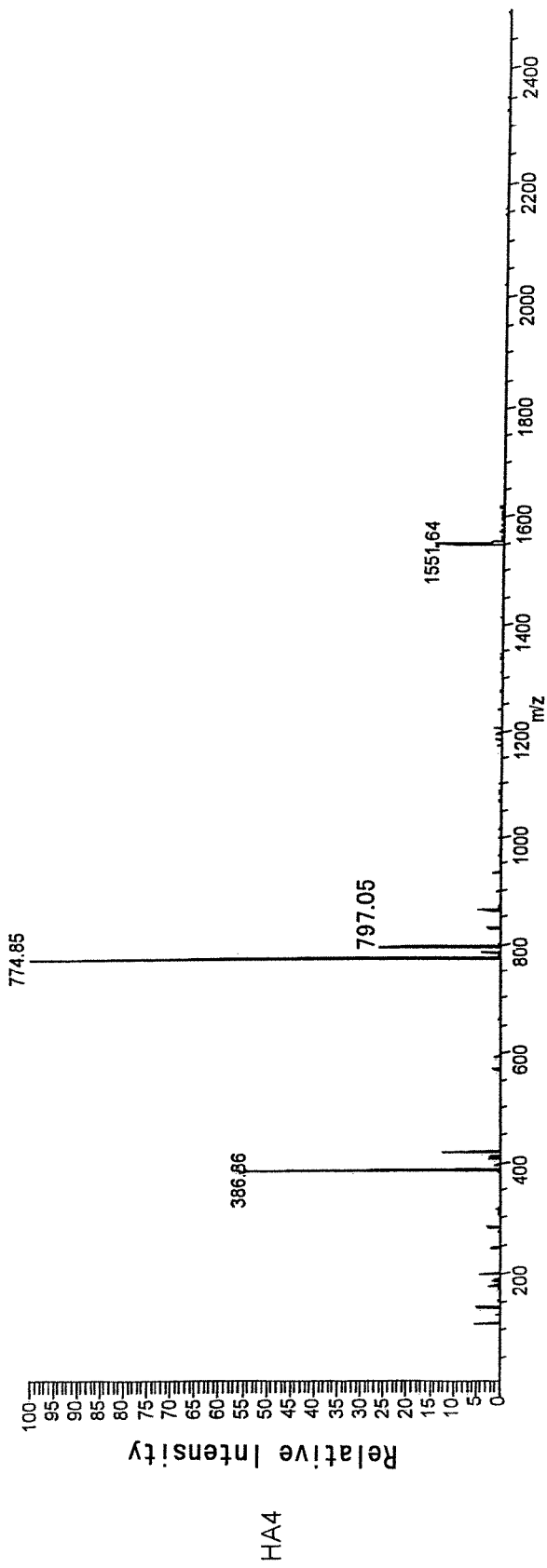
FIG. 17 shows mass spectrum of HA4 (Lot 1).
Figure 18:
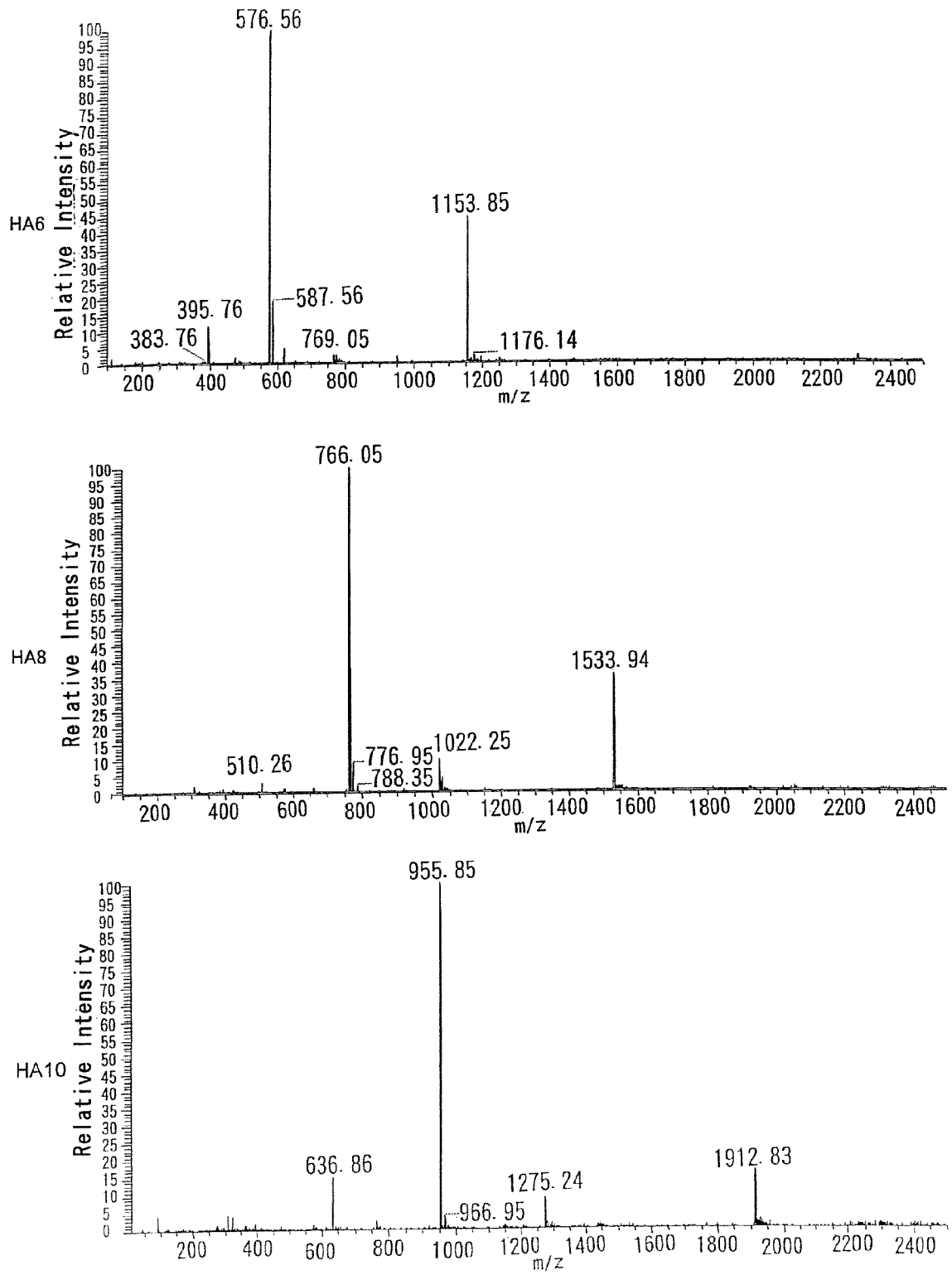
FIG. 18 shows mass spectra of HA6 (upper graph), HA8 (middle graph) and HA10 (lower graph).
Figure 19:
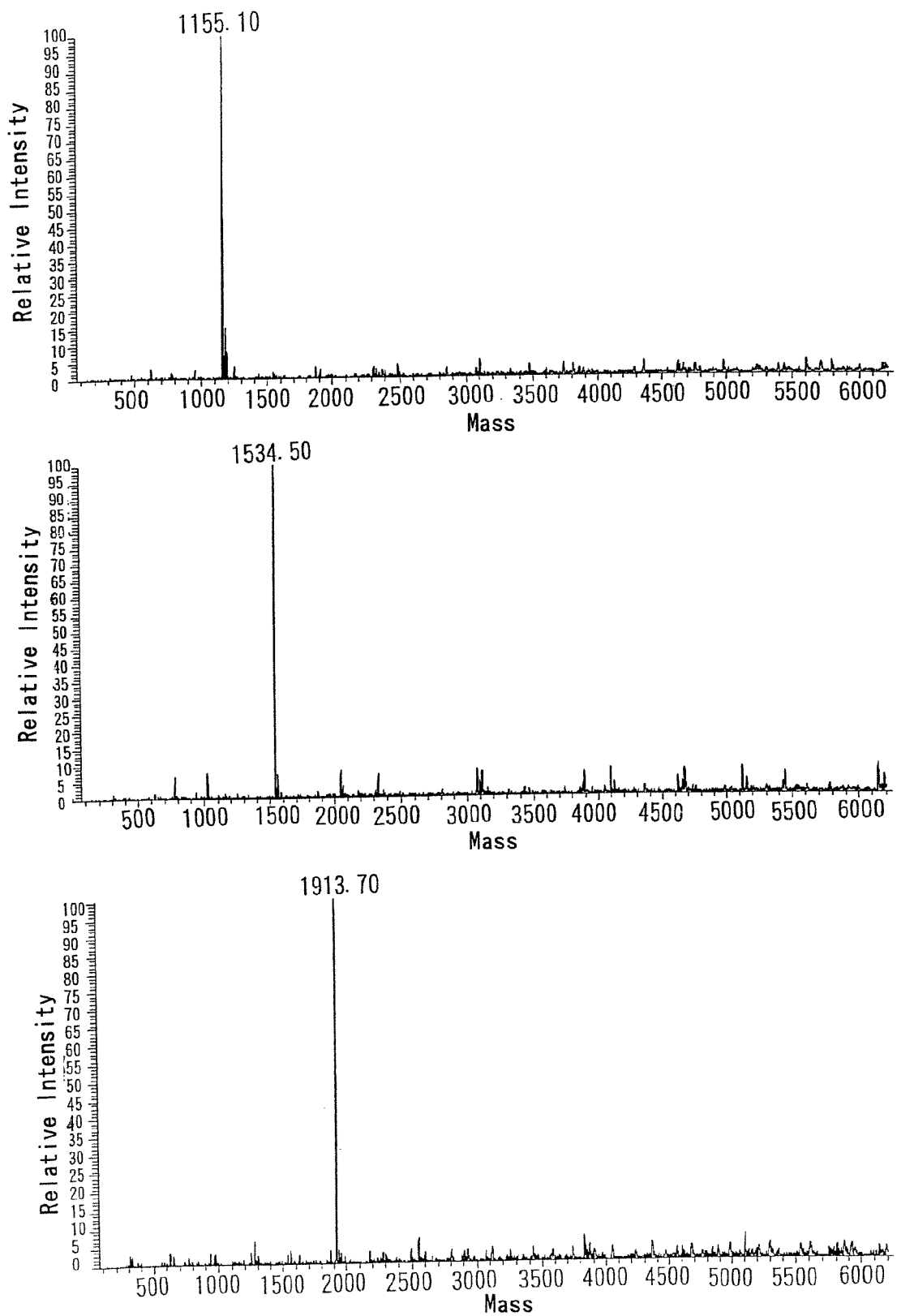
FIG. 19 shows results of deconvolution of HA6 (upper graph), HA8 (middle graph) and HA10 (lower graph).
Figure 20:
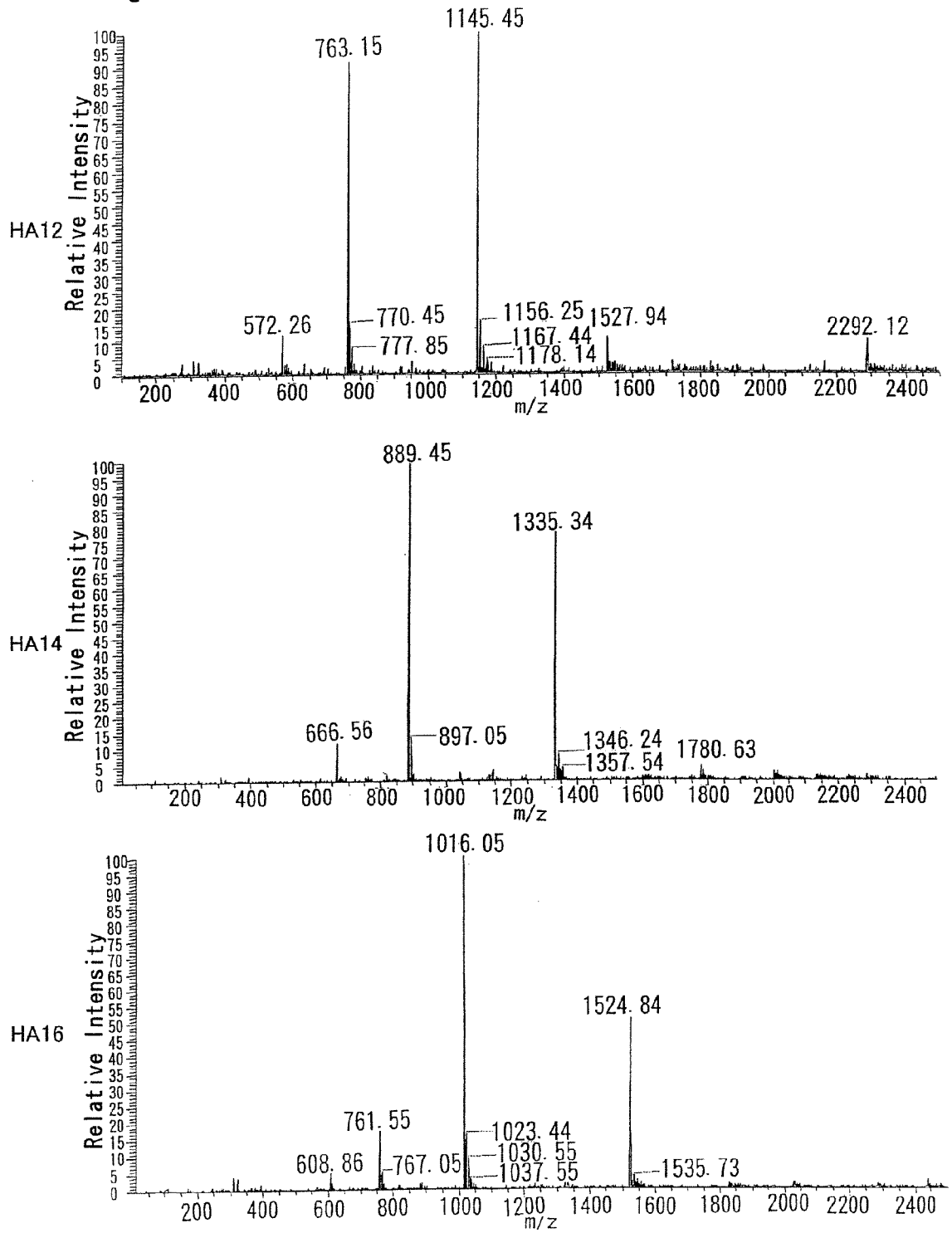
FIG. 20 shows mass spectra of HA12 (upper graph), HA14 (middle graph) and HA16 (lower graph).
Figure 21:
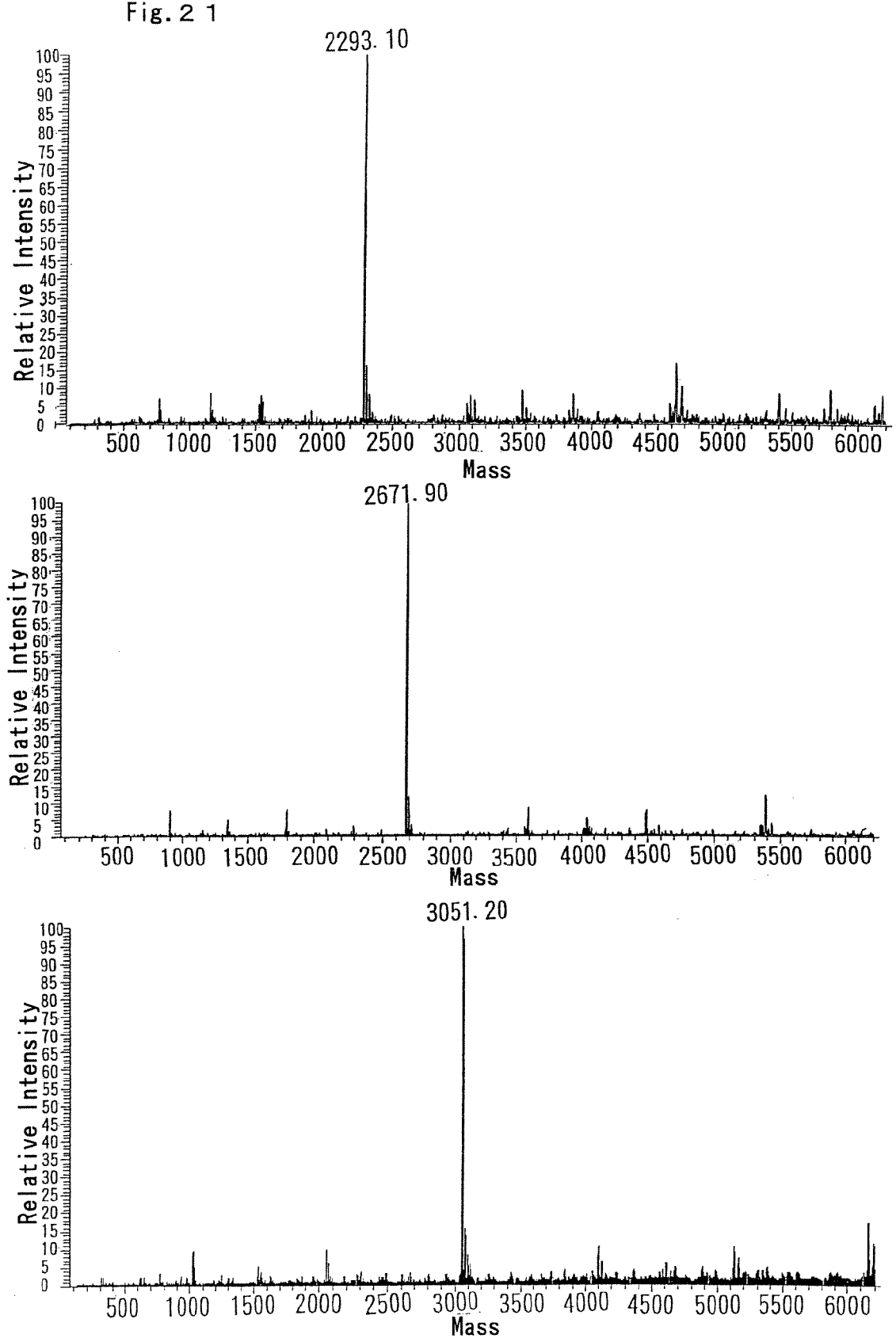
FIG. 21 shows the result of deconvolution of HA12 (upper graph), HA14 (middle graph) and HA16 (lower graph).
Figure 23:
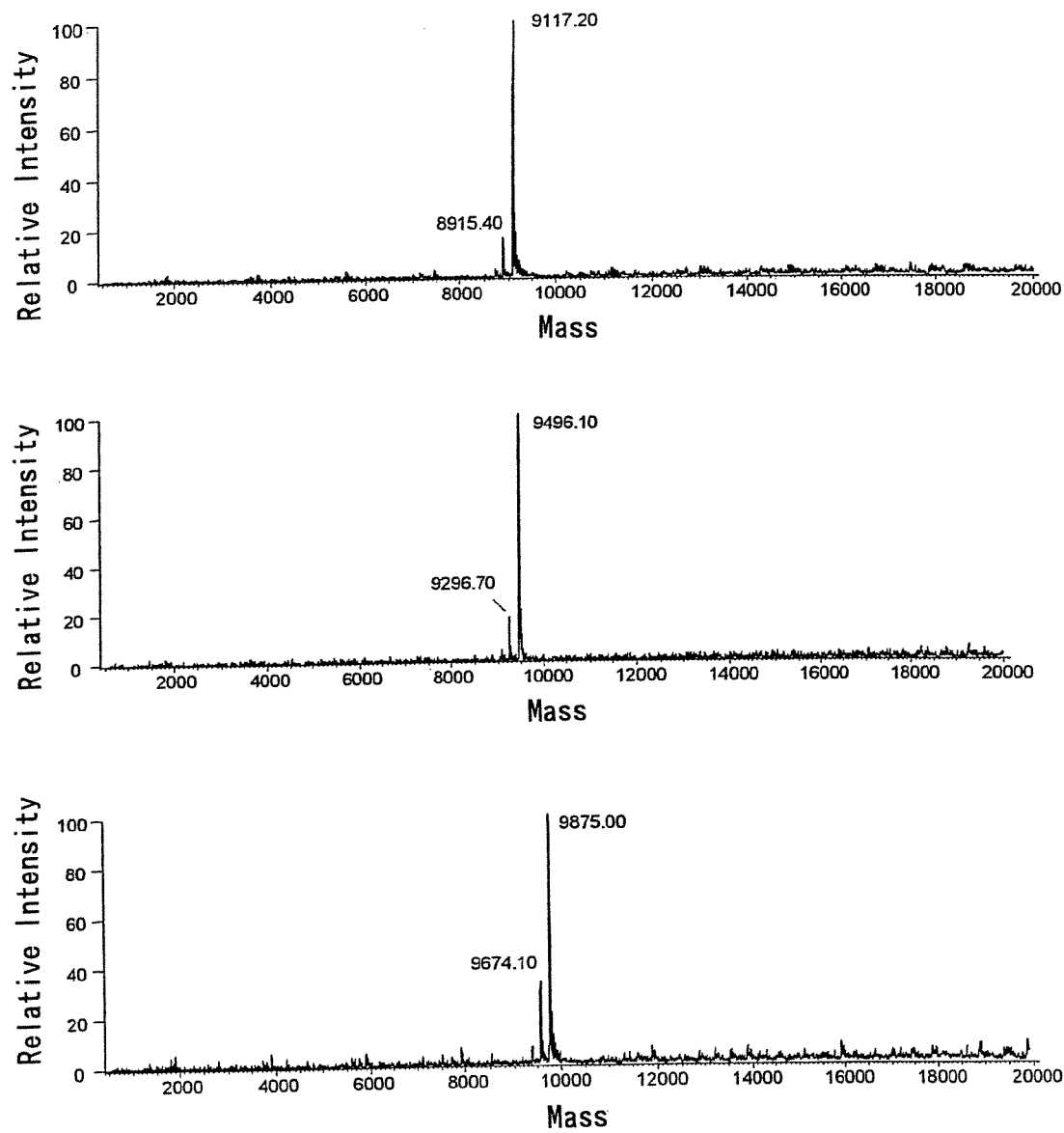
FIG. 23 shows results of deconvolution of HA48 (upper graph), HA50 (middle graph) and HA52 (lower graph).

Hereafter, the present invention will be explained more specifically with reference to the following examples.

Hereafter, hyaluronic acid oligosaccharide fractions are referred to with abbreviations of "HA4" for HA tetrasaccharide fraction, "HA6" for HA hexasaccharide fraction, "HA8" for HA octasaccharide fraction etc.

EXAMPLE 1

Preparation and Physicochemical Properties of Oligosaccharides and Fractions of the Present Invention 1. Preparation of Oligosaccharides and Fractions of the Present Invention Oligosaccharides and fractions of the present invention were prepared by the following procedures using sodium salt of HA isolated and purified from chicken crest as a raw material. The sodium salt of HA used as the raw material showed a single band in electrophoresis using a cellulose acetate membrane (electrophoresis buffer: pyridine/formic acid buffer, electric current: 15 mA, and migration time: 30 minutes), and glycosaminoglycans other than HA (chondroitin, chondroitin-4-sulfate, chondroitin-6-sulfate, chondroitin sulfate E, chondroitin sulfate D, heparin, heparan sulfate, dermatan sulfate) were not detected.

PREPARATION EXAMPLE 1

Decomposition by Hyaluronidase

In an amount of 25 g of the sodium salt of HA was dissolved in 1.1 L of 0.1 M phosphate buffer (pH 5.3) containing 0.15 M NaCl. To this solution, 200 mg of hyaluronidase derived from bovine testis (5.342 units/mg, produced by Seikagaku Corporation) was added and allowed to react at 37° C. for 9 hours.

After the reaction, the reaction mixture was centrifuged at 10,000 rpm for 30 minutes, and the supernatant was collected. The collected supernatant was applied to an ion exchange column (φ1.5×123 cm) of a strongly basic anion exchanger having trimethylammoniomethyl groups as anion exchange groups, Dowex 1×2 (100-200 mesh, produced by Dow Chemical) and eluted with a linear concentration gradient of NaCl (0.01 M to 0.50 M). Uronic acid in the obtained fractions was detected by the carbazole method to screen fractions containing HA oligosaccharides. Appropriate fractions were pooled and concentrated, and after desalting with Sephadex G-10 (produced by Pharmacia, φ3×124), the concentrate was lyophilized.

Weights of the lyophilized products of the obtained fractions are shown in the parentheses.

HA4 (330 mg), HA6 (1210 mg), HA8 (305 mg), HA10 (1625 mg), HA12 (685 mg), HA14 (620 mg), HA16 (430 mg), HA18 (210 mg), HA20 (202 mg), HA22 (819 mg), HA24 (197 mg), HA26 (187 mg), HA28 (159 mg), HA30 (137 mg), HA32 (122 mg), HA34 (102 mg), HA36 (91 mg), HA38 (89 mg), HA40 (65 mg), HA42 (76 mg), HA44 (61 mg), HA46 (58 mg), HA48 (46 mg), HA50 (48 mg), HA52 (21 mg)

PREPARATION EXAMPLE 2

Decomposition by Chondroitinase ACI

In an amount of 8 g of the sodium salt of HA was dissolved in 500 mL of 0.1 M acetate buffer (pH 6.0) containing 0.1% bovine serum albumin (BSA).

To this solution, 32 units of chondroitinase ACI (produced by Seikagaku Corporation) was added and allowed to react at 37° C. for 6 hours.

After the reaction, the reaction mixture was centrifuged at 10,000 rpm for 30 minutes, and the supernatant was collected. The collected supernatant was applied to an ion exchange column (4.5×123 cm) of Dowex 1×2 (100-200 mesh, produced by Dow Chemical) and eluted with a linear concentration gradient of NaCl (0.01 M to 0.50 M). Uronic acid in the obtained fractions was detected by the carbazole method to screen fractions containing HA oligosaccharides. Appropriate fractions were pooled and concentrated, and after desalting with Sephadex G-10 (produced by Pharmacia, ϕ3×124), the concentrate was lyophilized.

Weights of the lyophilized products of the obtained fractions are shown in the parentheses. "Δ" means that the saccharide at the non-reducing end is an unsaturated saccharide.

ΔHA4 (133 mg), ΔHA6 (133 mg), ΔHA8 (84 mg), ΔHA10 (109 mg), ΔHA12 (100 mg), ΔHA14 (101 mg), ΔHA16 (73 mg), ΔHA18 (31 mg), ΔHA20 (9 mg)

PREPARATION EXAMPLE 3

Dimethyl Sulfoxide (DMSO) Method

In an amount of 10 g of the sodium salt of HA was dissolved in 3 L of dimethyl sulfoxide containing 10% of 0.1 M HCl and subjected to a heat treatment at 105° C. for 16 hours.

After the treatment, the obtained solution was applied to Dowex 1×2 (100-200 mesh, produced by Dow Chemical) ion exchange column (ϕ3.0×78 cm) to perform chromatography. Elution was performed with a linear concentration gradient of NaCl (0.01 M to 0.50 M). Uronic acid in the obtained fractions was detected by the carbazole method to screen fractions containing HA oligosaccharides. Appropriate fractions were pooled and concentrated, and after desalting with Sephadex G-10 (produced by Pharmacia, ϕ3×124), the concentrate was lyophilized.

Weights of the lyophilized products of the obtained fractions are shown in the parentheses.

HA2 (50 mg), HA4 (1100 mg), HA6 (232 mg), HA8 (1015 mg), HA10 (1033 mg), HA12 (459 mg)

The HA oligosaccharides of various sizes obtained as described above were used for the following various analyses.

2. Physicochemical Properties of Fractions of the Present Invention

Various physicochemical properties of each of the HA oligosaccharide (sodium salt) fractions obtained in Preparation Example 1 mentioned above were investigated.

(1) Analysis by Gel Filtration Chromatography
Used column: TSK Gel 2500+3000+4000pwxl (TOSOH)
Solvent: 0.05 M NaCl
Flow rate: 0.6 mL/minute
Detection wavelength: 210 nm, differential refractometer (RI)
Applied sample amount: 200 μg/shot as amount of HA oligosaccharide The elution curves obtained by using HA4 (Lot 1) to HA14 as samples are shown in FIGS. 1 to 6. In each figure, the upper graph indicates the result of detection based on the absorbance at 210 nm, and the lower graph indicates the result of detection by using a differential refractometer.

From the results shown in these figures, it can be seen that all the fractions showed a substantially single peak.

Further, for all the cases, the relative area of the main HA peak to the sum of the peak areas of the total HA oligosaccharides in each fraction was 85% or more as detected based on the absorbance at 210 nm or 98% or more as detected by using a differential refractometer (RI) as shown in Table 1.

TABLE 1

| Sample | Ratio of main peak area to total peak areas (%) | |
|---|---|---|
| | 210 nm | RI |
| HA4 (Lot 1) | 89.037 | 99.854 |
| HA6 | 98.573 | 99.815 |
| HA8 | 96.617 | 98.929 |
| HA10 | 98.594 | 99.287 |
| HA12 | 100.000 | 100.000 |
| HA14 | 98.334 | 99.796 |

(2) Analysis by ion exchange chromatography
Column: YMC NH2 column (YMC)
Solvent: Concentration gradient of $NaH_2PO_4$ from 0 M to 0.8 M
Flow rate: 1 mL/minute
Detection wavelength: 210 nm
Applied sample amount: 20 μg/shot as amount of HA oligosaccharide The elution curves obtained by using HA4 (Lot 1) to HA14 and HA48 to HA52 as samples are shown in FIGS. 7 to 15. From the results shown in these figures, it can be seen that all the fractions showed a substantially single peak. Further, for all the cases, the relative area of the main HA peak to the sum of the peak areas of the total HA oligosaccharides in each fraction was 90% or more as shown in Table 2.

TABLE 2

| Sample | Ratio of main peak area to total peak areas (%) |
|---|---|
| HA4 (Lot 1) | 98.5007 |
| HA6 | 97.9140 |
| HA8 | 98.1209 |
| HA10 | 97.4236 |
| HA12 | 94.5425 |
| HA14 | 94.7181 |
| HA48 | 94.4743 |
| HA50 | 93.4305 |
| HA52 | 94.2492 |

(3) Analysis by Fluorescence-Labeled Gel Electrophoresis

Each of HA4, HA6, HA8, HA10, HA12, HA14 and HA16 was used to perform the following procedure. At the same time, a fraction of HA oligosaccharide mixture (also containing HA disaccharide, referred to as the "mixture" hereinafter) was also used to perform the same procedure.

(3-1) Preparation of Fluorescence-labeled HA Oligosaccharides

HA oligosaccharides contained in each fraction were labeled with fluorescence by using FACE® N-linked Oligosaccharide Profiling Kit (Glyko, Inc., Novato, Calif., U.S.A.).

A fraction in such an amount that the fraction should contain about 2 nmol of HA oligosaccharides (in the case of the mixture, about 20 nmol of oligosaccharides as HA disaccharide units) was lyophilized in a 0.5-mL plastic tube by using a centrifugation type vacuum lyophilizer (SpeedVac, AS160, SAVANT INSTRUMENTS INC., NY, U.S.A). After the lyophilization, 5 µL of 8-aminonaphthalene-1,3,6-trisulfonic acid disodium salt (ANTS) solution (GLYKO, L2, Part #50058: reconstituted OLIGO Labeling Dye) was added to each tube, stirred and left at room temperature for 15 minutes. Furthermore, 5 µL of sodium cyanoborohydride solution (GLYKO, L1, Part #50056: Labeling Reducing Agent) was added to each tube, and the tube was sealed and incubated at 36° C. for 16 hours.

After the incubation, the mixture was partially dried in a centrifugation type vacuum lyophilizer for about 15 minutes and then added with water to a volume of 20 µL.

(3-2) Electrophoresis of Fluorescence-labeled Oligosaccharides

Electrophoresis was performed by using GLYKO O-linked Oligosaccharide Profiling Gel (GLYKO, Part #60200: polyacrylamide gel having a crosslinking degree of 36%).

One pack of OLIGO Gel Running Buffer (GLYKO, Part #7000) was dissolved in distilled water so that the solution should have a volume of 1.5 L and cooled on ice.

Cooling water was circulated in a gel box (GLYKO, GLYKO Gel Box, Part #40026), the cooled Running Buffer was placed in it, and the gel was set on it. The gel box was placed on ice for cooling.

Each fraction solution containing fluorescence-labeled HA oligosaccharides was taken in a volume of 2 µL and mixed with 3 µL of distilled water and 5 µL of Loading Buffer (GLYKO, Part #50064). As for the mixture solution, 2 µL of the solution was mixed with 2 µL of Loading Buffer. The mixture in a volume of 4 µL was applied to the gel. Each fraction was applied in such an amount that 80 pmol of HA oligosaccharides should be applied per lane.

Electrophoresis was performed with a constant voltage of 1000 V for 160 minutes, and fluorescence emitted upon irradiation of a light at 365 nm light from an UV transilluminator (Model NLM-20E, UVP, California, U.S.A.) was recorded by using an instant camera (MAMIYA, Professional SD, f=127 mm) and an instant film (Polaloid® Polapan T667, ISO 3000, Polapoid Corp., Massachusetts, U.S.A). The results are shown in FIG. 16.

The relationships of the lanes in FIG. 16 and the samples are as follows.

Lane 1: mixture, Lane 2: HA4, Lane 3: HA6, Lane 4: HA8, Lane 5: HA10, Lane 6: HA12, Lane 7: HA14, Lane 8: HA16

While the mixture showed ladder-like bands, all of the fractionated oligosaccharide fractions each formed a single band with migration corresponding to the size of each oligosaccharide, and bands of HA oligosaccharides of other sizes were not detected.

Further, an oligosaccharide of a smaller size showed a larger migration degree. The positions of bands (migration position) observed for the fractions well corresponded to those of the ladder-like bands observed for the mixture, and thus it was demonstrated that the migration degrees of molecules were not affected even in a mixture of oligosaccharides of multiple kinds of sizes.

GLYKO O-linked Profiling Gel is polyacrylamide gel having a crosslinking degree of 36%. 8-Aminonaphthalene-1,3, 6-trisulfonic acid disodium salt (ANTS) is a fluorescent substance having trivalent negative charge.

When 2-aminoacridon (AMAC) having no charge was used as a fluorescent substance, all of the oligosaccharides did not substantially migrate on this gel. This suggested that only the negative charge of HA oligosaccharide itself was insufficient for migration on the gel of high crosslinking degree, and charge of bound ANTS was required. Further, since boric acid known to interact with a saccharide chain basic structure was not used, it was suggested that the relationship between the oligosaccharide size and the mesh size of polyacrylamide directly determine the migration degree.

When other gels available from Glyko (crosslinking degree of 20% or 21%) and labeling with ANTS were used, HA octasaccharide and oligosaccharides of smaller sizes could not be separated, or HA tetrasaccharide and oligosaccharides of smaller sizes could not be detected because they overlapped with the migration front.

(4) Mass Spectrometry

Mass spectrometry was performed by the electrospray ionization mass spectrometry (ESIMS) method.

(4-1) Method (4-1-1) Sample for Analysis

Aqueous solutions of HA4 (Lot 1), HA6, HA8, HA10, HA12, HA14, HA16, HA48, HA50 and HA52 were prepared to have concentrations of 2.6 mg/mL, 1.2 mg/mL, 1.4 mg/mL, 3.0 mg/mL, 2.0 mg/mL, 6.5 mg/mL, 1.3 mg/mL, 1 mg/mL, 1 mg/mL and 1 mg/mL, respectively, and analyzed.

The theoretical molecular weights of HA oligosaccharides were obtained based on the fact that HA tetrasaccharide to HA dopentacontasaccharide have a structure represented by the following formula (1).

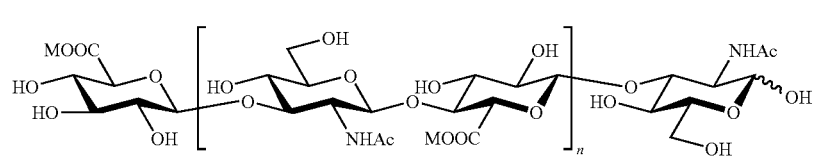

Formula (1)

(In the formula, n is an integer of 1 to 29, M represents a proton or a monovalent cation, and Ac represents acetyl group.)

(4-1-2) Reagents

Methanol (Wako Pure Chemical Industries) and distilled water (Wako Pure Chemical Industries) were those for HPLC, and ammonium formate of special grade (Wako Pure Chemical Industries) was used.

(4-1-3) Instruments and Equipments

1) HPLC System

Agilent 1100 Series: binary pump, degasser, autosampler (Agilent Technologies)

2) Mass Spectrometer
Triple quadrupole mass spectrometer: TSQ (ThermoQuest)

(4-1-4) ESIMS Analysis Conditions
Introduction of a sample into the mass spectrometer was attained by injecting 5 μL or 10 μL of each sample solution into the HPLC system connected to the mass spectrometer. The analysis conditions of HPLC and ESIMS are as follows.

1) HPLC
Mobile phase: 10 mM ammonium formate aqueous solution/methanol=80/20
Flow rate: 0.2 mL/minute
Column: not used
Injection amount: 10 μL 2) ESIMS
Probe: Off-axis
Ion mode: anion mode
Ionizing method: ESI method (electrospray ionization method)
ESI spray voltage: 4.5 kV
Heated capillary temperature: 350° C.
Auxiliary gas: 35 units
Sheath gas: 50 psi
Scanning range: m/z 10-2500 or 10-4000
Scanning time: 1.5 seconds or 3 seconds (4-1-5) Deconvolution Analysis
Deconvolution analysis for estimation of molecular weight from an observed ESIMS spectrum was performed by using analysis software, Xcalibur Bioworks (ThermoQuest).

(4-2) Results
The results of the anion ESIMS spectrum measurement of HA4 to HA16 are summarized in Tables 3 and 4, and spectra of HA4 to HA16 and HA48 to HA52 are shown in FIGS. 17 to 23.

TABLE 3

| Sample | $[M-H]^-$ | $[M-2H]^{2-}$ | $[M-3H]^{3-}$ | $[M-4H]^{4-}$ | $[M-5H]^{5-}$ | $[M+Na-2H]^-$ | $[M+Na-3H]^{2-}$ | $[M+2Na-4H]^{2-}$ |
|---|---|---|---|---|---|---|---|---|
| HA4 (Lot1) | 774.9 100 | 386.9 55 | | | | 797.1 27 | | |
| HA6 | 1153.9 45 | 576.6 100 | 383.8 1 | | | 1176.1 2 | 587.6 19 | |
| HA8 | 1533.9 36 | 766.1 100 | 510.3 3 | | | | 777.0 9 | |
| HA10 | 1912.8 16 | 955.9 100 | 636.9 15 | | | | 967.0 4 | |
| HA12 | 2292.1 12 | 1145.5 100 | 763.2 91 | 572.3 13 | | | 1156.3 16 | 1167.4 8 |
| HA14 | | 1335.3 79 | 889.5 100 | 666.6 12 | | | 1346.2 9 | 1357.5 4 |
| HA16 | | 1524.8 52 | 1016.1 100 | 761.6 17 | 608.9 5 | | 1535.7 4 | |

| Sample | $[M+Na-4H]^{3-}$ | $[M+2Na-5H]^{3-}$ | $[M+3Na-6H]^{3-}$ | $[2M-H]^-$ | $[2M-3H]^{3-}$ | Deconvolution mass |
|---|---|---|---|---|---|---|
| HA4 (Lot1) | | | | 1551.6 15 | | |
| HA6 | | | | | 769.1 3 | 1155.1 |
| HA8 | | | | | 1022.3 10 | 1534.5 |
| HA10 | | | | | 1275.2 9 | 1913.7 |
| HA12 | 770.5 15 | 777.9 8 | | | 1527.9 11 | 2293.1 |
| HA14 | 897.1 14 | | | | 1780.6 4 | 2671.9 |
| HA16 | 1023.4 16 | 1030.6 9 | 1037.6 3 | | | 3051.2 |

Upper Line: Measured Value
Lower Line: Relative Intensity of Peak (%)

TABLE 4

| Sample | $[M-5H]^{5-}$ | $[M-6H]^{6-}$ | $[M-7H]^{7-}$ | $[M-8H]^{8-}$ | $[M-9H]^{9-}$ | $[M-10H]^{10-}$ | $[M-11H]^{11-}$ | $[M-12H]^{12-}$ |
|---|---|---|---|---|---|---|---|---|
| HA48 | 1822.4 100 | 1518.7 7 | 1301.9 6 | 1138.4 12 | 1011.7 16 | 910.5 37 | 827.9 77 | 758.6 59 |
| HA50 | 1898.2 100 | 1581.4 7 | 1355.5 2 | 1186.5 7 | 1054.1 8 | 948.7 16 | 861.9 26 | 790.3 23 |
| HA52 | 1974.2 | 1645.3 | 1409.5 | 1233.0 | 1096.4 | 986.7 | 896.6 | 821.8 |

TABLE 4-continued

| 100 | 23 | 7 | 11 | 23 | 27 | 69 | 98 |
|---|---|---|---|---|---|---|---|

| | Molecule Related Ions(m/z) | | | | | Deconvolution |
|---|---|---|---|---|---|---|
| Sample | $[M - 13H]^{13-}$ | $[M - 14H]^{14-}$ | $[M + Na - 6H]^{6-}$ | $[M + 2Na - 7H]^{5-}$ | $[M + 3Na - 8H]^{5-}$ | mass |
| HA48 | 700.2 | 650.0 | 1826.7 | 1831.7 | 1835.6 | 9117.2 |
|  | 22 | 8 | 45 | 25 | 23 |  |
| HA50 | 729.4 | 677.1 | 1903.0 | 1907.3 | 1911.8 | 9496.1 |
|  | 19 | 14 | 43 | 19 | 12 |  |
| HA52 | 758.4 | 704.3 | 1979.3 | 1983.5 | 1987.4 | 9875.0 |
|  | 45 | 20 | 50 | 37 | 39 |  |

Upper Line: Measured Value
Lower Line: Relative Intensity of Peak (%)

In the aforementioned results, various molecule-related ions all considered to be derived from HA oligosaccharides were observed, and they are not contradictory to interpretations that HA4 (Lot 1) should correspond to HA tetrasaccharide, HA6 to hexasaccharide, HA8 to HA octasaccharide, HA10 to HA decasaccharide, HA12 to HA dodecasaccharide, HA14 to HA tetradecasaccharide, HA16 to HA hexadecasaccharide, HA48 to HA octatetracontasaccharide, HA50 to HA pentacontasaccharide and HA52 to HA dopentacontasaccharide.

Based on the above results, relative values of the actually measured values for the main peaks with respect to the theoretical values of monoisotopic molecular weights, which were taken as 1, were calculated. The results are shown in Table 5A. In addition, as for HA4, the actually measured value and theoretical value for $[M-H]^-$ were used.

TABLE 5A

| Sample | Found | Calculated | Relative value |
|---|---|---|---|
| HA4 (Lot 1) | 774.9 | 775.2 | 0.9996 |
| HA6 | 1155.1 | 1155.3 | 0.9998 |
| HA8 | 1534.5 | 1534.5 | 1.0000 |
| HA10 | 1913.7 | 1913.6 | 1.0001 |
| HA12 | 2293.1 | 2292.7 | 1.0002 |
| HA14 | 2671.9 | 2671.8 | 1.0000 |
| HA16 | 3051.2 | 3050.9 | 1.0001 |
| HA48 | 9117.2 | 9116.7 | 1.0001 |
| HA50 | 9496.1 | 9495.8 | 1.0000 |
| HA52 | 9875.0 | 9874.9 | 1.0000 |

Further, relative values of the actually measured values for the main peaks with respect to the theoretical values of average molecular weights, which are taken as 1, were calculated. The results are shown in Table 5B. As for HA4, the actually measured value and theoretical value for $[M-H]^-$ were used.

TABLE 5B

| Sample | Found | Calculated | Relative value |
|---|---|---|---|
| HA4 (Lot 1) | 774.9 | 775.6 | 0.9991 |
| HA6 | 1155.1 | 1156.0 | 0.9992 |
| HA8 | 1534.5 | 1535.3 | 0.9995 |
| HA10 | 1913.7 | 1914.6 | 0.9995 |
| HA12 | 2293.1 | 2293.9 | 0.9997 |
| HA14 | 2671.9 | 2673.3 | 0.9995 |
| HA16 | 3051.2 | 3052.6 | 0.9995 |
| HA48 | 9117.2 | 9121.7 | 0.9995 |
| HA50 | 9496.1 | 9501.0 | 0.9995 |
| HA52 | 9875.0 | 9880.3 | 0.9995 |

From these results, it was demonstrated that, when the theoretical values of the monoisotopic molecular weights or average molecular weights of HA oligosaccharides constituting the fractions of the present invention were taken as 1, the actually measured values of the fractions obtained by mass spectrometry were within the range of 0.999-1.001 (relative value).

(5) Elemental Analysis

HA4 (Lot 1), HA6, HA8, HA10, HA12, HA14 and HA16 were dried at 80° C. for 2 hours under reduced pressure and immediately analyzed by using an elemental analyser. The results are shown in Table 6.

TABLE 6

| Sample | Element | Calculated (%) | Found (%) | Error |
|---|---|---|---|---|
| HA4 (Lot 1) | C | 40.98 | 40.63 | 0.35 |
|  | N | 5.16 | 5.20 | -0.04 |
|  | N | 3.41 | 3.34 | 0.07 |
|  | Na | 5.60 | 5.48 | 0.12 |
| HA6 | C | 41.28 | 40.74 | 0.54 |
|  | H | 5.11 | 5.17 | -0.06 |
|  | N | 3.44 | 3.31 | 0.13 |
|  | Na | 5.64 | 5.75 | -0.11 |
| HA8 | C | 41.44 | 41.41 | 0.03 |
|  | H | 5.09 | 5.22 | -0.13 |
|  | N | 3.45 | 3.36 | 0.09 |
|  | Na | 5.67 | 5.41 | 0.26 |
| HA10 | C | 41.53 | 41.41 | 0.12 |
|  | H | 5.08 | 5.24 | -0.16 |
|  | N | 3.46 | 3.43 | 0.03 |
|  | Na | 5.68 | 5.45 | 0.23 |
| HA12 | C | 41.59 | 40.96 | 0.63 |
|  | H | 5.07 | 5.33 | -0.26 |
|  | N | 3.46 | 3.23 | 0.23 |
|  | Na | 5.69 | 5.41 | 0.28 |
| HA14 | C | 41.64 | 41.44 | 0.20 |
|  | H | 5.06 | 5.36 | -0.30 |
|  | N | 3.47 | 3.37 | 0.10 |
|  | Na | 5.69 | 5.20 | 0.49 |

Thus, it was demonstrated that the differences between the theoretical values of content ratios (weight %) of carbon (C), hydrogen (H), nitrogen (N) and sodium (Na) in HA oligosaccharides (sodium salts) constituting the fractions of the present invention and the actually measured values of the same (weight %) obtained by elemental analysis of the corresponding fractions were all with in the range of ±1 (weight %).

(6) Nuclear Magnetic Resonance Spectrum (NMR)

$^1$H-NMR and $^{13}$C-NMR of the HA oligosaccharide fractions were measured by using VARIAN UnityInova Model 500. As the measurement solvent, $D_2O$ was used. The measurement was performed by using t-BuOH ($^1$H, 1.23 ppm, $^{13}$C, 32.461 ppm) as an internal standard at a measurement temperature of 23° C. The results for the HA oligosaccharide fractions are shown below. Further, spectra of the fractions are shown in FIGS. 24 to 40.

(6-1) Measurement Result of HA4 (Lot 1)

500 MHz $^1$H-NMR δ; 2.004 (s, 3H, NAc), 2.018, 2.019 (3H, NAc), 3.292-3.326 (m, 1H, H-2d), 3.354 (dd, 1H, $J_{1,2}$=7.9 Hz, $J_{2,3}$=9.5 Hz, H-2b), 4.027 (dd, 0.6H, $J_{1,2}$=3.5 Hz, $J_{2,3}$=10.6 Hz, H-2aα), 4.453 (d, $J_{1,2}$=7.9 Hz, H-1d), 4.460 (d, H-1bβ), 4.502 (d, 0.6H, H-1bα), 4.555 (d, 1H, $J_{1,2}$=8.4 Hz, H-1c), 4.705 (d, 0.4H, $J_{1,2}$=8.4 Hz, H-1aβ), 5.144 (d, 0.6H, H-1aα)

Figure 24:
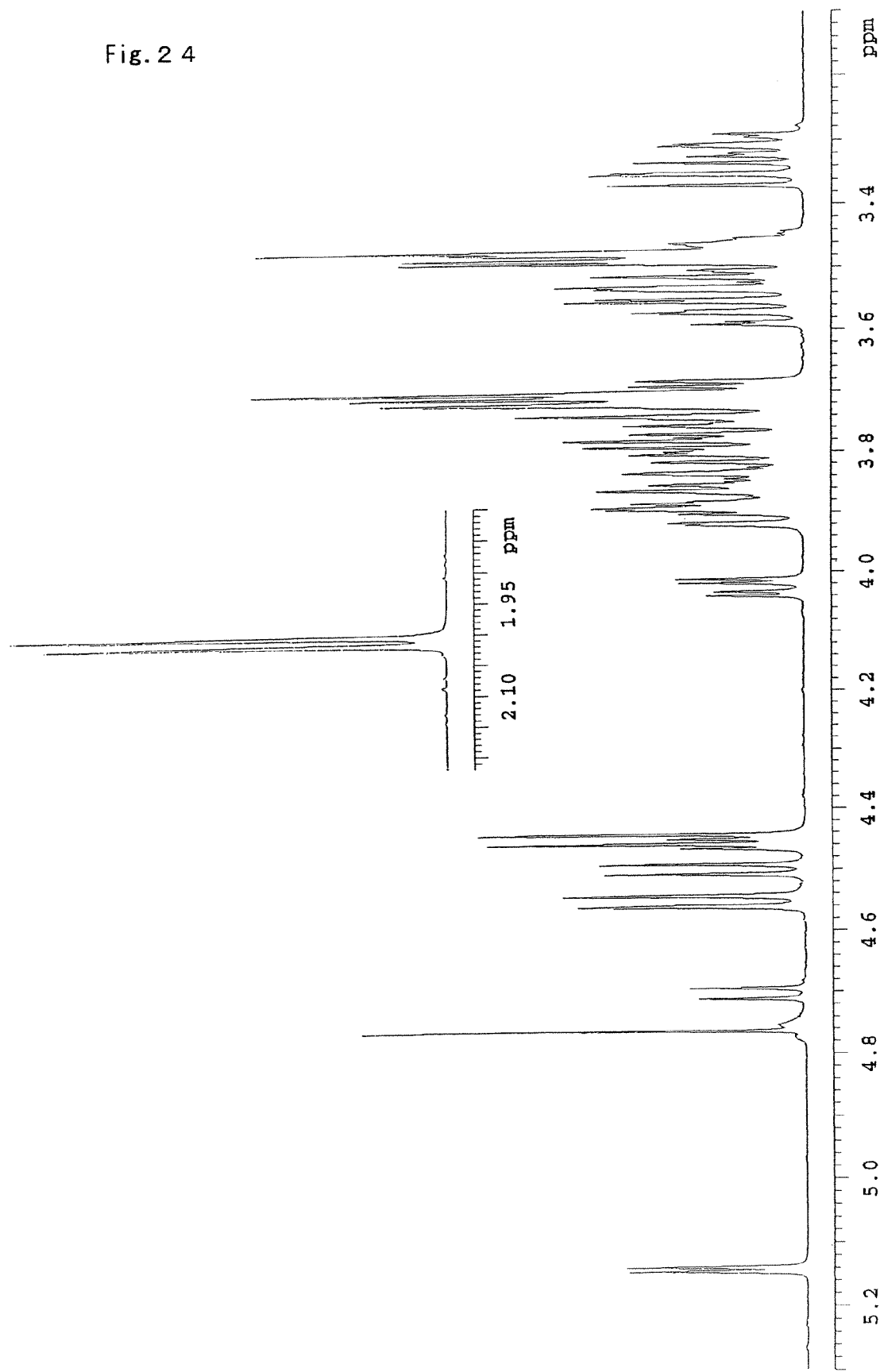
FIG. 24 shows $^1$H-NMR spectrum of HA4.
Figure 2:
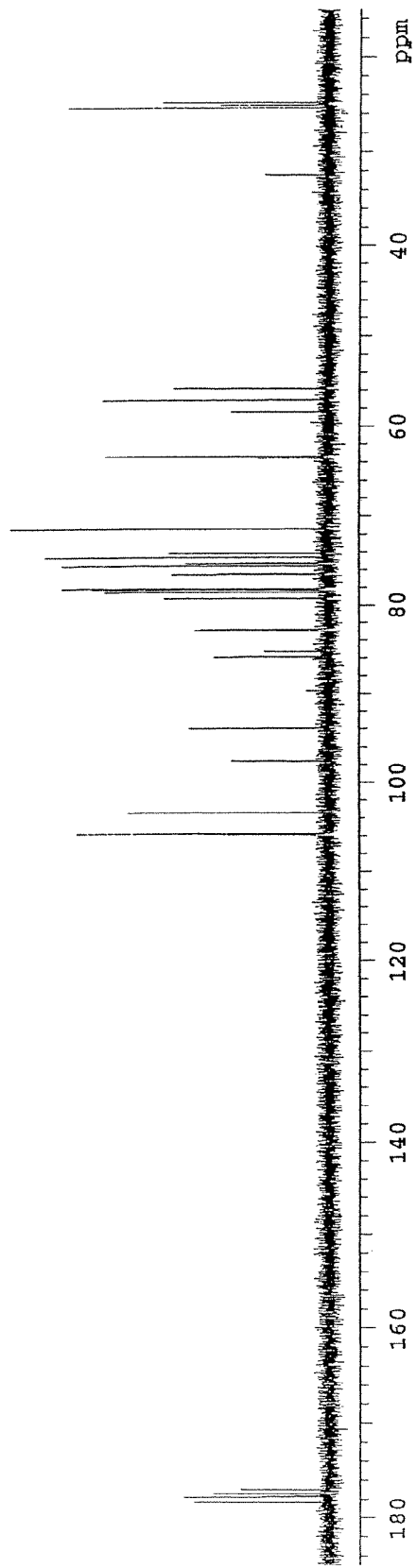
Figure 2:
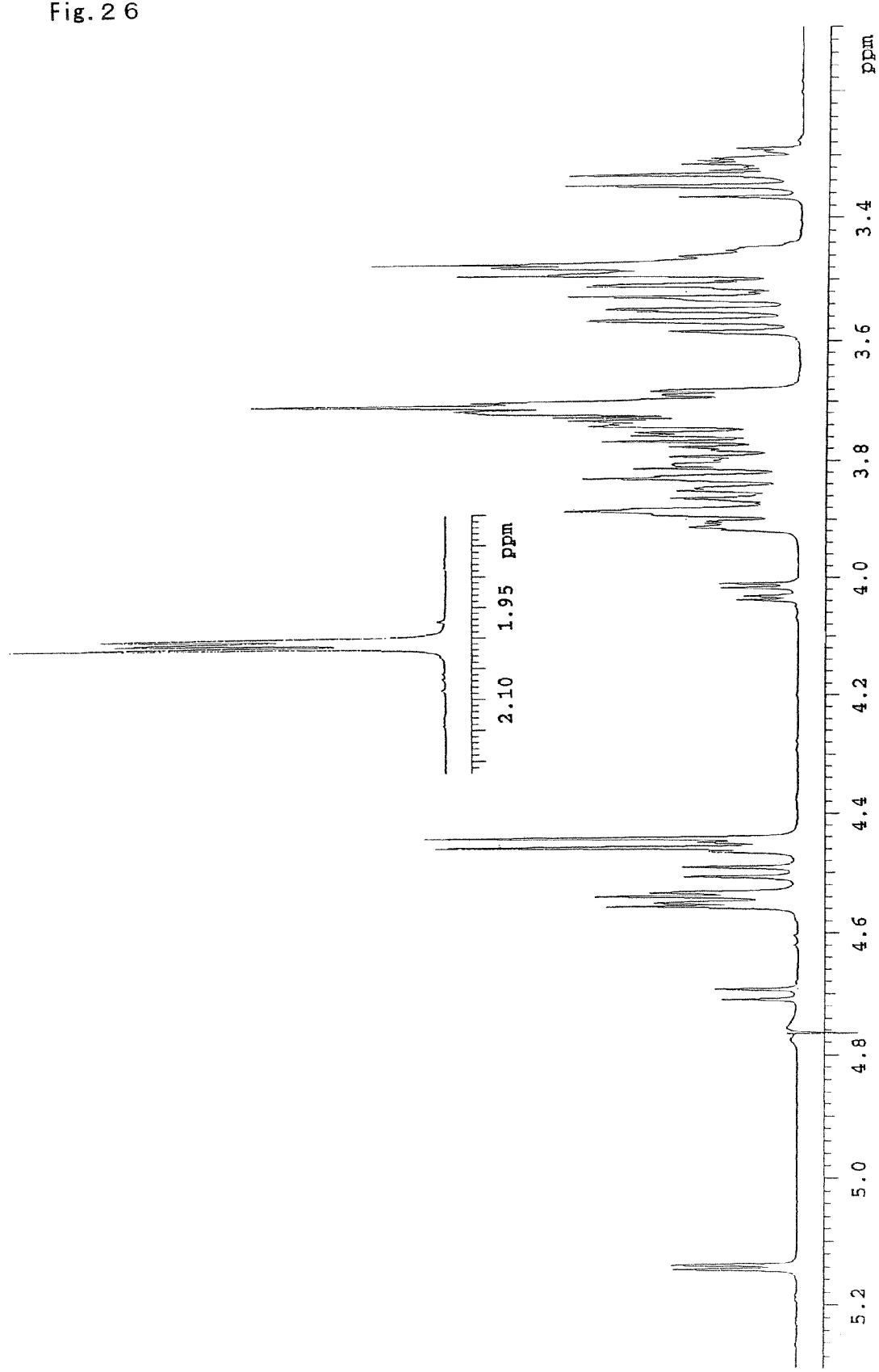

The spectrum used as the basis of the analysis is shown in FIG. 24.

125 MHz $^{13}$C-NMR δ; 24.84, 25.09, 25.36 (NHCOCH$_3$), 55.81 (C-2aα), 57.09 (C-2c), 58.44 (C-2aβ), 63.40, 63.57 (C-6a or C-6c), 75.29, 75.33 (C-2bα or C-2bβ), 75.58 (C-2d), 93.92 (C-1aα), 97.61 (C-1aβ), 103.44 (C-1c), 105.80, 105.84, 105.95 (C-1bα or C-1bβ or C-1d), 177.00, 177.04, 177.41, 177.68, 177.80, 178.33 (carbonyl)

The spectrum used as the basis of the analysis is shown in FIG. 25.

These results are not contradictory to the structure represented by the aforementioned formula (1) wherein n=1 (structure of sodium β-D-glucopyranosyluronate-(1→3)-2-acetamido-2-deoxy-β-D-glucopyranosyl-(1→4)-(sodium β-D-glucopyranosyluronate)-(1→3)-2-acetamido-2-deoxy-D-glucopyranose).

(6-2) Measurement Results of HA6

500 MHz $^1$H-NMR δ; 2.002, 2.010, 2.017 (9H, NAc), 3.291-3.368 (m, 3H, H-2b, H-2d and H-2f), 4.026 (dd, 0.6H, $J_{1,2}$=3.5 Hz, $J_{2,3}$=10.6 Hz, H-2aα), 4.452, 4.459 (d×2, 2.4H, $J_{1,2}$=7.8 Hz, $J_{1,2}$2=7.8 Hz, H-1bβ, H-1d and H-1f), 4.500 (d, 0.6H, $J_{1,2}$=7.9 Hz, H-1bα), 4.544, 4.550 (d×2, 2H, $J_{1,2}$=8.5 Hz, $J_{1,2}$=8.5 Hz, H-1c or H-1e), 4.702 (d, 0.4H, $J_{1,2}$=8.3 Hz, H-1aβ), 5.142 (d, 0.6H, H-1aα)

The spectrum used as the basis of the analysis is shown in FIG. 26.

125 MHz $^{13}$C-NMR δ; 24.84, 25.09, 25.35 (NHCOCH$_3$), 55.81 (C-2aα), 57.09, 57.16 (C-2c or C-2e), 58.44 (C-2aβ), 63.40, 63.57 (C-6a or C-6c or C-6e), 75.28, 75.31, 75.34, 75.57 (C-2bα or C-2bβ or C-2d or C-2f), 93.92 (C-1aα), 97.61 (C-1aβ), 103.40, 103.45 (C-1c or C-1e), 105.80, 105.85, 105.94, 106.02 (C-1bα or C-1bβ or C-1d or C-1f), 176.97, 177.40, 177.68, 177.80, 178.27 (carbonyl)

Figure 27:
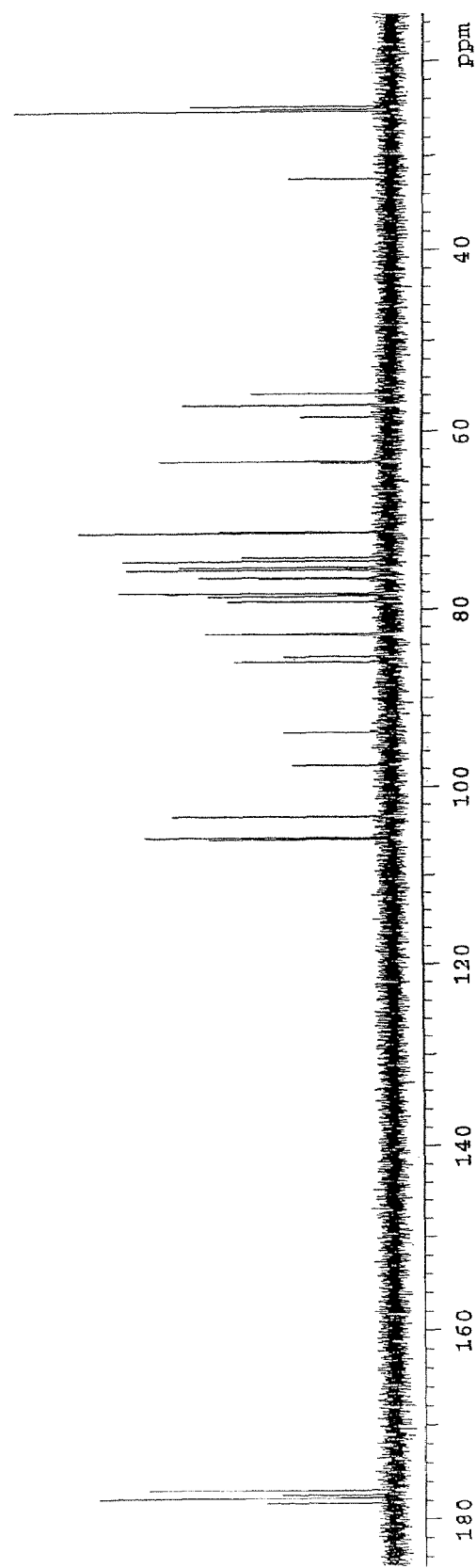
FIG. 27 shows $^{13}$C-NMR spectrum of HA6.

The spectrum used as the basis of the analysis is shown in FIG. 27.

These results are not contradictory to the structure represented by the aforementioned formula (1) wherein n=2 (structure of sodium β-D-glucopyranosyluronate-[(1→3)-2-acetamido-2-deoxy-β-D-glucopyranosyl-(1→4)-(sodium β-D-glucopyranosyluronate)]$_2$-(1→3)-2-acetamido-2-deoxy-D-glucopyranose).

(6-3) Measurement Results of HA8

500 MHz $^1$H-NMR δ; 2.002, 2.003, 2.008, 2.016 (12H, NAc), 3.290-3.368 (m, 4H, H-2b, H-2d, H-2f and H-2h), 4.025 (dd, 0.6H, $J_{1,2}$=3.5 Hz, $J_{2,3}$=10.6 Hz, H-2aα), 4.450, 4.458 (d×2, 3.4H, $J_{1,2}$=7.8 Hz, $J_{1,2}$=7.8 Hz, H-1bβ, H-1d, H-1f and H-1h), 4.500 (d, 0.6H, $J_{1,2}$=7.8 Hz, H-1bα), 4.539, 4.543, 4.550 (d×3, 3H, $J_{1,2}$=8.4 Hz, $J_{1,2}$=8.5 Hz, $J_{1,2}$=8.4 Hz, H-1c or H-1e or H-1g), 4.702 (d, 0.4H, $J_{1,2}$=8.4 Hz, H-1aβ), 5.142 (d, 0.6H, H-1aα)

Figure 28:
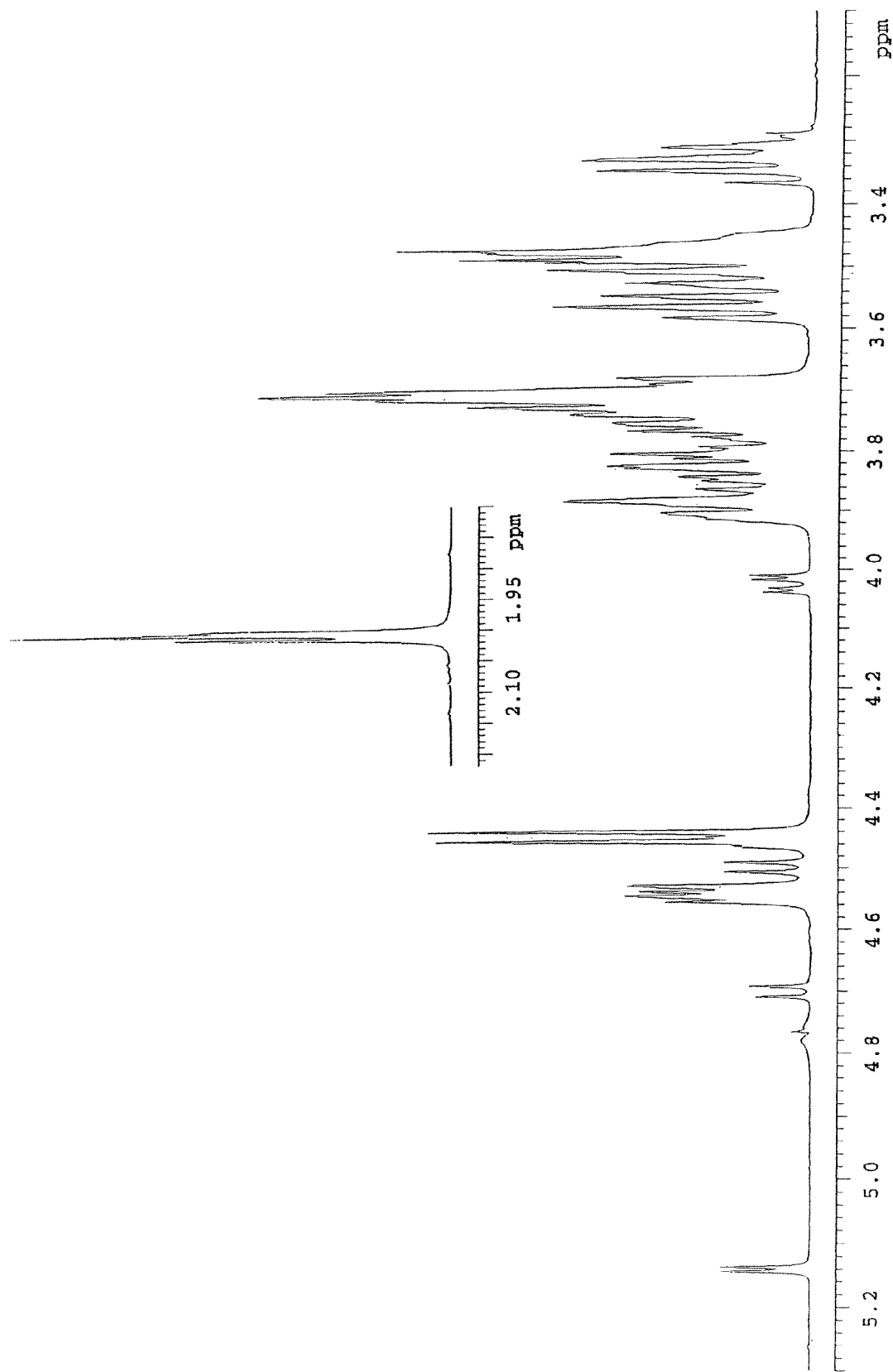
FIG. 28 shows $^1$H-NMR spectrum of HA8.

The spectrum used as the basis of the analysis is shown in FIG. 28.

125 MHz $^{13}$C-NMR δ; 24.84, 25.09, 25.35 (NHCOCH$_3$), 55.82 (C-2aα), 57.10, 57.16 (C-2c, C-2e and C-2g), 58.44 (C-2aβ), 63.40, 63.57 (C-6a, C-6c and C-6e), 75.28, 75.34, 75.57 (C-2b, C-2d, C-2f and C-2h), 93.92 (C-1aα), 97.61 (C-1aβ), 103.39, 103.45 (C-1c, C-1e and C-1g), 105.80, 105.85, 105.95, 106.04 (C-1b or C-1d or C-1f or C-1h), 176.93, 177.40, 177.68, 177.80, 178.27 (carbonyl)

Figure 29:
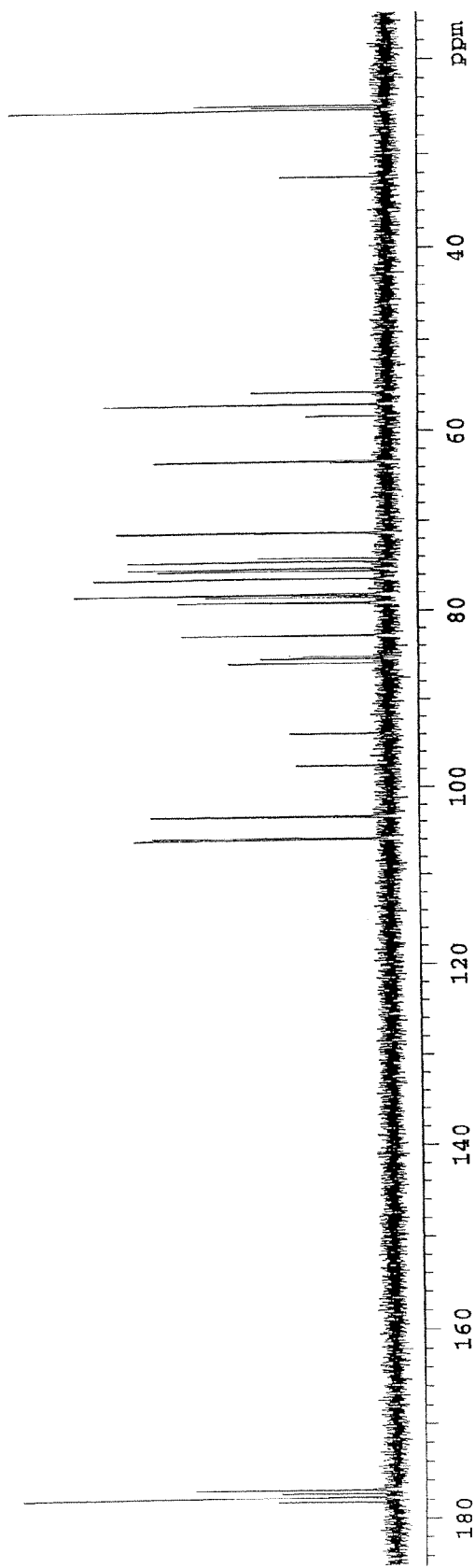
FIG. 29 shows $^{13}$C-NMR spectrum of HA8.

The spectrum used as the basis of the analysis is shown in FIG. 29.

These results are not contradictory to the structure represented by the aforementioned formula (1) wherein n=3 (structure of sodium β-D-glucopyranosyluronate-[(1→3)-2-acetamido-2-deoxy-β-D-glucopyranosyl-(1→4)-(sodium β-D-glucopyranosyluronate)]$_3$-(1→3)-2-acetamido-2-deoxy-D-glucopyranose).

(6-4) Measurement Results of HA10

500 MHz $^1$H-NMR δ; 2.001, 2.007, 2.016 (15H, NAc), 4.025 (dd, 0.6H, $J_{1,2}$=3.6 Hz, $J_{2,3}$=10.6 Hz, H-2aα), 4.441-4.465 (m, H-1bβ, H-1d, H-1f, H-1h and H-1j), 4.499 (d, $J_{1,2}$=7.8 Hz, H-1bα), 4.538, 4.549 (d×2, $J_{1,2}$=8.4 Hz, $J_{1,2}$=8.4 Hz, H-1c, H-1e, H-1g and H-1i), 4.701 (d, $J_{1,2}$=8.4 Hz, H-1aβ), 5.141 (d, 0.6H, H-1aα)

Figure 30:
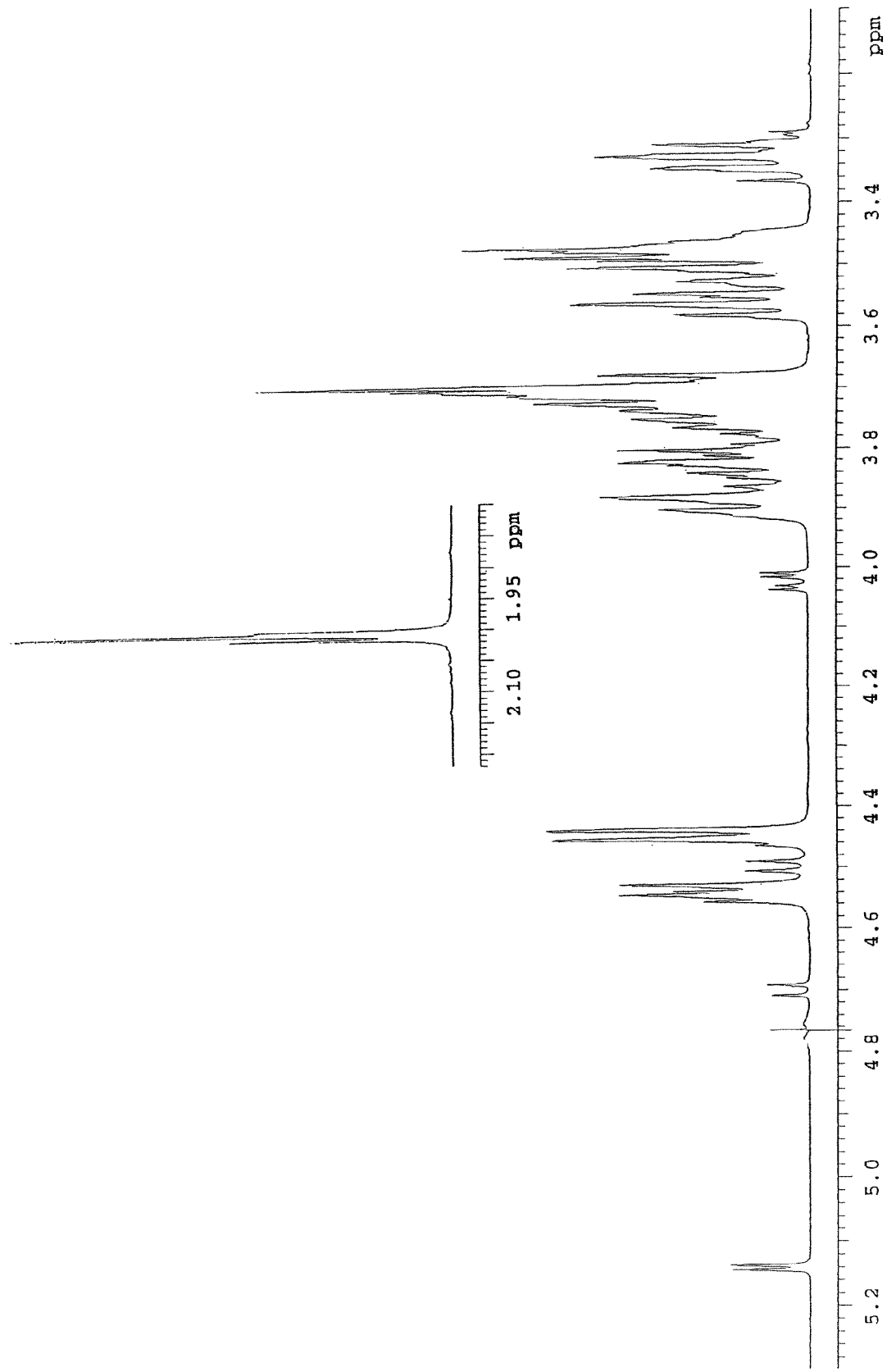
FIG. 30 shows $^1$H-NMR spectrum of HA10.
Figure 3:
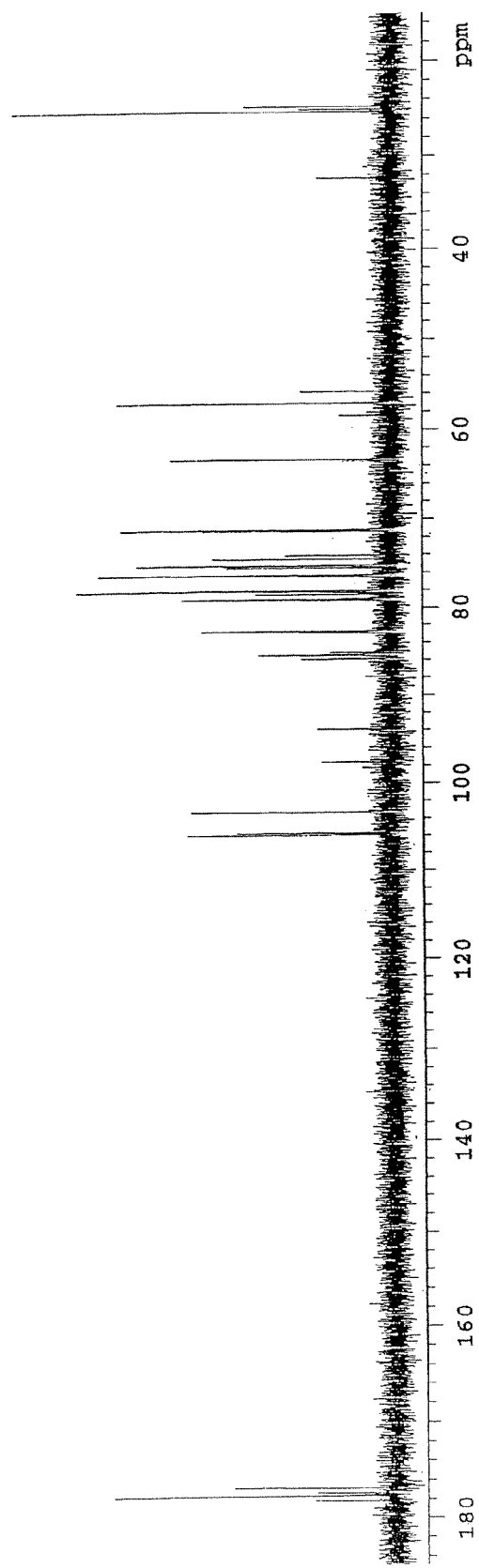

The spectrum used as the basis of the analysis is shown in FIG. 30.

125 MHz $^{13}$C-NMR δ; 24.84, 25.09, 25.35 (NHCOCH$_3$), 55.82 (C-2aα), 57.10, 57.16 (C-2c, C-2e, C-2g and C-2i), 58.44 (C-2aβ), 63.37, 63.57 (C-6a, C-6c, C-6e, C-6g and C-6i), 75.35, 75.58 (C-2b, C-2d, C-2f, C-2h and C-2j), 93.92 (C-1aα), 97.61 (C-1aβ), 103.39, 103.46 (C-1c, C-1e, C-1g and C-1i), 105.80, 105.86, 105.94, 106.05 (C-1b, C-1d, C1f, C-1h and C-1j), 176.94, 176.99, 177.41, 177.68, 177.81, 178.30 (carbonyl)

The spectrum used as the basis of the analysis is shown in FIG. 31.

These results are not contradictory to the structure represented by the aforementioned formula (1) wherein n=4 (structure of sodium β-D-glucopyranosyluronate-[(1→3)-2-acetamido-2-deoxy-β-D-glucopyranosyl-(1→4)-(sodium β-D-glucopyranosyluronate)]$_4$-(1→3)-2-acetamido-2-deoxy-D-glucopyranose).

(6-5) Measurement Results of HA12

500 MHz $^1$H-NMR δ; 2.002, 2.006, 2.016 (18H, NAc), 4.025 (dd, 0.6H, $J_{1,2}$=3.6 Hz, $J_{2,3}$=10.7 Hz, H-2aα), 4.440-4.465 (m, H-1bβ, H-1d, H-1f, H-1h, H-1j and H-1l), 4.498 (d, $J_{1,2}$=7.8 Hz, H-1bα), 4.538, 4.549 (d×2, $J_{1,2}$=8.4 Hz, $J_{1,2}$=8.4 Hz, H-1c, H-1e, H-1g, H-1i and H-1k), 4.701 (d, $J_{1,2}$=8.5 Hz, H-1aβ), 5.141 (d, 0.6H, H-1aα)

Figure 32:
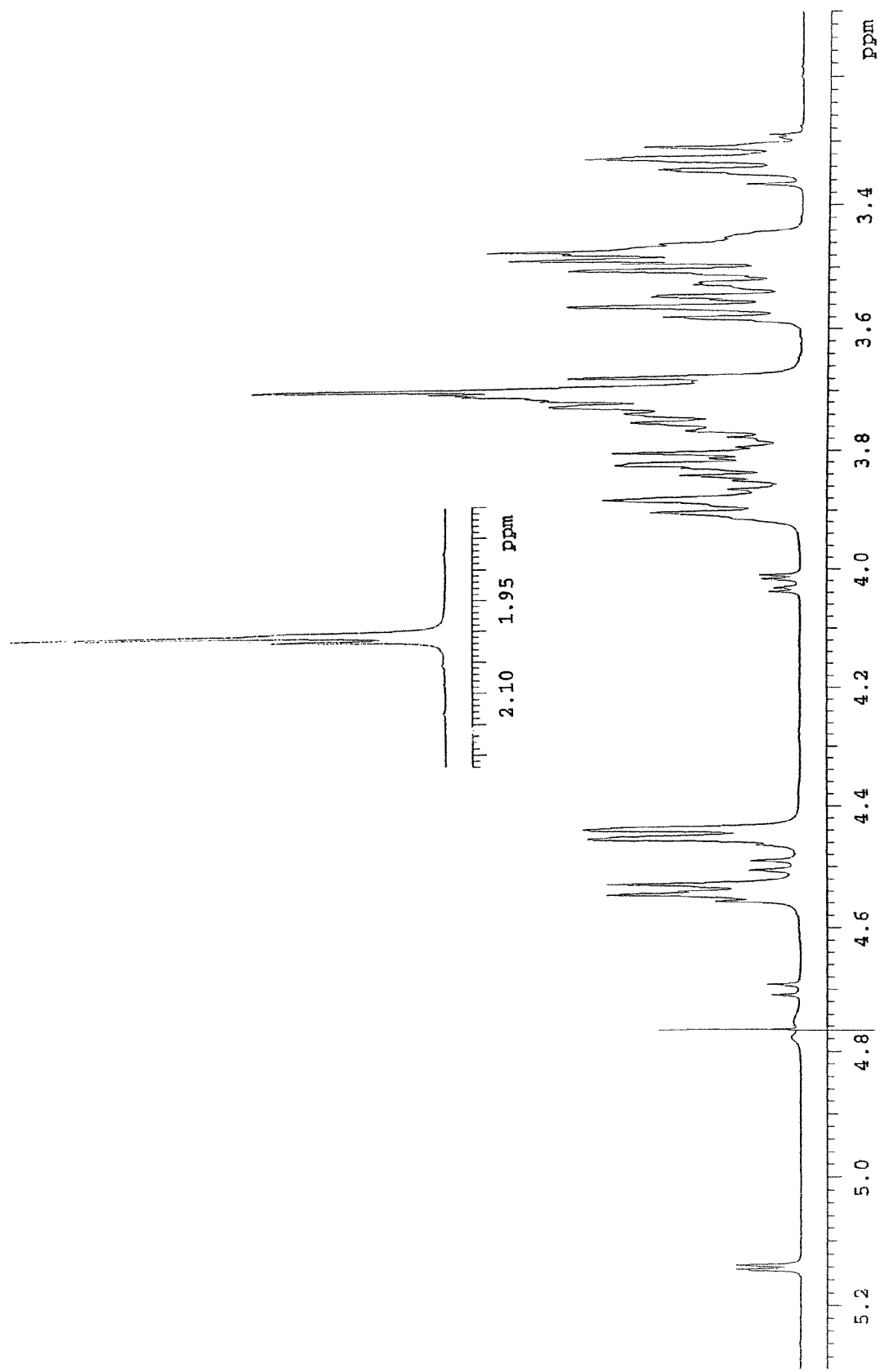
FIG. 32 shows $^1$H-NMR spectrum of HA12.

The spectrum used as the basis of the analysis is shown in FIG. 32.

125 MHz $^{13}$C-NMR δ; 24.84, 25.09, 25.35 (NHCOCH$_3$), 55.82 (C-2aα), 57.09, 57.16 (C-2c, C-2e, C-2g and C-2i), 58.44 (C-2aβ), 63.37 (C-6a, C-6c, C-6e, C-6g and C-6i), 75.35, 75.58 (C-2b, C-2d, C-2f, C-2h and C-2j), 93.92 (C-1aα), 97.61 (C-1aβ), 103.40, 103.45 (C-1c, C-1e, C-1g and C-1i), 105.80, 105.86, 106.05 (C-1b, C-1d, C1f, C-1h and C-1j), 176.95, 177.40, 177.80, 178.31 (carbonyl)

Figure 33:
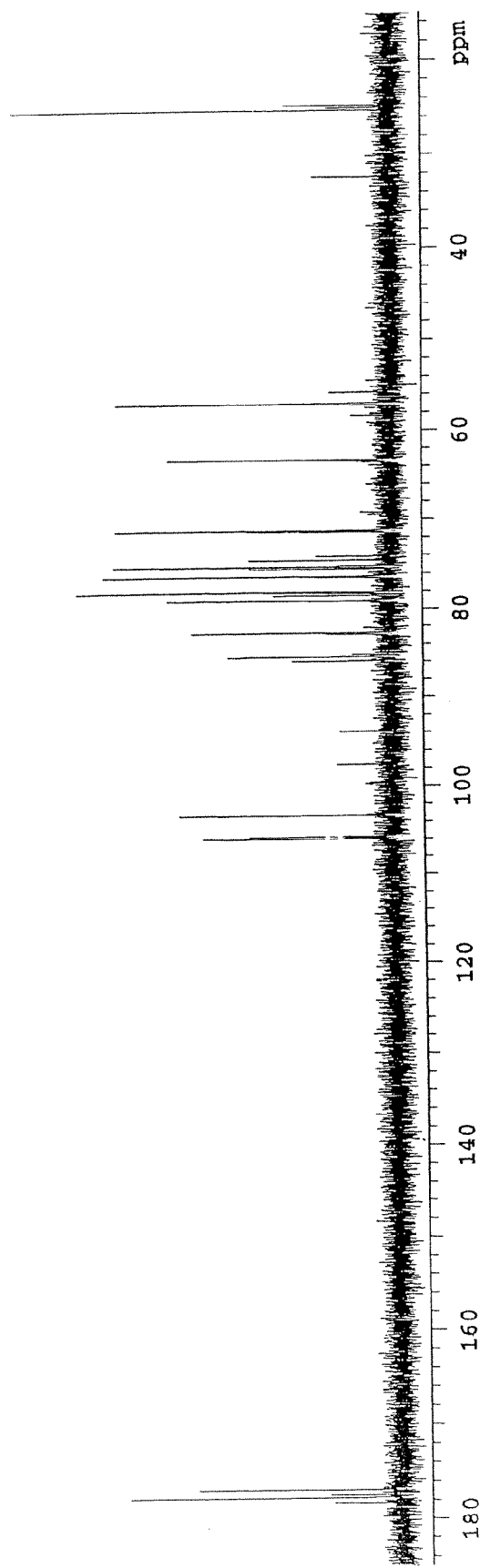
FIG. 33 shows $^{13}$C-NMR spectrum of HA12.

The spectrum used as the basis of the analysis is shown in FIG. 33.

These results are not contradictory to the structure represented by the aforementioned formula (1) wherein n=5 (structure of sodium β-D-glucopyranosyluronate-[(1→3)-2-acetamido-2-deoxy-β-D-glucopyranosyl-(1→4)-(sodium β-D-glucopyranosyluronate)]$_5$-(1→3)-2-acetamido-2-deoxy-D-glucopyranose).

(6-6) Measurement Results of HA14

500 MHz $^1$H-NMR δ; 2.001, 2.006, 2.016 (21H, NAc), 4.024 (dd, 0.6H, $J_{1,2}$=3.6 Hz, $J_{2,3}$=10.6 Hz, H-2aα), 4.439-

4.464 (m, H-1bβ, H-1d, H-1f, H-1h, H-1j, H-1l and H-1n), 4.498 (d, $J_{1,2}$=7.8 Hz, H-1bα), 4.537, 4.549 (d×2, $J_{1,2}$=8.4 Hz, $J_{1,2}$=8.3 Hz, H-1c, H-1e, H-1g, H-1i, H-1k and H-1m), 4.701 (d, $J_{1,2}$=8.4 Hz, H-1aβ), 5.141 (d, 0.6H, H-1aα)

Figure 34:
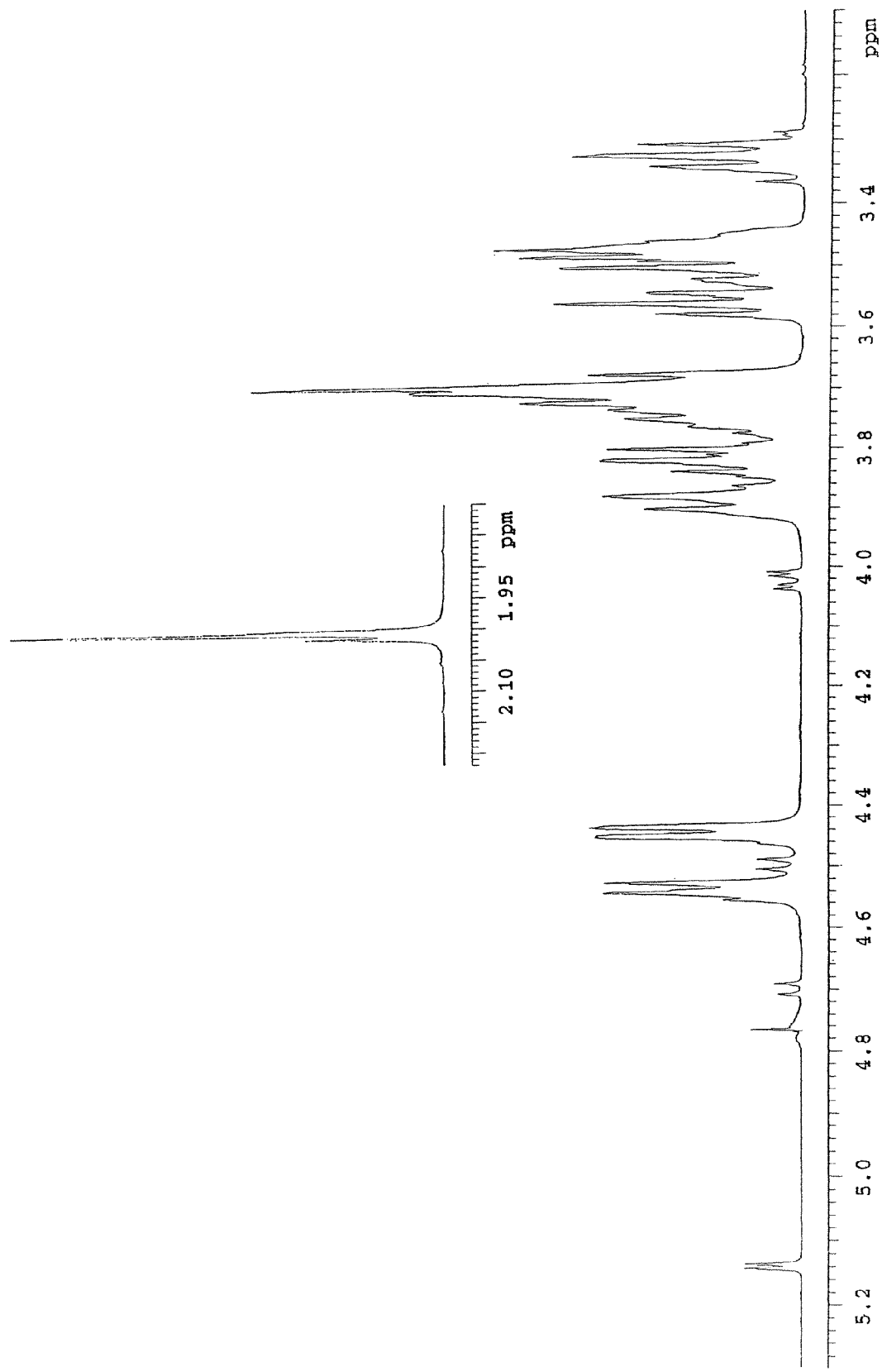
FIG. 34 shows $^1$H-NMR spectrum of HA14.

The spectrum used as the basis of the analysis is shown in FIG. 34.

125 MHz $^{13}$C-NMR δ; 24.84, 25.09, 25.34 (NHCOCH$_3$), 55.81 (C-2aα), 57.09, 57.15 (C-2c, C-2e, C-2g and C-2l), 58.43 (C-2aβ), 63.36, 63.57 (C-6a, C-6c, C-6e, C-6g and C-6l), 75.35, 75.58 (C-2b, C-2d, C-2f, C-2h and C-2j), 93.91 (C-1aα), 97.61 (C-1aβ), 103.40 (C-1c, C-1e, C-1g and C-1i), 105.80, 105.85, 105.94, 106.07 (C-1b, C-1d, C1f, C-1h and C-1j), 176.95, 177.40, 177.67, 177.80, 178.30 (carbonyl)

Figure 35:
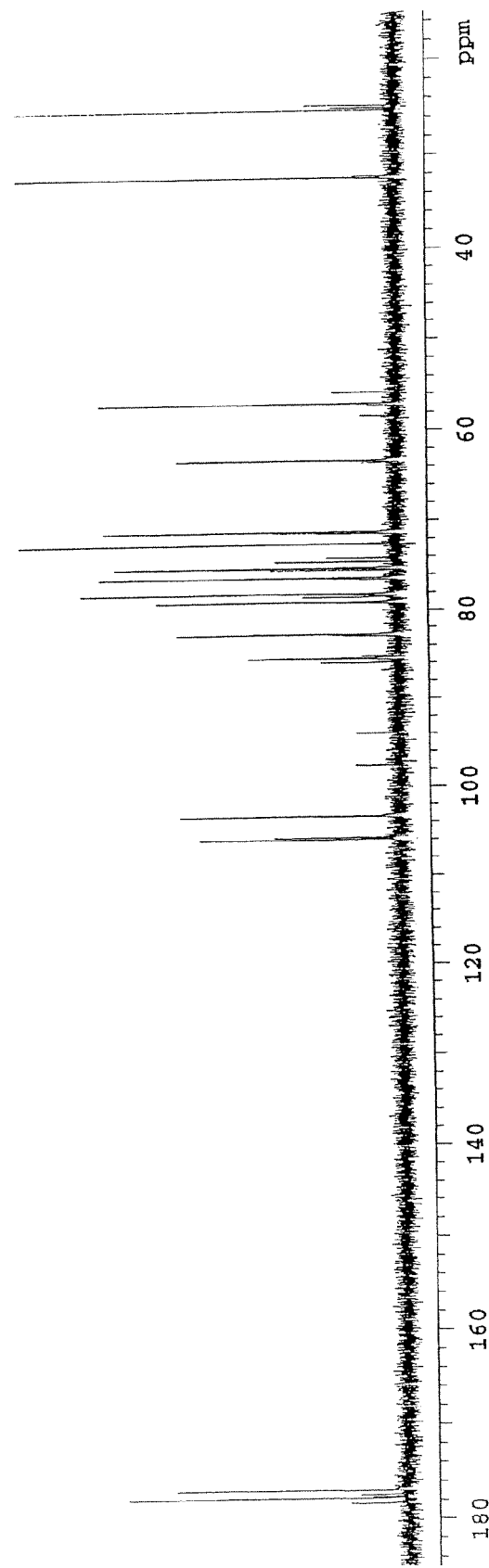
FIG. 35 shows $^{13}$C-NMR spectrum of HA14.
Figure 3:
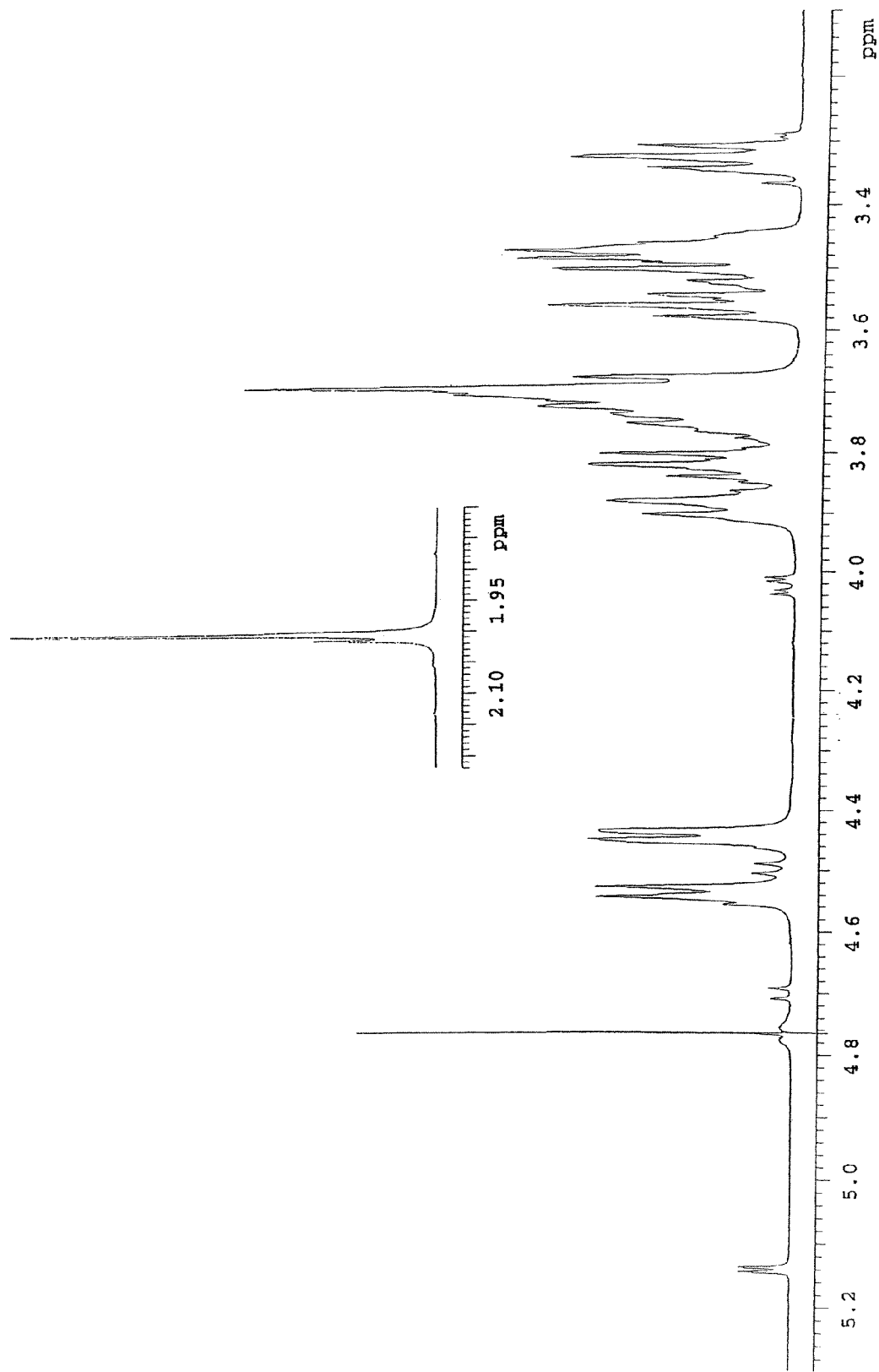

The spectrum used as the basis of the analysis is shown in FIG. 35.

These results are not contradictory to the structure represented by the aforementioned formula (1) wherein n=6 (structure of sodium β-D-glucopyranosyluronate-[(1→3)-2-acetamido-2-deoxy-β-D-glucopyranosyl-(1→4)-(sodium β-D-glucopyranosyluronate)]$_6$-(1→3)-2-acetamido-2-deoxy-D-glucopyranose).

(6-7) Measurement Results of HA16

500 MHz $^1$H-NMR δ; 2.002, 2.006, 2.016 (24H, NAc), 4.024 (dd, 0.6H, $J_{1,2}$=3.6 Hz, $J_{2,3}$=10.6 Hz, H-2aα), 4.434-4.464 (m, H-1bβ, H-1d, H-1f, H-1h, H-1j, H-1l, H-1n and H-1p), 4.498 (d, $J_{1,2}$=7.8 Hz, H-1bα), 4.537, 4.549 (d×2, $J_{1,2}$=8.4 Hz, $J_{1,2}$=8.3 Hz, H-1c, H-1e, H-1g, H-1i, H-1k, H-1m and H-1o), 4.701 (d, $J_{1,2}$=8.4 Hz, H-1aβ), 5.141 (d, 0.6H, H-1aα)

The spectrum used as the basis of the analysis is shown in FIG. 36.

125 MHz $^{13}$C-NMR δ; 24.84, 25.09, 25.35 (NHCOCH$_3$), 55.82 (C-2aα), 57.10, 57.16 (C-2c, C-2e, C-2g, C-2i, C-2k, C-2m and C-2o), 58.44 (C-2aβ), 63.37, 63.57 (C-6a, C-6c, C-6e, C-6g, C-6i, C-6k, C-6m and C-6o), 75.35, 75.58 (C-2b, C-2d, C-2f, C-2h, C-2j, C-2l, C-6n and C-6p), 93.92 (C-1aα), 97.61 (C-1aβ), 103.40 (C-1c, C-1e, C-1g, C-1i, C-1k, C-1m and C-1o), 105.80, 105.86, 105.95, 106.08 (C-1b, C-1d, C-1f, C-1h, C-1j, C-1l, C-1n and C-1p), 176.98, 177.41, 177.68, 177.81, 178.33 (carbonyl)

Figure 37:
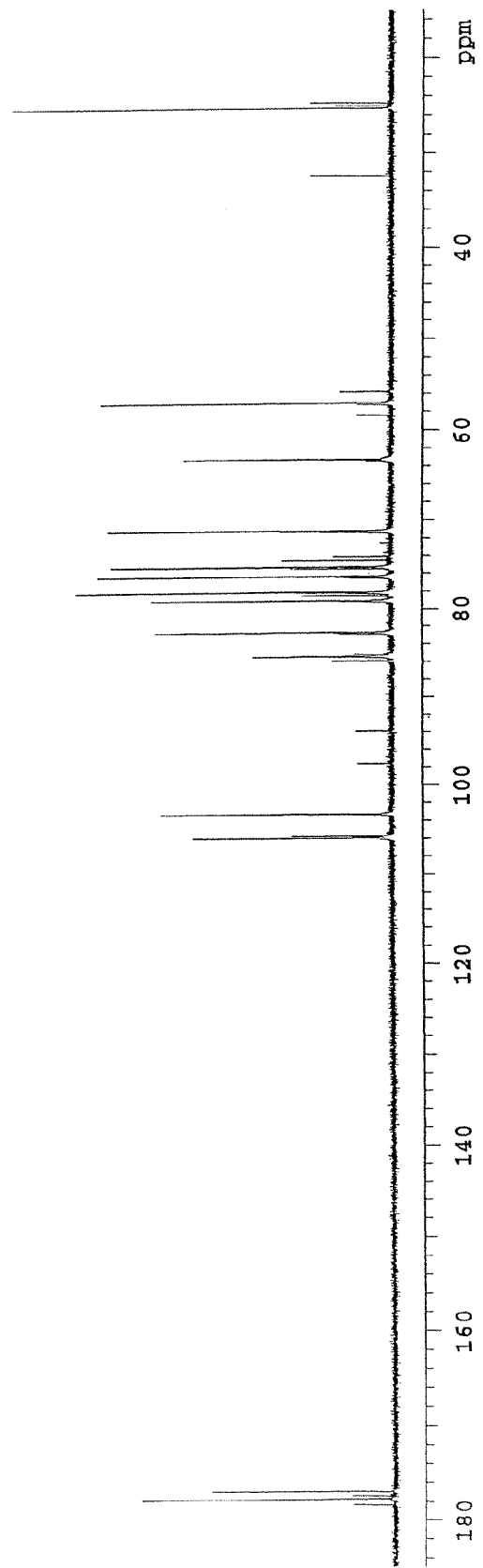
FIG. 37 shows $^{13}$C-NMR spectrum of HA16.

The spectrum used as the basis of the analysis is shown in FIG. 37.

These results are not contradictory to the structure represented by the aforementioned formula (1) wherein n=7 (structure of sodium β-D-glucopyranosyluronate-[(1→3)-2-acetamido-2-deoxy-β-D-glucopyranosyl-(1→4)-(sodium β-D-glucopyranosyluronate)]$_7$-(1→3)-2-acetamido-2-deoxy-D-glucopyranose).

(6-8) Measurement Results of HA48

500 MHz $^1$H-NMR δ; 1.998, 2.005, 2.016 (72H, NAc), 4.024 (dd, 0.6H, $J_{1,2}$=3.6 Hz, $J_{2,3}$=10.6 Hz, H-2aα), 4.395-4.470 (m, GlcA-unit), 4.498 (d, $J_{1,2}$=8.0 Hz, H-1bα), 4.537, 4.610 (d×2, $J_{1,2}$=8.2 Hz, $J_{1,2}$=7.8 Hz, GlcNAc-unit), 4.700 (d, $J_{1,2}$=8.3 Hz, H-1aβ), 5.141 (d, 0.6H, $J_{1,2}$=3.6 Hz, H-1aα)

Figure 38:
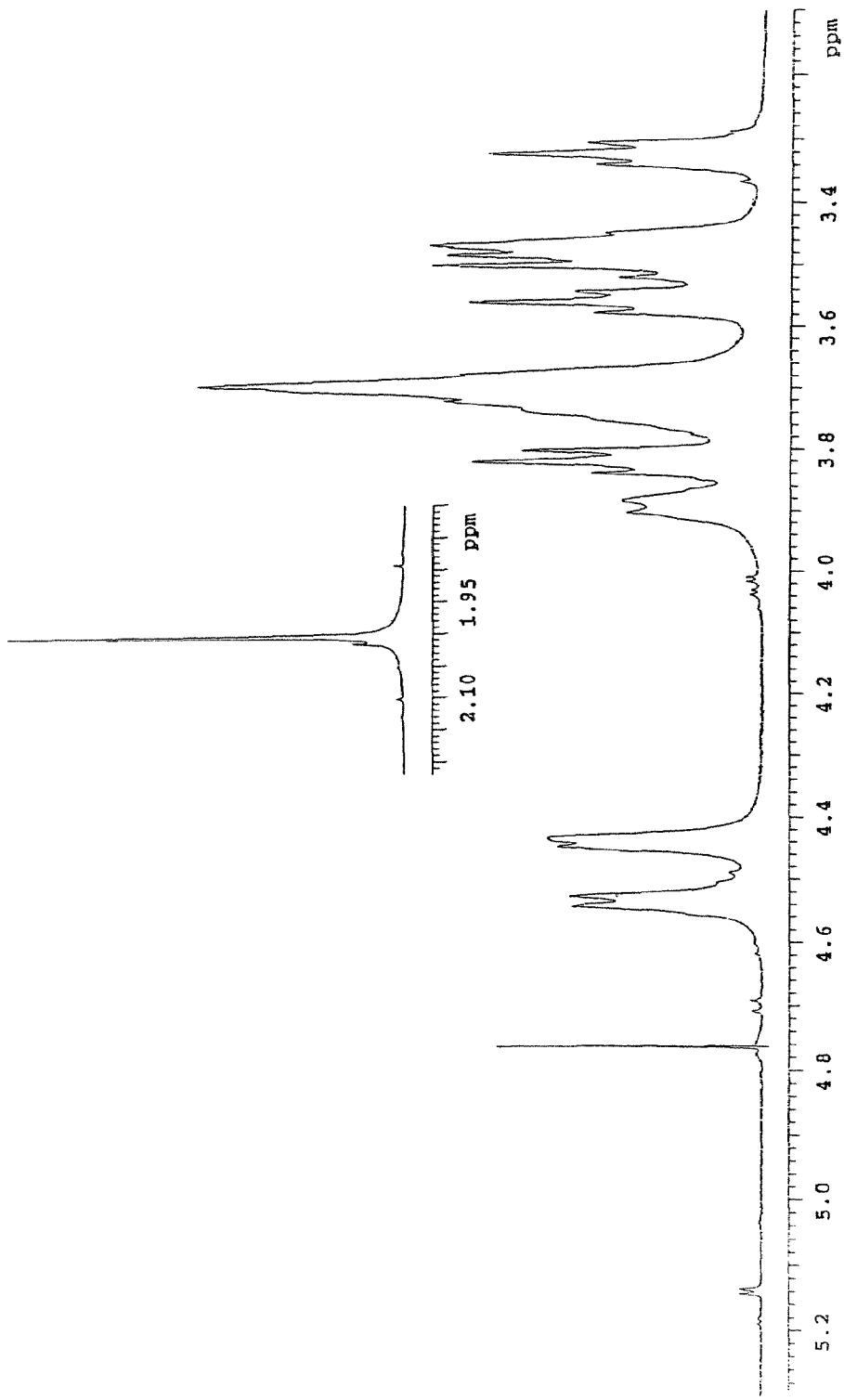
FIG. 38 shows $^1$H-NMR spectrum of HA48.

The spectrum used as the basis of the analysis is shown in FIG. 38.

These results are not contradictory to the structure represented by the aforementioned formula (1) wherein n=23 (structure of sodium β-D-glucopyranosyluronate-[(1→3)-2-acetamido-2-deoxy-β-D-glucopyranosyl-(1→4)-(sodium β-D-glucopyranosyluronate)]$_{23}$-(1→3)-2-acetamido-2-deoxy-D-glucopyranose).

(6-9) Measurement Results of HA50

500 MHz $^1$H-NMR δ; 2.005, 2.017 (75H, NAc), 4.024 (dd, 0.6H, $J_{1,2}$=3.6 Hz, $J_{2,3}$=10.6 Hz, H-2aα), 4.390-4.470 (m, GlcA-unit), 4.498 (d, $J_{1,2}$=7.9 Hz, H-1bα), 4.537, 4.610 (d×2, $J_{1,2}$=8.1 Hz, $J_{1,2}$=8.1 Hz, GlcNAc-unit), 4.701 (d, $J_{1,2}$=8.4 Hz, H-1aβ), 5.141 (d, 0.6H, $J_{1,2}$=3.6 Hz, H-1aα)

Figure 39:
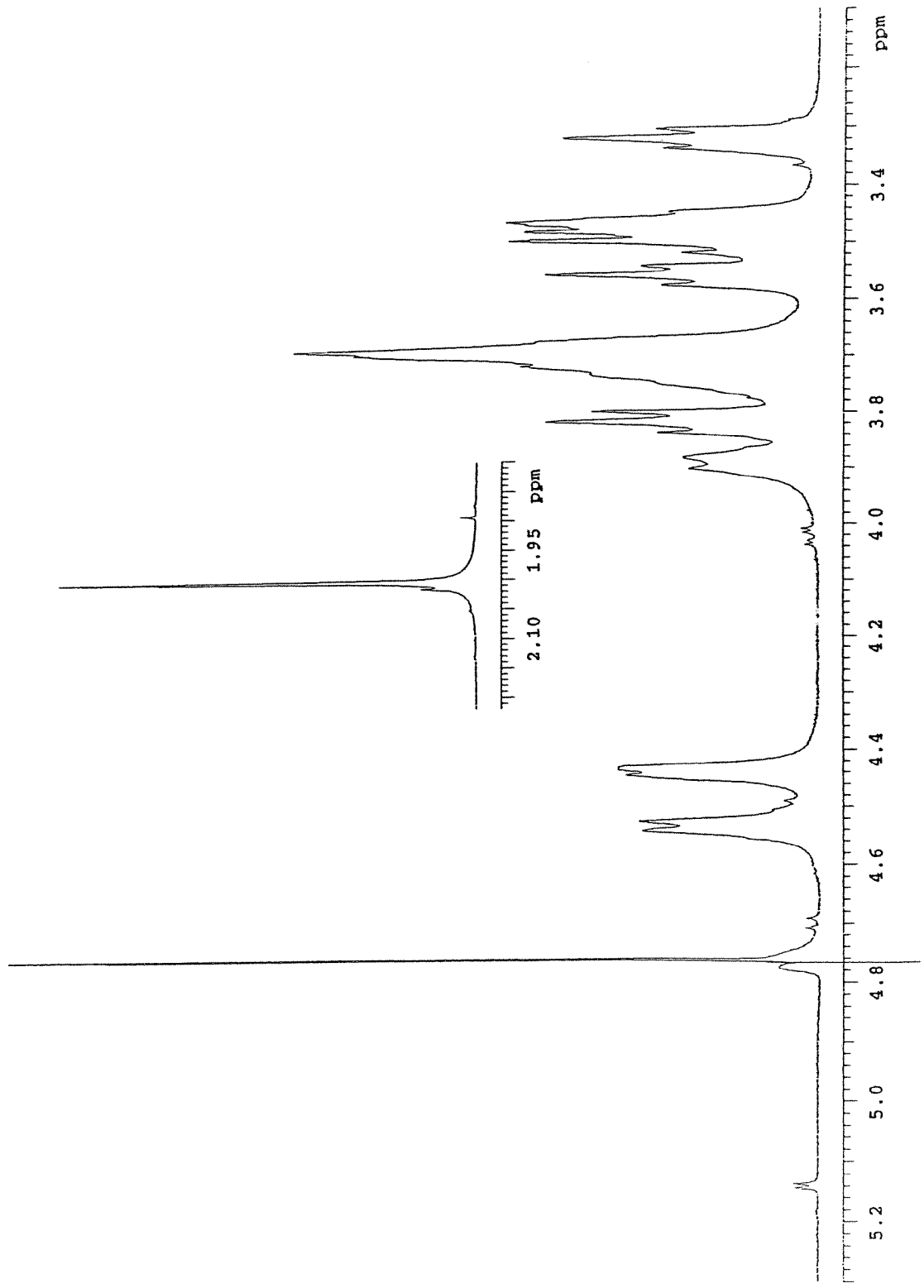
FIG. 39 shows $^1$H-NMR spectrum of HA50.

The spectrum used as the basis of the analysis is shown in FIG. 39.

These results are not contradictory to the structure represented by the aforementioned formula (1) wherein n=24 (structure of sodium β-D-glucopyranosyluronate-[(1→3)-2-acetamido-2-deoxy-β-D-glucopyranosyl-(1→4)-(sodium β-D-glucopyranosyluronate)]$_{24}$-(1→3)-2-acetamido-2-deoxy-D-glucopyranose).

(6-10) Measurement Results of HA52

500 MHz $^1$H-NMR δ; 2.005, 2.017 (78H, NAc), 4.024 (dd, 0.6H, $J_{1,2}$=3.6 Hz, $J_{2,3}$=10.6 Hz, H-2aα), 4.375-4.475 (m, GlcA-unit), 4.498 (d, $J_{1,2}$=8.2 Hz, H-1bα), 4.536, 4.610 (d×2, $J_{1,2}$=8.1 Hz, $J_{1,2}$=8.1 Hz, GlcNAc-unit), 4.701 (d, $J_{1,2}$=8.4 Hz, H-1aβ), 5.141 (d, 0.6H, $J_{1,2}$=3.4 Hz, H-1aα)

Figure 40:
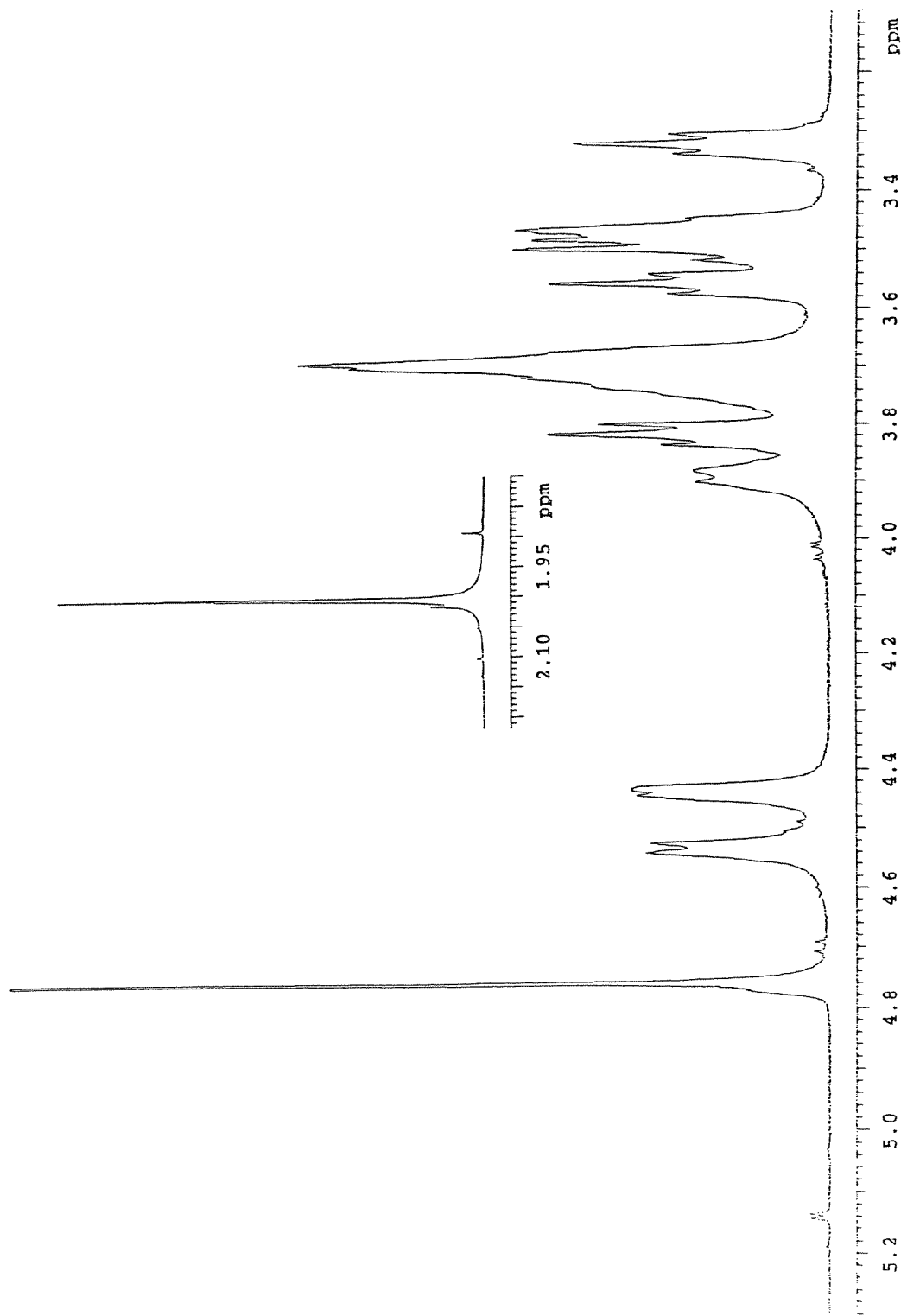
FIG. 40 shows $^1$H-NMR spectrum of HA52.
Figure 4:
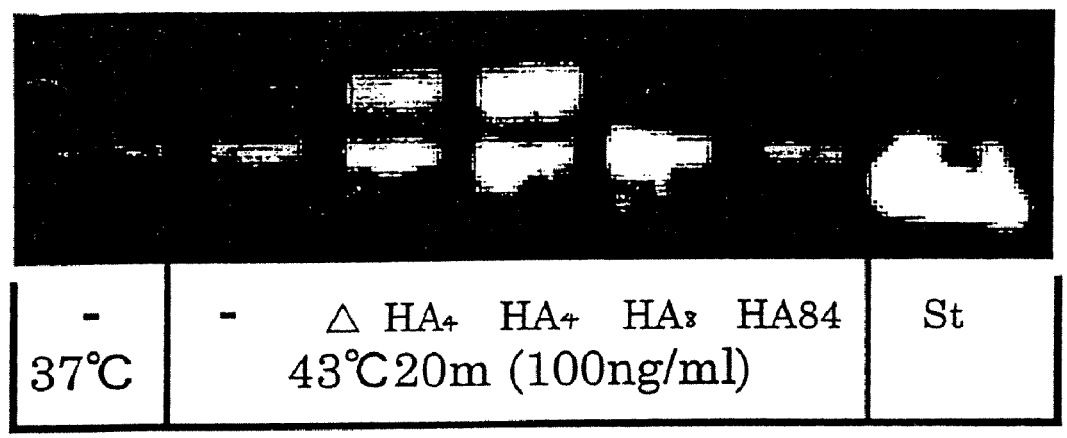

The spectrum used as the basis of the analysis is shown in FIG. 40.

These results are not contradictory to the structure represented by the aforementioned formula (1) wherein n=25 (structure of sodium β-D-glucopyranosyluronate-[(1→3)-2-acetamido-2-deoxy-β-D-glucopyranosyl-(1→4)-(sodium β-D-glucopyranosyluronate)]$_{25}$-(1→3)-2-acetamido-2-deoxy-D-glucopyranose).

(7) Impurities Other than HA Oligosaccharides

Contents of the following impurities in the fractions were measured.

(7-1) Protein

Protein content was measured by using BioRad Protein Assay kit (produced by BioRad) and bovine serum albumin as a standard substance.

(7-2) DNA

DNA content was measured by the threshold method (DNA measuring apparatus: Threshold (Molecular Device, U.S.A.).

(7-3) Endotoxin

Endotoxin content was measured by the Limulus test method using Toxycolor System (trade name, produced by Seikagaku Corporation).

The measurement results for the protein, DNA and endotoxin contents in the fractions are shown in Table 7.

TABLE 7

| Sample | Protein (%) | DNA | Endotoxin (pg/mL) |
|---|---|---|---|
| HA4 | Below detection limit | Below detection limit | 0.5 |
| HA6 | Below detection limit | Below detection limit | 0.1 |
| HA8 | Below detection limit | Below detection limit | 0.1 |
| HA10 | Below detection limit | Below detection limit | 0.7 |
| HA12 | Below detection limit | Below detection limit | 0.1 |
| HA14 | Below detection limit | Below detection limit | 0.3 |

From these results, it was concluded that the contents of protein and DNA in the fractions of the present invention were all below detection limit, the contents of endotoxin were all at a level that did not substantially influence, and thus they did not substantially contain them.

EXAMPLE 2

Hsp Expression Promoting Action

<Materials Etc.>

(1) Test Substances Etc.

The test substances used in this example etc. are explained first.

Test substance (the abbreviations mentioned in the parentheses are used in the following descriptions. In the following formulas, GlcA stands for a glucuronic acid residue, GlcNAc for an N-acetylglucosamine residue, Gal for a galactose residue, (6S) for 6-O-sulfate and - for a glycosidic linkage, and Δ indicates that the saccharide is an unsaturated saccharide.

Saturated HA disaccharide (HA2)
GlcAβ1-3GlcNAc
Unsaturated HA disaccharide (ΔHA2)
ΔGlcAβ1-3GlcNAc
Saturated HA tetrasaccharide (HA4)
GlcAβ1-3GlcNAcβ1-4GlcAβ1-3GlcNAc
Unsaturated HA tetrasaccharide (ΔHA4)
ΔGlcAβ1-3GlcNAcβ1-4GlcAβ1-3GlcNAc
Saturated HA hexasaccharide (HA6)
GlcAβ1-3GlcNAcβ1-4GlcAβ1-3GlcNAcβ1-4GlcAβ1-3GlcNAc
Unsaturated HA hexasaccharide (ΔHA6)
ΔGlcAβ1-3GlcNAcβ1-4GlcAβ1-3GlcNAcβ1-4GlcAβ1-3GlcNAc
Saturated HA octasaccharide (HA8)
GlcAβ1-3GlcNAcβ1-4GlcAβ1-3GlcNAcβ1-4GlcAβ1-3GlcNAcβ1-4GlcAβ1-3GlcNAc
Saturated HA decasaccharide (HA10)
GlcAβ1-3GlcNAcβ1-4GlcAβ1-3GlcNAcβ1-4GlcAβ1-3GlcNAcβ1-4GlcAβ1-3GlcNAcβ1-4GlcAβ1-3GlcNAc
Saturated HA dodecasaccharide (HA12)
GlcAβ1-3GlcNAcβ1-4GlcAβ1-3GlcNAcβ1-4GlcAβ1-3GlcNAcβ1-4GlcAβ1-3GlcNAcβ1-4GlcAβ1-3GlcNAcβ1-4GlcAβ1-3GlcNAc
Mixture of Saturated HA disaccharide to octadecasaccharide (HA2-18)
Mixture of Saturated HA octadecasaccharide to tetradecasaccharide (HA 8-14)
HA (weight average molecular weight: 840,000, HA84)
Gal(6S)β1-4GlcNAc(6S) (L4)
Gal(6S)β1-4GlcNAc(6S)β1-3Gal(6S)β1-4GlcNAc (6S) (L4L4)

As the saturated HA oligosaccharides, the HA oligosaccharide fractions produced in Preparation Example 1 mentioned above were used.

The unsaturated HA oligosaccharides were obtained by treating HA with chondroitin AC-1 lyase (Chondroitinase ACI Flavo, produced by Seikagaku Corporation) and fractionating the decomposition product in the same manner as in Preparation Example 1 (refer to Preparation Example 2).

L4 and L4L4 were prepared by the method described in International Patent Publication WO96/16973.

The test substances were dissolved in physiological saline to a concentration predetermined according to the following pharmaceutical efficacy tests. Endotoxin concentrations of the solutions in physiological saline were all below 0.3 EU/mL, and iron contents of the same were all 20 ppm or less.

(2) Cell and Medium

K562 Cell (JCRB0019, Human Leukemia Cell) and PC-12 Cell (JCRB0733)

K562 cells were cultured in RPMI 1640 medium containing 10% fetal bovine serum (FBS).

PC-12 cells were cultured in a medium obtained by adding 10 mL of 20% aqueous solution of glucose to 575 mL of DMEM medium (containing D-glucose (1,000 mg/l), L-glutamine (4 mM), sodium pyruvate (110 mg/l) and sodium bicarbonate (3.7 g/l)) containing 10% equine serum and 5% neonatal calf serum (FCS).

<1> Action on Phosphorylation of HSF1

It is known that HSF1 (heat shock factor 1) protein is a transcription factor of Hsp70 (J. Biol. Chem., 271, pp. 3355-3358, 1996). Moreover, the HSF1 protein can be activated by phosphorylation, and this phosphorylation can be detected based on band shift in SDS-polyacrylamide gel electrophoresis (SDS-PAGE) (apparent molecular weight shifts from about 66 kDa to about 81 kDa). By utilizing this fact, the HA oligosaccharides of various sizes were allowed to act on the K562 cells given with stress, and the aforementioned band shift was detected to investigate the degree of the phosphorylation (activation) of HSF1.

(1) Experiment 1

HA4, ΔHA4, HA6, HA8, HA2-18 and HA 8-14 were each added to a medium containing the aforementioned cells at a concentration of 1, 10 or 100 ng/mL. Then, the cells were immediately transferred into an environment at 42° C. to be given with heat shock and incubated for 20 minutes. After the incubation, the cells were collected by centrifugation, and SDS-PAGE (gel concentration: 10%) was performed. Thereafter, Western blotting was performed by using anti-HSF1 monoclonal antibodies (produced by Stressgene) as primary antibodies and goat anti-mouse IgG monoclonal antibodies (produced by Jackson Lab) as secondary antibodies to detect the shift of a band of 66 kDa (HSF1 not phosphorylated) to a band of 81 kDa (phosphorylated HSF1).

As a result, in the cells added with HA4, ΔHA4, HA6 or HA2-18, the shift to the 81 kDa band was observed depending on the amount of the added HA oligosaccharide. Definite shift was not seen with HA8-14. Conversely, inhibition of the band shift was observed with HA8.

(2) Experiment 2

In order to confirm the reproducibility of Experiment 1, the band shift was detected in the same manner as in Experiment 1 by using HA4, ΔHA4, HA8 and HA84 except that HA was added in a single kind of amount of 100 ng/mL and the heat shock was given at 43° C. The results are shown in FIG. 41. In FIG. 41, the first lane from the left indicates the result obtained with an extract of cells incubated at 37° C. (no addition of HA oligosaccharide), the second lane indicates the result obtained with an extract of cells subjected to 43° C. (no addition of HA oligosaccharide), and the first lane from the right indicates the result of detection of HSF1 (derived from bacteria) as a standard.

As seen from the result shown in FIG. 41, the band shift was observed for the cells added with HA4 or ΔHA4, and the amounts of both HSF1 of 66 kDa and 81 kDa per se were also increased. On the other hand, with HA8, increase of the amount of HSF1 of 66 kDa was observed, whereas the band shift to the band of 81 kDa was not observed. Moreover, the shift was not seen with HA84.

(3) Experiment 3 (Comparative Experiment)

In order to investigate whether the action observed in Experiment 2 was specific to the saccharide chain basic structure of HA oligosaccharides, the following comparative experiment was performed by using chondroitin oligosaccharides. Chondroitin (referred to as Ch hereinafter) is different from HA only in that GlcNAc in HA is replaced with a galactosamine residue (GalNAc), and they have common characteristics that they are commonly glycosaminoglycans, they do not have a sulfate group etc. Therefore, it can be said that Ch is a substance extremely structurally analogous to HA, and the same shall also apply to the oligosaccharides thereof.

Saturated Ch tetrasaccharide (Ch4)
GlcAβ1-3GalNAcβ1-4GlcAβ1-3GalNAc

Saturated Ch hexasaccharide (Ch6)
GlcAβ1-3GalNAcβ1-4GlcAβ1-3GalNAcβ1-4GlcAβ1-3GalNAc Saturated Ch octasaccharide (Ch8)
GlcAβ1-3GalNAcβ1-4GlcAβ1-3GalNAcβ1-4GlcAβ1-3GalNAcβ1-4GlcAβ1-3GalNAc These saturated Ch oligosaccharides were obtained by treating Ch with dimethyl sulfoxide (DMSO) containing HCl and fractionating the obtained decomposition product for each size through anion exchange chromatography according to the method of Nagasawa et al. (Carbohyd. Res., 141, pp. 99-110, 1985).

The same experiment as Experiment 2 was performed by using these oligosaccharides. As a result, the band shift of HSF1 or increase of the amount of HSF1 per se was not observed for any cells added with the Ch oligosaccharides.

By this experiment, it was demonstrated that the Ch oligosaccharides did not have actions for activating HSF1 and promoting expression of HSF1, which were observed for the HA oligosaccharides. This indicates that such actions should be specific to the saccharide chain basic structures of HA oligosaccharides.

By these experiments, it was revealed that the HA tetrasaccharide and a fraction containing it (HA2-18) particularly notably activated HSF1.

<2> Action on Expression of Hsp

Since it was revealed from <1> that the HA tetrasaccharide more notably activated the factor required for the expression of Hsp70 (HSF1) compared with HA of other sizes, the following experiment was performed in order to investigate whether the expression of Hsp in K562 cells given with stress should be actually increased more notably by the action of HA tetrasaccharide compared with cases utilizing HA of other sizes.

HA2, ΔHA4, HA6, HA84 and L4L4 were each added to a medium containing the aforementioned cells (37° C.) at a concentration of 1, 10 or 100 ng/mL. Then, the cells were immediately transferred into an environment at 43° C. to be given with heat shock and incubated for 20 minutes. Then, the cells were returned to 37° C., then further incubated for 2 hours and collected by centrifugation, and SDS-PAGE was performed in the same manner as in <1> mentioned above. Thereafter, Western blotting was performed by using anti-Hsp72 monoclonal antibodies (produced by Amersham) as primary antibodies and goat anti-rabbit IgG monoclonal antibodies (produced by Jackson Lab) as secondary antibodies to detect Hsp72. Hsp72 is one of the members of Hsp70 family and is the most typical one, and it is known that its expression is induced and promoted by stress.

Figure 42:
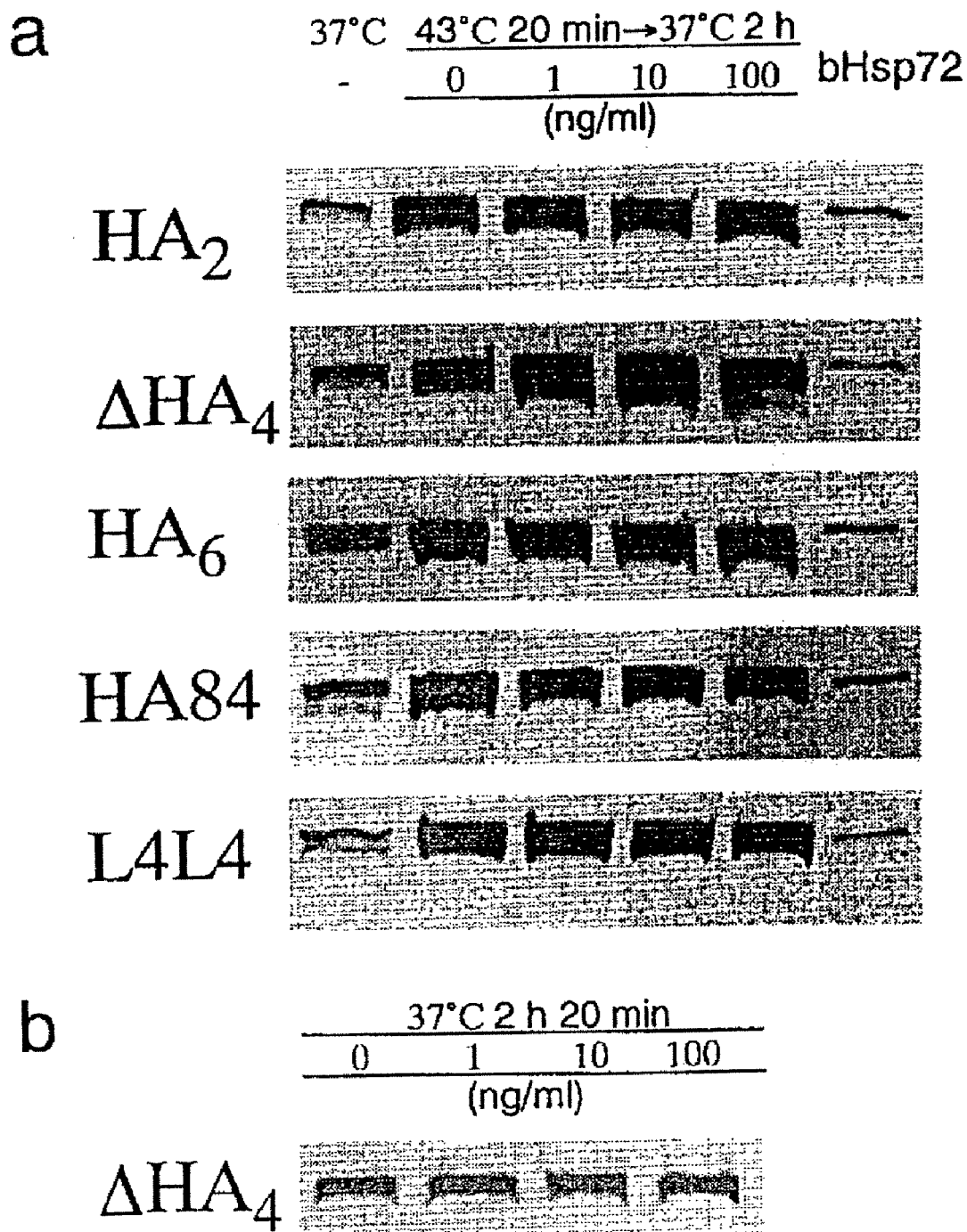
FIG. 42 shows expression of Hsp72 induced by HA tetrasaccharide after heat shock.

The results are shown in FIG. 42. The leftmost lane in FIG. 42a indicates the results of the detection of Hsp72 in a similar manner with giving no heat shock (37° C.) and addition of no test substance, and the rightmost lane indicates the results of detection of standard Hsp72 (Hsp72 derived from bacteria, bHsp72) in a similar manner. FIG. 42b shows the results of detection of the expression of Hsp72 in a similar manner with addition of ΔHA4 to the cells that were not given with heat shock.

As clearly seen from the results shown in FIG. 42a, when a heat shock (43° C.) was given (the second lane from the left), the expression of Hsp was enhanced compared with the case where a test substance was not added at 37° C. (the leftmost lane). Further, in the presence of each of the HA oligosaccharides, the expression of Hsp was further enhanced, and the expression of Hsp was particularly strongly enhanced in the presence of ΔHA4 (the third to fifth lanes from the left).

Thus, strong expression of Hsp72 was observed in the cells added with ΔHA4 (given with the heat shock), whereas such strong expression of Hsp72 as in the cells added with ΔHA4 was not observed in the cell added with HA of other sizes.

Moreover, in the cells that were not given with the heat shock, enhancement of the expression of Hsp72 by ΔHA4 was not observed. From this fact, it was revealed that, although the HA tetrasaccharide scarcely affect the expression of Hsp under no stress condition, it extremely quickly and notably enhance the expression of Hsp if stress is once loaded.

<3> Cell Death Inhibitory Action

Since it was revealed that the HA tetrasaccharide more strongly enhanced the expression of Hsp in the cells under stress compared with HA oligosaccharides of other sizes, the following experiment was performed in order to investigate whether the HA oligosaccharides actually suppressed death of cells subjected to stress more strongly or not.

It is known that the PC-12 cells suffer from apoptosis in a culture broth that does not contain blood serum.

Therefore, each of ΔHA2, HA4, ΔHA4, HA6, ΔHA6, HA8, HA10, HA12, HA84, L4 and L4L4 was added to a culture broth containing PC-12 cells at a concentration of 100 ng/mL (containing no blood serum), 24 hours after, the cells were stained with trypan blue, and a ratio of the number of viable cells (cells not stained with trypan blue) to the total cell number was calculated.

Figure 43:
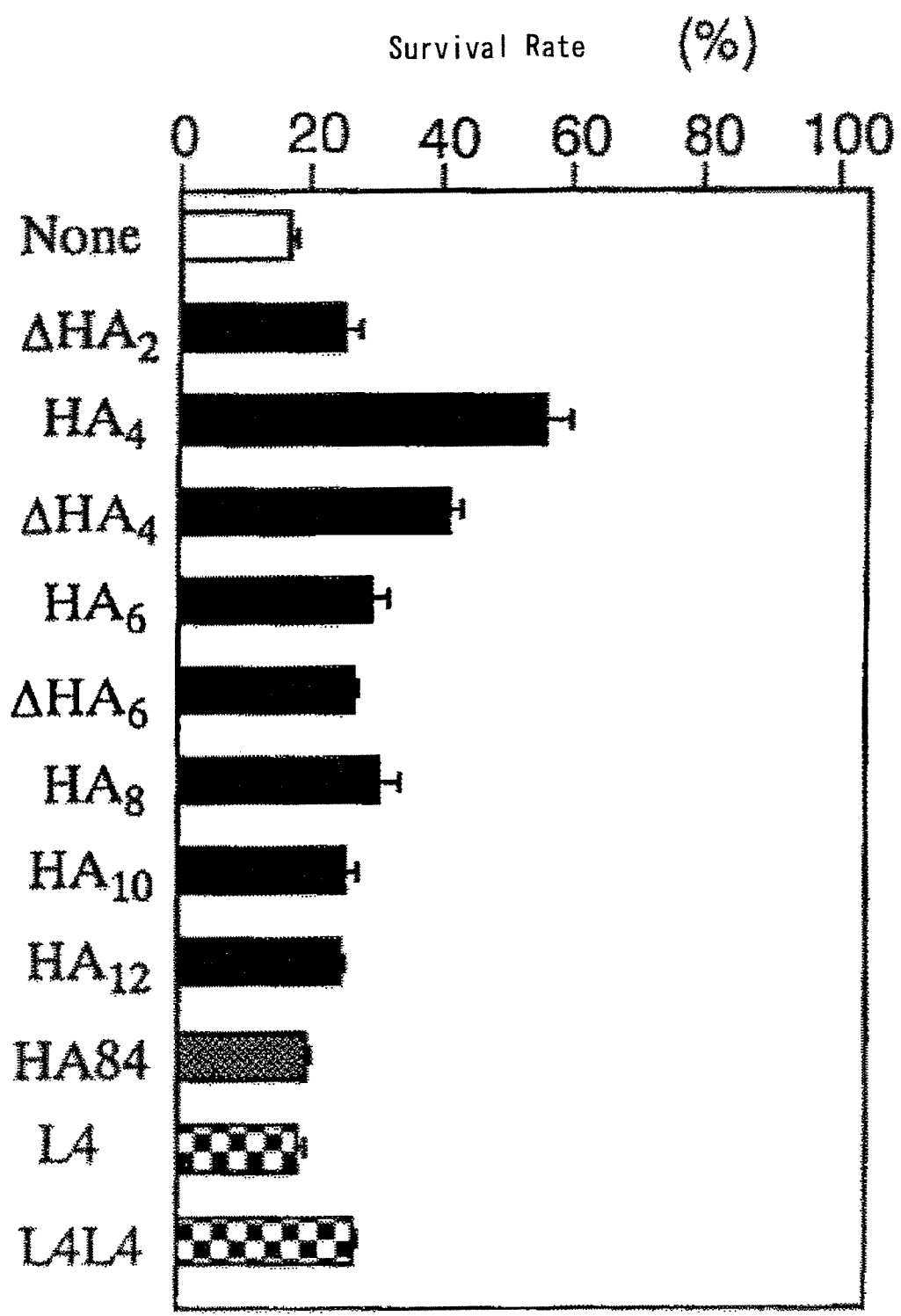
FIG. 43 shows degrees of suppression of cell death (apoptosis) induced by serum starvation obtained with various HA oligosaccharides.

The results are shown in FIG. 43. As seen from the results shown in FIG. 43, the HA tetrasaccharides, especially HA4, more notably suppressed the cell death compared with HA oligosaccharides of other sizes or the oligosaccharides of other kinds.

<4> Cell and Tissue Protection Action

1. Cell and tissue protection action in Organ preservation aspect (1) Preparation of Organ Preservation Solution A Euro-Collins solution (Am. J. Surg., 179, pp. 154-160, 2000) containing 100 ng/mL of HA tetrasaccharide was used as a test solution (also referred to as "HA4(+)" hereafter). As a control, the Euro-Collins solution (also referred to as "HA4(−)" hereafter) was used.

(2) Administration of Test Substance Etc.

SD male rats of 11-week old were divided into a "HA4(+) used" group (n=5), "HA4(−) used" group (n=5) and normal group (n=5). After abdominal section, organs (livers) were extracted. The organs of the "HA4(+) used" group and "HA4(−) used" group were perfused with 40 mL of each solution until the color of the whole livers became light due to bleeding and then incubated at 37° C. for 2 hours.

(3) Evaluation

After the incubation, for each group, a ratio of wet weight/dry weight of organ (parameter of degree of edema caused by tissue affection) was calculated, a HE-stained tissue section was observed by using an optical microscope (visual inspection of tissue affection), and image analysis of chromatin concentration and analysis by the TUNEL method (terminal deoxynucleotidyl transferase (TdT)-mediated nick end labeling method, J. Cell. Biol., 119, pp. 493-501, 1992, evaluation of degree of cell death) were performed.

(3-1)

Figure 44:
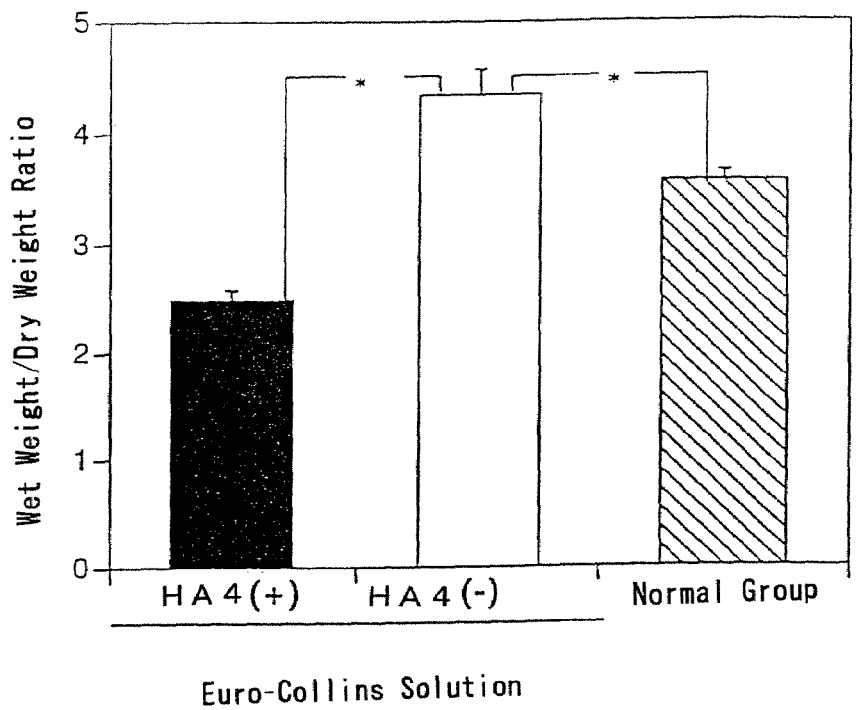
FIG. 44 shows edema suppression effect of HA tetrasaccharide in an organ.

The results for the ratio of wet weight/dry weight of organ are shown in FIG. 44. The symbol of * in FIG. 44 indicates the presence of significant difference with p<0.05 (Williams multiple range test).

As seen from the results shown in FIG. 44, the ratio of wet weight/dry weight of organ was significantly decreased in the "HA4(+)" used group compared with the "HA4(−)" used group. This indicated that the HA tetrasaccharide significantly suppressed edema due to tissue affection caused by preservation of organ.

(3-2)

As a result of the observation of HE-stained tissue section by using an optical microscope, edema, histolysis (disappearance of plasma), pyknosis etc. were observed in the "HA4(−)" used group. On the other hand, images substantially similar to those of the normal group were observed for the "HA4(+)" used group, and remarkable tissue affection, which was observed for the "HA4(−)" used group, was not observed.

(3-3) Image Analysis for Chromatin Concentration

As one method for evaluating degree of cell death, image analysis of cellular chromatin concentration was performed (Image-Pro PLUS™ Version 3.0.1, produced by Media Cybernetics) by using HE-stained tissue sections to compare image densities. If cell death occurs and chromatin is concentrated, that portion will be deeply stained with HE. If there are more cells in which chromatin is concentrated, density of the whole microscopic image is increased. Therefore, the evaluation was performed by using the density as an index.

Figure 45:
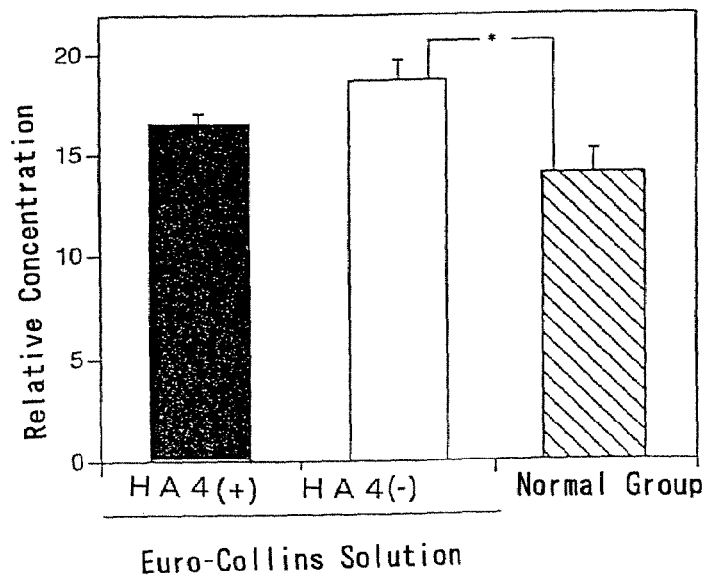
FIG. 45 shows cellular chromatin concentration inhibitory effect of HA tetrasaccharide.
Figure 4:
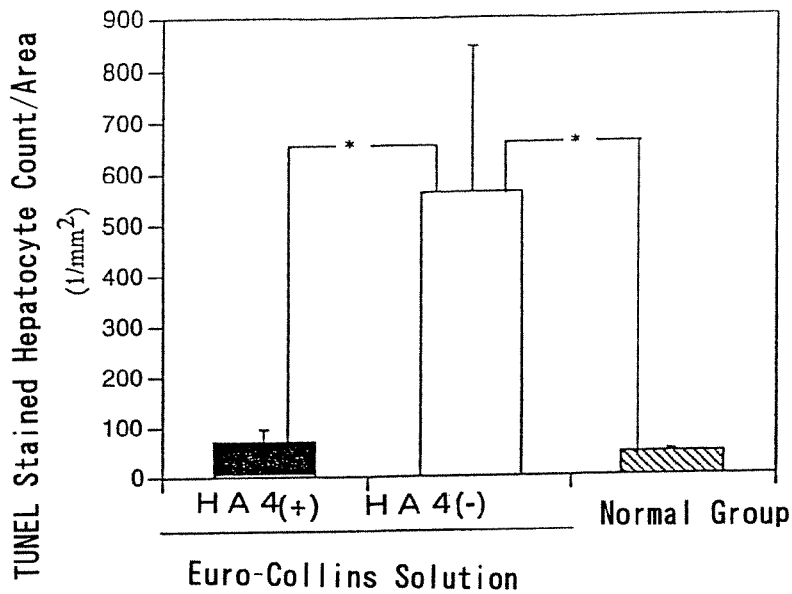
Figure 4:
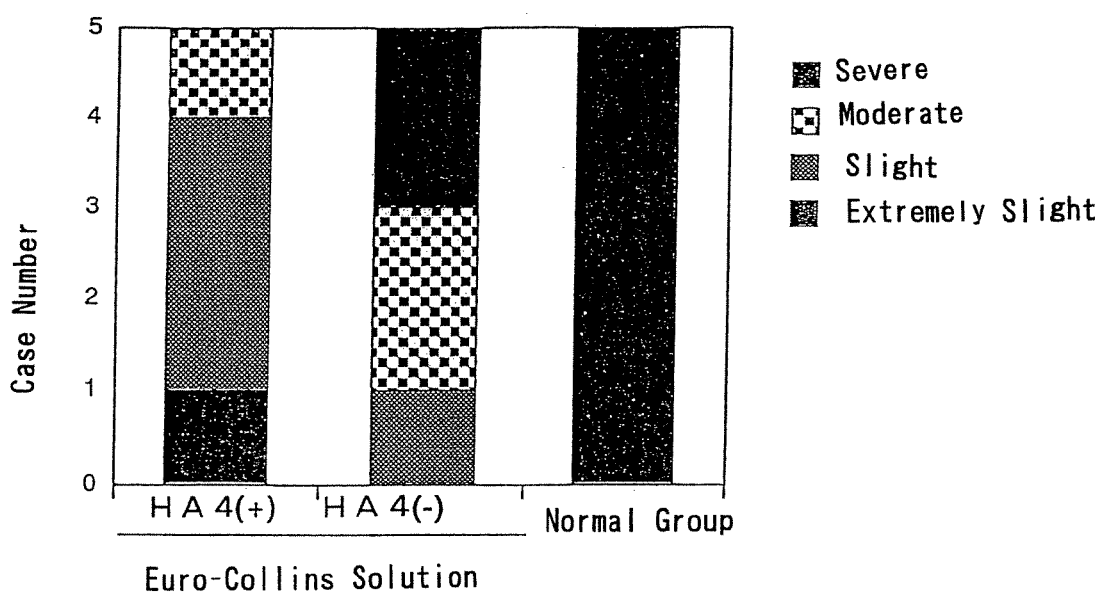

The results are shown in FIG. 45. The symbol of * in FIG. 45 indicates the presence of a significant difference with p<0.05 (Williams multiple range test).

As seen from the results shown in FIG. 45, the image density was significantly increased in the "HA4(−)" used group compared with the normal group, whereas significant increase of the image density was not observed for the "HA4(+)" used group compared with the normal group.

(3-4) Analysis by TUNEL Method

As one method for evaluating degree of cell death, degree of fragmentation of DNA was analyzed by using the TUNEL method. It is known that, if a cell causes apoptosis, DNA is fragmented. The TUNEL method is a method for staining termini of DNA, and if there are many cells in which DNA is fragmented, degree of TUNEL staining is increased. Therefore, it can be used as an index of the degree of cell death (apoptosis).

Tissue sections after storage were subjected to the TUNEL staining and visually inspected by using an optical microscope to count the number of cells stained by the TUNEL method per 1 mm$^2$. At the same time, the degree of tissue affection of the tissue sections was evaluated with four grades including "severe", "moderate", "slight" and "extremely slight". In addition, this evaluation was performed as a blind test in order to secure objectivity. The results of the former are shown in FIG. 46, and the results of the latter are shown in FIG. 47. The symbol of * in FIG. 46 indicates the presence of significant difference with p<0.05 (Williams multiple range test).

As seen from the results shown in FIG. 46, an extremely large number of TUNEL-stained cells were observed for the "HA4(−)" used group, whereas TUNEL-stained cells observed for the "HA4(+)" used group were extremely few and the number was at a level similar to that of the normal group. Further, as seen from the results shown in FIG. 47, "severe" or "moderate" tissue affection was observed in 80% of the tissue sections in the "HA4(−)" used group, whereas "severe" tissue affection was not observed and "moderate" tissue affection was observed only in 20% of the tissue sections in the "HA4(+)" used group.

Based on the results mentioned above, it was revealed that the HA oligosaccharide (HA tetrasaccharide) had superior cell and tissue protection effect in the organ preservation aspect.

2. Cell and tissue protection action in aspect of effect on ulcer (1) Preparation of Test Solutions for Administration A test substance was dissolved in carboxymethylcellulose (CMC) to obtain a test solution for administration. The concentration was determined depending on the dose mentioned below so that the volume of the solution to be administered should become 10 mL/kg.

Moreover, as a positive control solution, a conventional agent for treating gastritis and gastric ulcer (teprenone, geranylgeranylacetone, trade name: Selbex, Eisai) dissolved in CMC was used. The concentration was determined so that the dose and the volume of the solution to be administered should become 1 mg/kg (clinical dose) and 10 mL/kg, respectively. As a negative control solution, 0.5% CMC was used.

(2) Administration of Test Substance Etc.

SD male rats of 5-week old were divided into a "negative control solution" administered group (n=8), "HA4 4 mg/kg" administered group (n=8), "HA4 20 mg/kg" administered group (n=8), "HA4 100 mg/kg" administered group (n=8) and "positive control solution" administered group (n=8).

The rats of the groups were starved from 16:00 of the day before the first administration day, orally administered with each of the aforementioned solutions at 8:00 of the next day and arrested by water immersion. The arrest by water immersion was continued until 8:00 of the next day (24 hours). In the course of the arrest, each solution was administered in the same manner as the first administration at 16:00 and 24:00.

Then, the rats were dissected, and the stomachs were extracted. The extracted stomachs were expanded by injection of 10% buffered formalin to smoothen the holds and fixed. Then, the blood adhering to walls of stomachs was removed by washing with water.

(3) Evaluation

Figure 48:
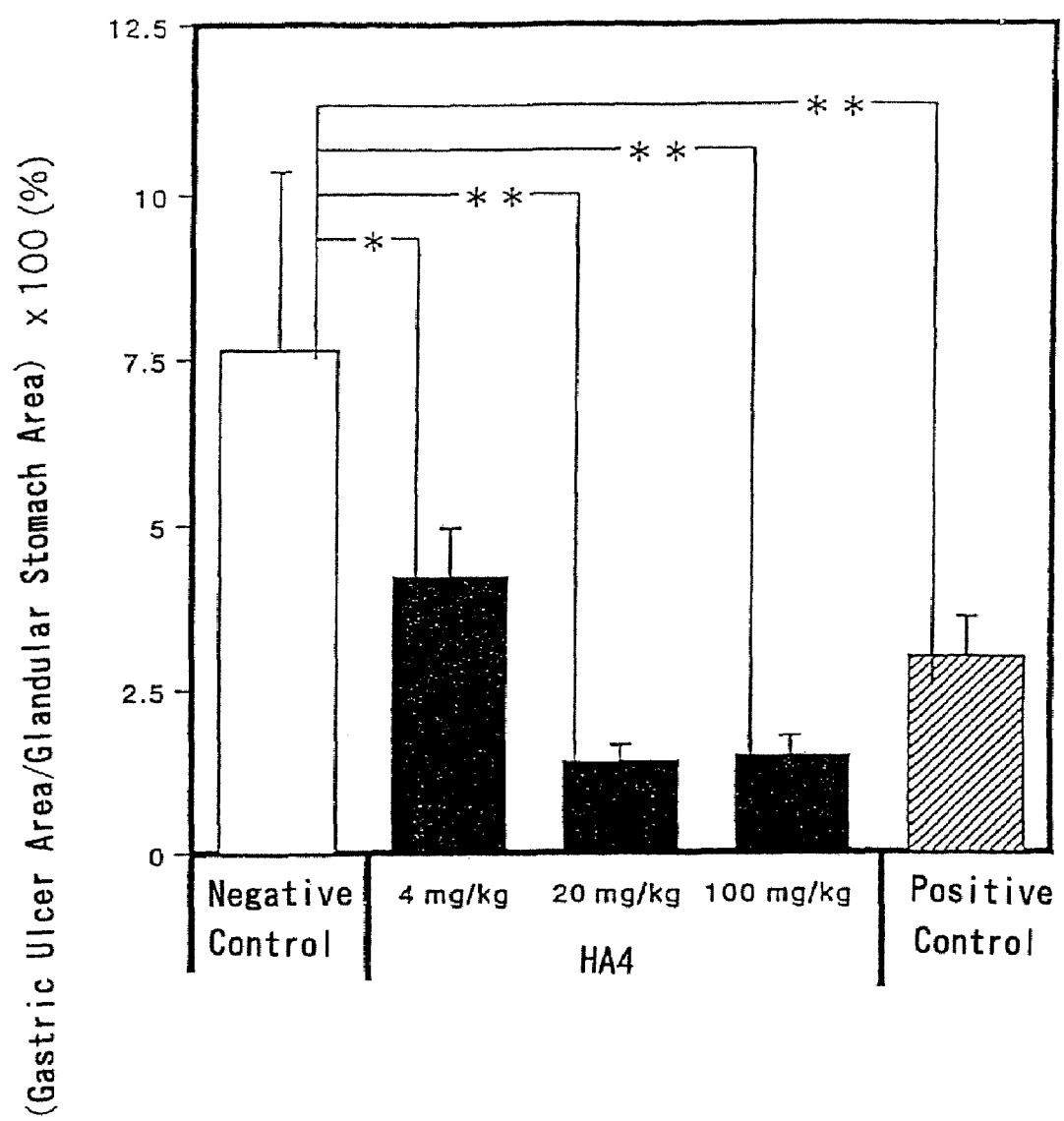
FIG. 48 shows gastric ulcer inhibitory effect of HA tetrasaccharide.
Figure 4:
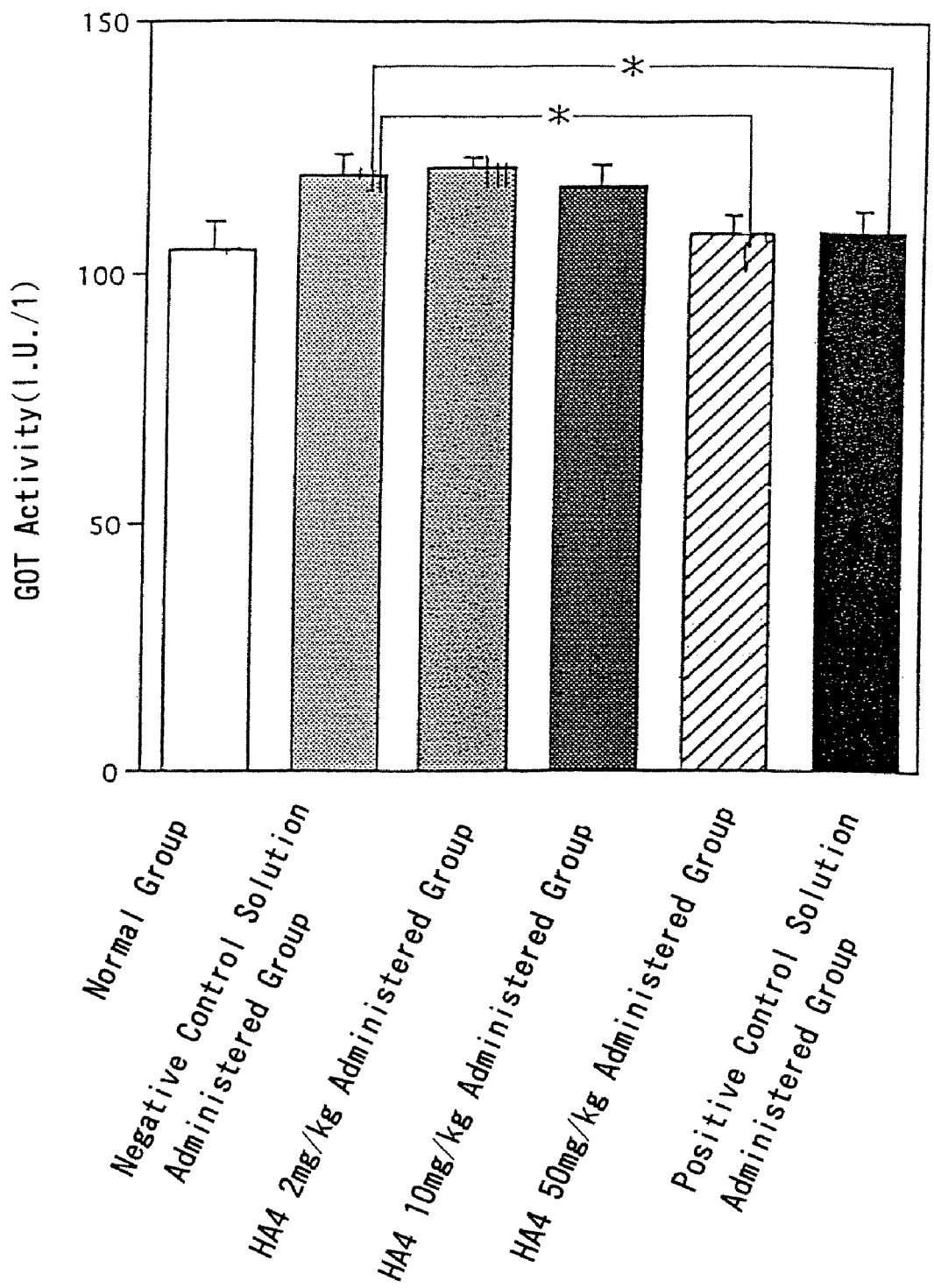

The area ratio of ulcerous portion degenerated in a dark brown color (ulcer area/glandular stomach area) was measured by using an image analysis apparatus (Image-Pro PLUS™ Version 3.0.1, produced by Media Cybernetics). The results are shown in FIG. 48. The symbols * and ** in FIG. 48 indicate significant differences with p<0.05 and p<0.01, respectively (Williams multiple range test).

As seen from the results shown in FIG. 48, the area ratio of ulcerous portion was significantly reduced in all the HA4 administered groups compared with the negative control solution administered group. In particular, the HA4 20 mg/kg administered group and 100 mg/kg administered group showed an area ratio of ulcerous portion lower than that observed for the positive control solution group.

The results mentioned above revealed that the HA oligosaccharide (HA tetrasaccharide) had superior cell and tissue protection effect also in the aspect of the effect on ulcer. It was also revealed that the aforementioned superior effect could be obtained even by oral administration of the HA oligosaccharide. Furthermore, since the rats were administered with the HA oligosaccharide (HA tetrasaccharide) beforehand and then arrested by water immersion in this experiment, and it takes a certain period of time from the start of the arrest by water immersion until ulcer is generated, it can be also said that the results of this experiment suggests that the HA oligosaccharide (HA tetrasaccharide) has a prophylactic effect.

3. Cell and tissue protection action in aspect of effect on hepatopathy

Experiment 1: Experiment Using Carbon Tetrachloride Hepatopathy Model (1) Preparation of Test Solutions for Administration A test substance was dissolved in physiological saline to obtain a test solution for administration. The concentration was determined depending on the dose mentioned below so that the volume of the solution to be administered should become 5 mL/kg.

Moreover, as a positive control solution, FAD (flavine adenine dinucleotide, Wakamoto Pharmaceutical), of which effect on the carbon tetrachloride hepatopathy model had been reported (Yakubutsu Ryouhou (Pharmacotherapy), vol. 9, Special edition, pp. 46-53), was used at a dose of 10 mg/kg. Further, physiological saline was used as a negative control solution.

(2) Administration of Test Substance Etc.

SD male rats of 5-week old were divided into a "negative control solution" administered group (n=8), "HA4 2 mg/kg" administered group (n=8), "HA4 10 mg/kg" administered group (n=8), "HA4 50 mg/kg" administered group (n=8), "positive control solution" administered group (n=8) and "normal" group (n=8).

The rats of the groups were starved from 16:00 of the day before the first administration day, orally administered with 100 mg/kg of carbon tetrachloride ($CCl_4$) before 8:00 of the next day and then intraperitoneally administered with each of the aforementioned solutions at 8:00. Thereafter, the rats were bred with maintaining starvation, and administered with each of the aforementioned solutions in the same manner as the first administration at 16:00 and 24:00. The rats were fed after the administration at 24:00 and dissected at 8:00 on the next day.

(3) Evaluation

After the dissection, blood was collected, and GOT activity and leucocyte count were measured. The GOT activity was measured by using a clinical chemistry autoanalyzer (COBAS MIRA S, Nippon Roche), and the leucocyte count was measured by using an automated hematology analyzer (Sysmex K-2000, produced by Sysmex).

Figure 50:
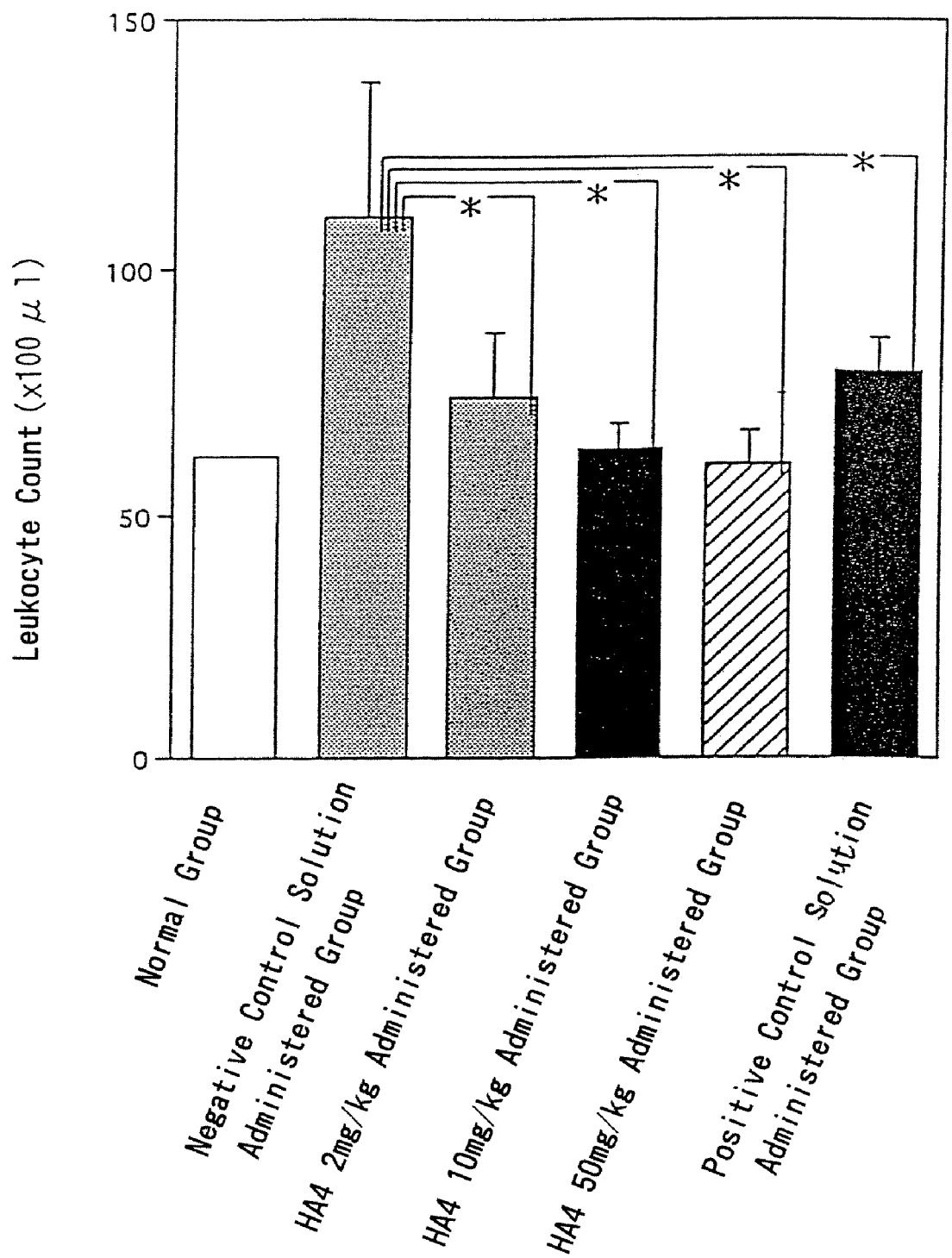
FIG. 50 shows hepatopathy inhibitory effect (leucocyte count) of HA tetrasaccharide.

The results of the former are shown in FIG. 49, and the results of the latter are shown in FIG. 50. The symbol of * in FIGS. 49 and 50 indicates presence of significant difference with $p<0.05$ (Williams multiple range test).

As seen from the results shown in FIG. 49, significant reduction of the GOT activity was observed in the HA4 50 mg/mL administered group compared with the negative control solution administered group. Moreover, as seen from the results shown in FIG. 50, significant decrease of the peripheral leucocyte count was observed for all the HA4 administered groups compared with the negative control solution administered group, and the leucocyte count was decreased compared even with FAD. These results revealed that the HA tetrasaccharide had a cell and tissue protection effect also in the aspect of the effect on hepatopathy. Furthermore, since the rats were administered with carbon tetrachloride beforehand and then administered with the HA oligosaccharide (HA tetrasaccharide) in this experiment, and it takes a certain period of time from the administration of carbon tetrachloride until hepatopathy is generated by carbon tetrachloride, it can be also said that the results of this experiments suggests that the HA oligosaccharide (HA tetrasaccharide) has a prophylactic effect.

Moreover, in this experiment, IL-10 and IL-8 concentrations in peripheral blood were also measured.

It has been reported that IL-10 is associated with one of the stress proteins (proteins that are expressed when a cell receives stress and have an action for protecting the cell), Hsp70 (J. Immunol., 164 (5), pp. 2711-2717, 2000), and it has also been reported that IL-10 suppressed hepatitis caused by concanavalin A (Autoimmunity, 31 (2), pp. 75-83, 1999).

Moreover, it has been revealed that the expression amount of IL-8 was increased in a hepatopathy model using cadmium or alcohol (Toxicology and Applied Pharmacology, 163, pp. 231-9, 2000; Acta Gastro-Enterologica Belgica, 57 (3-4), pp. 255-9, 1994), and it has also been reported that the expression of IL-8 was further inhibited by induction of Hsp70 expression (Journal of Immunology, 164, pp. 5416-23, 2000).

Figure 51:
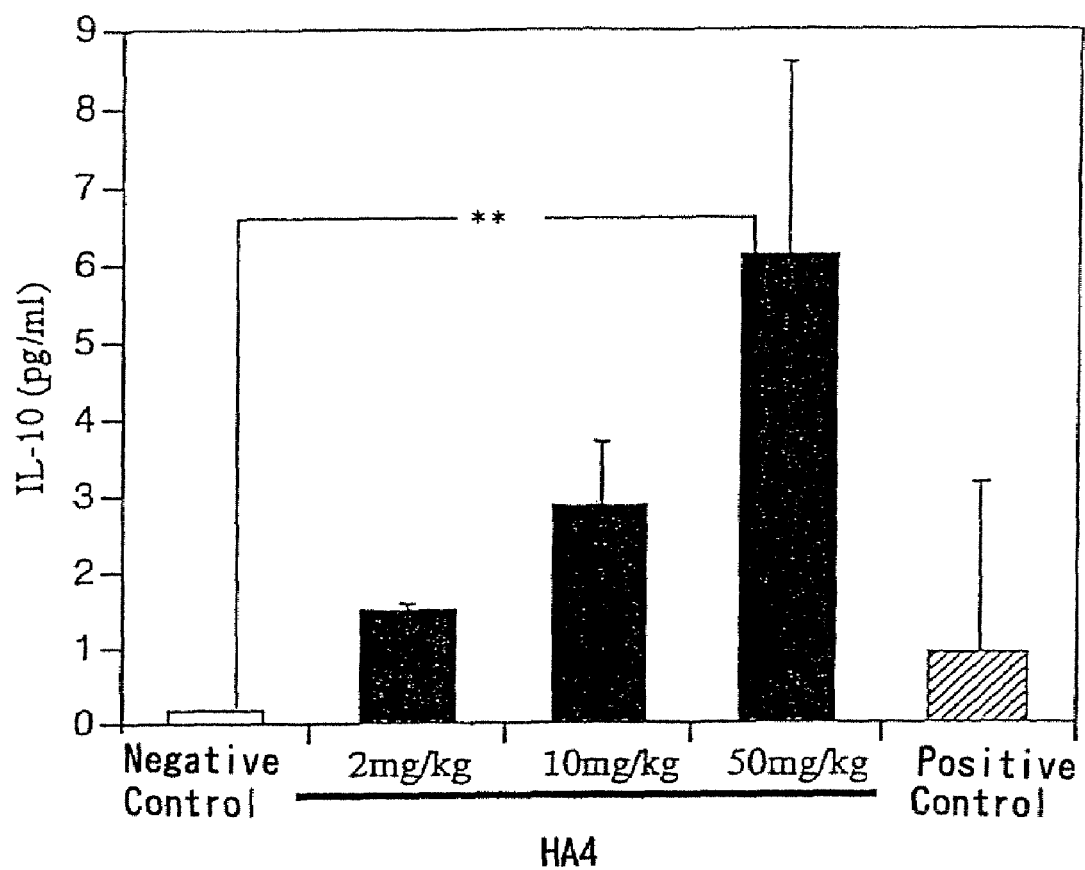
FIG. 51 shows IL-10 production promotion effect of HA tetrasaccharide.
Figure 52:
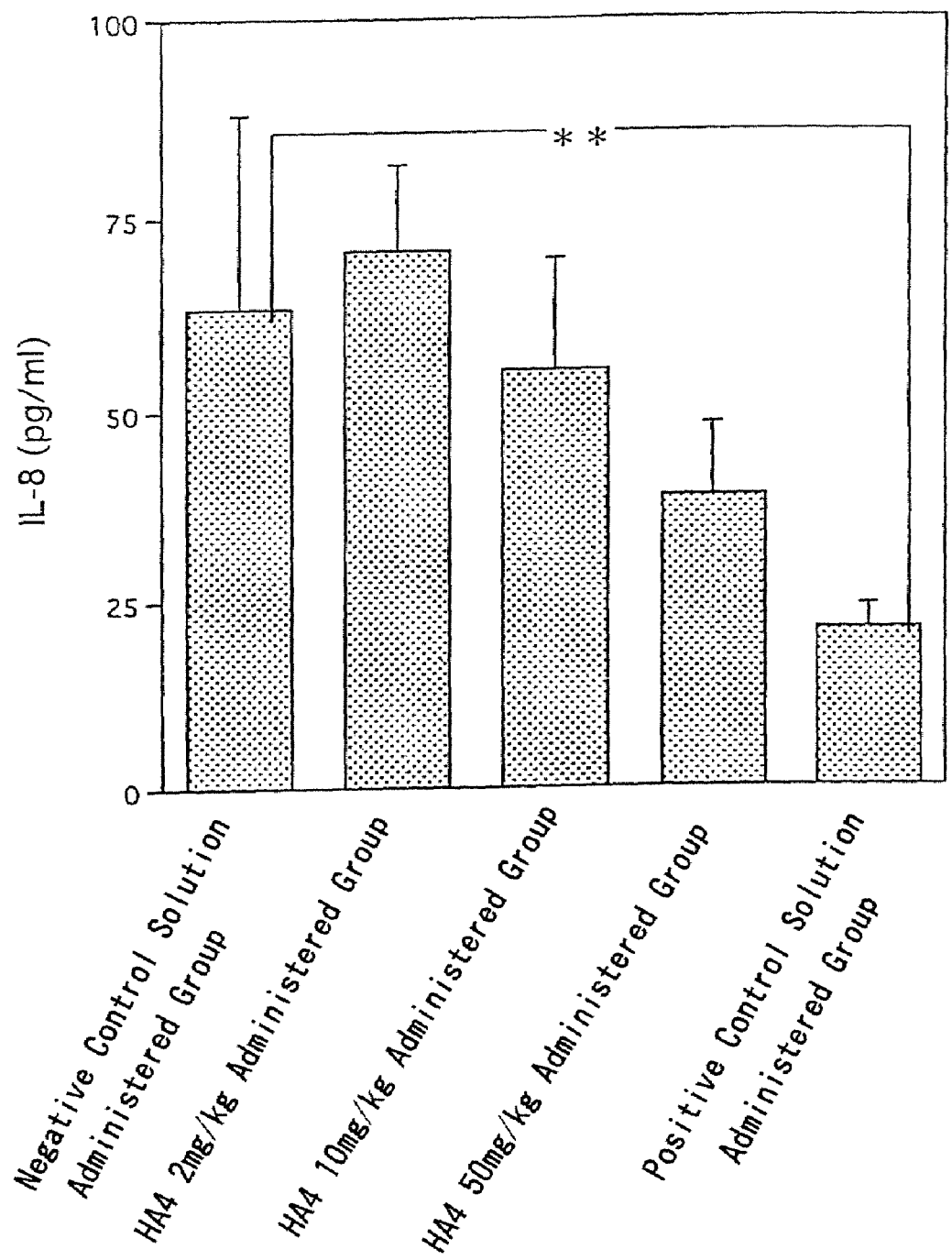
FIG. 52 shows IL-8 production inhibitory effect of HA tetrasaccharide.

IL-10 in peripheral blood was measured by using IL-10 Rat ELISA (produced by ENDOGEN). IL-8 was measured by using Panatest A Series Rat CINC-1 (IL-8) (Panapharm Laboratories). The measurement results for IL-10 are shown in FIG. 51, and the measurement results for IL-8 are shown in FIG. 52. The symbol of  in FIGS. 51 and 52** indicates presence of significant difference with $p<0.01$ (Williams multiple range test).

From the results shown in FIG. 51, it can be seen that the blood IL-10 level was increased in a manner dependent on the dose of HA4, and the blood IL-10 level was significantly higher in the HA4 50 mg/kg administered group compared with the negative control solution administered group. Further, from the results shown in FIG. 52, it can be seen that the blood IL-8 level was decreased in a manner dependent on the dose of HA4.

These results revealed that the HA oligosaccharide (HA tetrasaccharide) also had an IL-10 production promoting effect and IL-8 production inhibitory effect. This also suggests a possibility that the HA oligosaccharide (HA tetrasaccharide) may exert the aforementioned cell and tissue protection effect through promotion of the IL-10 production or inhibition of the IL-8 production. Moreover, it was also demonstrated that the HA oligosaccharide (HA tetrasaccharide) can be used also as an agent for treatment of diseases caused by decrease of IL-10 or increase of IL-8 and diseases for which promotion of the IL-10 production or inhibition of the IL-8 production is desired.

Experiment 2: Experiment using concanavalin A model

In order to confirm whether the HA oligosaccharide (HA tetrasaccharide) might be effective also on a hepatopathy model other than the carbon tetrachloride hepatopathy model, an experiment was performed by using a concanavalin A hepatopathy model.

(1) Preparation of Test Solution for Administration

The preparation, concentration, dose, volume to be administered etc. of the test solution are the same as those used in Experiment 1.

As a positive control solution, Stronger Neo-Minophagen C (Minophagen Pharmaceutical) was used at a dose of 5 mg/kg. This dose is the maximum clinical dose of the drug. Moreover, physiological saline was used as a negative control solution.

(2) Administration of Test Substance Etc.

Balb/c mice of 8-week old were divided into a "negative control solution" administered group (n=12), "HA4 2 mg/kg" administered group (n=12), "HA4 10 mg/kg" administered group (n=12), "HA4 50 mg/kg" administered group (n=12), "positive control solution" administered group (n=12) and "normal" group (n=8).

Concanavalin A (ConA, Sigma) was injected via the caudal vein at a dose of 15 mg/kg. Then, each of the aforementioned solutions was administered via the caudal vein. Thereafter, the mice were bred for 24 hours.

(3) Evaluation

The whole blood was collected from the abdominal aorta, and the GPT activity and GOT activity were measured by a clinical chemistry autoanalyzer (COBAS MIRA S, Nippon Roche) Further, the liver was extracted, and appearance of the liver was evaluated by visual inspection.

As a result, the average of GPT was about 5600 (I.U./L) in the "negative control solution" administered group. On the other hand, it was about 2200 (I.U./L) and about 1200 (I.U./L) in the "HA4 10 mg/kg" administered group and the "HA4 50 mg/kg" administered group, respectively, and both of the values were significantly lower than that observed for the "negative control solution" administered group ($p<0.01$, Dunnett multiple comparison test). In addition, it was about 4000 (I.U./L) for the "positive control solution" administered group.

Further, the average of GOT was about 6000 (I.U./L) for the "negative control solution" administered group. On the other hand, it was about 2000 (I.U./L) and about 1000 (I.U./L) for the "HA4 10 mg/kg" administered group and the "HA4 50 mg/kg" administered group, respectively, and thus both of the values were significantly lower than that observed for the "negative control solution" administered group ($p<0.01$, Dunnett multiple comparison test). In addition, it was about 4400 (I.U./L) for the "positive control solution" administered group.

Moreover, as a result of the visual inspection of the livers, both of the "HA4 10 mg/kg" administered group and the "HA4 50 mg/kg" administered group showed a lower degree of hepathopathy compared with the "negative control solution" administered group and the "positive control solution" administered group.

These results demonstrated that the HA oligosaccharide (HA tetrasaccharide) exhibited an effect also on hepatopathy caused by concanavalin A, and it was suggested that the HA oligosaccharide (HA tetrasaccharide) was effective to various hepatopathies. Further, it can be said that the results of this experiment suggest that the HA oligosaccharide (HA tetrasaccharide) has a prophylactic effect, like the results obtained by using the carbon tetrachloride model.

In addition, safety of the agents of the present invention can be estimated from the high safety of the HA oligosaccharides themselves as well as the results of the aforementioned examples.

INDUSTRIAL APPLICABILITY

The oligosaccharides of the present invention are useful as active ingredients of the drugs of the present invention and so forth.

The fractions of the present invention are HA oligosaccharide fractions that contain an HA oligosaccharide of a desired size and do not substantially contain oligosaccharides of other sizes and impurities, and are extremely useful as reagents for search of physiological activities of HA oligosaccharides, standards for analyses, drugs themselves or materials thereof.

Since an HA oligosaccharide of a specific size exhibits a remarkable effect that cannot be observed for HA oligosaccharides of other sizes as clearly seen from the results of the aforementioned examples, the drugs containing the oligosaccharides of the present invention as an active ingredient, especially Hsp expression promoter, are extremely useful. Further, if an HA oligosaccharide of such a specific size is selected, the dose can be reduced compared with HA oligosaccharides of other sizes while maintaining the same degree of effect as the HA oligosaccharides of other sizes. Therefore, they are extremely advantageous also in aspect that they enable production of more inexpensive drugs having higher safety.

Furthermore, the cell death inhibitor, cell injury inhibitor and cell and tissue protecting agent (e.g., organ preservation agent, antiulcer agent, antihepatopathic agent, IL-10 production promoter or IL-8 production suppressor) containing the oligosaccharides of the present invention as active ingredients are extremely useful, because they exhibit superior pharmaceutical effects as clearly seen from the results of the aforementioned examples and exhibit high safety.

The invention claimed is:

1. A method for preserving an organ, comprising administering an effective amount of a fraction comprising a hyaluronic acid tetrasaccharide comprising four saccharide residues and having the physicochemical properties defined in the following (1) to (6):
    (1) when the fraction is analyzed by the detection methods mentioned in the following (a) and (b) using gel filtration chromatography, the fraction shows a substantially single peak in both of the methods, and the peaks have peak areas defined in the following (a) and (b):
    (a) when the detection is performed based on absorbance at 210 nm, a relative ratio of peak area of the tetrasaccharide to the sum of peak areas of total HA oligosaccharides in the fraction is 85% or more;
    (b) when the detection is performed by using a differential refractometer, a relative ratio of peak area of the tetrasaccharide to the sum of peak areas of total HA oligosaccharides in the fraction is 98% or more;
    (2) when the fraction is analyzed based on absorbance at 210 nm by anion exchange chromatography, the fraction shows a substantially single peak, and a relative ratio of peak area of the tetrasaccharide to the sum of peak areas of total HA oligosaccharides in the fraction is 90% or more;
    (3) when the tetrasaccharide in the fraction is labeled with fluorescence and then analyzed by electrophoresis, a single band is detected, and bands of HA oligosaccharides of other sizes are not detected;
    (4) when a theoretical value of monoisotopic molecular weight or average molecular weight of the tetrasaccharide constituting the fraction is taken as 1, an actual value of the same measured for the fraction by mass spectrometry is 0.997 to 1.003 (relative value);
    (5) respective differences between theoretical values (weight %) of carbon (C), hydrogen (H) and nitrogen (N) contents in the tetrasaccharide constituting the fraction and values of the same actually measured for the elements by elemental analysis of the fraction (weight %) are all in the range of ±1 (weight %); and (6) the fraction does not substantially contain proteins, DNA and endotoxins to a subject in need thereof.

2. The method according to claim 1, wherein the hyaluronic acid tetrasaccharide is a saturated hyaluronic acid tetrasaccharide.

3. A method for preserving an organ, which comprises administering an effective amount of an isolated and substantially pure tetrasaccharide of formula (1):

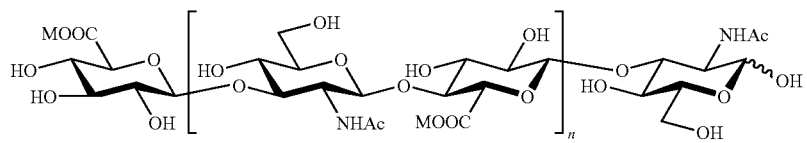

wherein n is 1, m is a proton or monovalent cation, and Ac represents an acetyl group to an organ in need of such preservation.

* * * * *